United States Patent [19]
Bona et al.

[11] Patent Number: 5,969,109
[45] Date of Patent: Oct. 19, 1999

[54] CHIMERIC ANTIBODIES COMPRISING ANTIGEN BINDING SITES AND B AND T CELL EPITOPES

[76] Inventors: Constantin Bona, 333 E. 55th St., New York, N.Y. 10022; Habib Zaghouani, 301 Cheshire Dr., Apt. 31, Knoxville, Tenn. 37919

[21] Appl. No.: 08/363,276

[22] Filed: Dec. 22, 1994

Related U.S. Application Data

[63] Continuation-in-part of application No. 07/486,546, Feb. 28, 1990, abandoned, and a continuation-in-part of application No. 07/687,376, Apr. 18, 1991, abandoned, and a continuation-in-part of application No. 08/327,636, Oct. 24, 1994, abandoned.

[51] Int. Cl.⁶ ............................ C07K 16/00; C12P 21/08
[52] U.S. Cl. .................................... 530/387.3; 530/387.1; 530/388.1; 530/388.2; 530/388.73; 530/388.75
[58] Field of Search ........................ 530/387.3, 387.1, 530/388.1, 388.2, 388.73, 388.75

[56] References Cited

U.S. PATENT DOCUMENTS

| Re. 32,833 | 1/1989 | Greene et al. . | |
|---|---|---|---|
| 5,231,167 | 7/1993 | Zanetti et al. . | |
| 5,508,386 | 4/1996 | Zanetti et al. | 530/387.3 |

FOREIGN PATENT DOCUMENTS

| 308936 | 3/1989 | European Pat. Off. . |
|---|---|---|
| WO8582121 | 5/1985 | WIPO . |
| 89/10939 | 11/1989 | WIPO . |
| WO 9009804 | 7/1990 | WIPO . |
| WO 9103562 | 3/1992 | WIPO . |
| WO 9204914 | 4/1992 | WIPO . |
| WO 9218540 | 10/1992 | WIPO . |
| WO 9414848 | 12/1993 | WIPO . |
| WO 9414847 | 7/1994 | WIPO . |
| WO 9428026 | 12/1994 | WIPO . |

OTHER PUBLICATIONS

*The Journal of Immunology*, Brumeanu et al., 1995, 154:3088–3095.
*Journal of Chromatography A*, Brumeanu et al., 1995, 696:219–225.
*Proc. Natl., Acad. Sci. USA*, Zaghouani et al., 1995, 92:631–635.
*Inter. Rev. Immunol.*, Shin et al., 1993, 10:177–186.
*Il Farmaco*, Schiavon et al., 1990, 45 (Supplemental to N.6):791–795.
*Nature*, Clarke et al., 1987, 330:381–384.
Riechmann et al Nature VOl 332:323–327, 1988.
Bodmer et al Cell vol. 52:253–258, 1988.
Rotschke et al Eur J Immunology vol. 21:2891–2894, 1991.
Herbert et al (The Dictionary of Immunology, Academic Press,) London, p. 78, 1995.
Webster's New Riverside University Dictionary, The Riverside Publishing Co., Boston, p. 1156, 1994.
Rossiter et al., 1994, Eur. J. Immunol. 24:1244–1247.
Zaghouani et al., 1994, FASEB J. 6:A962, abstract 5570.
Billetta and Zanetti, 1993, Inter. Rev. Immunol. 10:25.
Biotechnology News, Jan. 22, 1993.
Leff, BioWorld Today, Jan. 12, 1993.
Kuzu et al., 1993, International Immunol. 5:1301–1307.
Selisko et al., 1993, J. Chromatogr. 641:71–79.
Zaghouani et al., 1993, Abstract presented at Conference on Advances in AIDS Vaccine Development, Alexandria, VA Oct. 30—Nov. 4, 1993.
Zaghouani et al., 1993, Eur. J. Immunol. 23:2746–2750.
Zaghouani et al., 1993, International Review Immunol. 10:265–278.
Zaghouani et al., 1993, Science 259:224–227.
Zanetti et al., 1993, EMBO J. 12:4375–4384.
Billetta, 1992, FASEB J. 6:A2012, abstract 6226.
Cunningham–Rundles et al., 1992, J. Immunol. Methods 152:177–190.
Kuzu et al., 1992, FASEB J. 6:A1968, abstract 5977.
Lanza et al., 1992 FASEB J. 6:A4100, abstract 2690.
Li et al., 1992, J. Virol. 66:399–404.
Nelson et al., 1992, Proc. Natl. Acad. Sci. U.S.A. 89:7380–7383.
Partidos et al., 1992, Eur. J. Immunol 22:2675–2680.
Rossi et al., 1992, FASEB J. 6:A1400, abstract 2691.
Snider et al., 1992, J. Chromatogr. 599:141–155.
Warren et al., 1992, J. Clin. Microbiol. 30:126–131.
Warren et al., 1992, J. Virol. 66:5210–5215.
Zaghouani et al., 1992, J. Immunol. 148:3604–3609.
Zanetti et al., 1992, Immunological Reviews 1992, No. 130, pp. 125–150.
Zanetti, 1992, Nature 355:476–477.
Billetta et al., 1991, Proc. Natl. Acad. Sci. U.S.A. 88:4713–4717.
Kitamura et al., 1991, Cancer Res. 51:4310–4315.
Klibanov et al., 1991, Biochim. Biophys. Acta 1062–142.
Leclerc, 1991, J. Immunol. 147:3545–3552.
Moran et al., 1991, Journal of Immunology 146:321–326.
Neville et al., 1991, presented at the American Association of Pharmaceutical Scientists', Sixth Annual Meeting, Washington, DC Nov. 17–21.
Rotzschke et al., 1991, Immunol. Today 12:447–455.
Waldmann, 1991, Science 252:1657.
Zaghouani et al., 1991, FASEB J. 5:A1334, abstract 5587.
Zaghouani et al., 1991, Proc. Natl. Acad. Sci. U.S.A. 88:5645–5649.
Billetta, 1990, FASEB J. 4:A1763, abstract 402.

(List continued on next page.)

*Primary Examiner*—Paula K. Hutzell
*Assistant Examiner*—Susan Ungar
*Attorney, Agent, or Firm*—Lisa B. Kole

[57] ABSTRACT

The present invention relates to chimeric antibodies which comprise a B cell epitope, a T cell epitope, and/or an antigen binding site. The chimeric antibodies may be produced by replacing at least a portion of an immunoglobulin molecule with the desired epitope or antigen binding site such that the functional capabilities of the epitope and the parent immunoglobulin are retained. The chimeric antibodies of the invention may be used to enhance an immune response against pathogens and tumor cells in subjects in need of such treatment.

6 Claims, 33 Drawing Sheets

OTHER PUBLICATIONS

Durda et al., 1990, Aids Research and Human Retroviruses 6:1115–1123.
Goron et al., 1990, Journal of Immunology 129:199–205.
Ho et al., 1990, Eur. J. Immunol. 20:477–483.
Kitamura et al., 1990, Biochem. Biophys. Res. Commun.:1387.
Moran et al., 1990, J. Immuno. Methods 129:199–205.
Sollazzo et al, 1990, Protein Engineering 4:215–220.
Sollazzo et al., 1990, in *The Year In Immunology 1989–1990*, Cruse et al., eds., vol. 6, Basel Karger, pp. 162–184.
Sollazzo et al., 1990, Protein Engineering 3:531–539.
Carlsson et al., 1989, Bio/Technology 7:567–573.
Liou et al., 1989, J. Immuno. 143:3967–3975.
Sollazzo et al., 1989, Cur. J. Immunol. 19:453–457.
Webb et al., 1989, Proc. Natl. Acad. Sci. USA, 86:7731–7735.
Dangl et al., 1988, EMBO. J. 7:1989–1994.
Morrison et al., 1988, Clin. Chem. 34(9):1668–1675.
Rathburn et al., 1988, J. Mol. Biol. 202:383–395.
Ito et al., 1987, J. Immunol. Met. 103:229.
Jackson et al., 1987, Anal–Biochem. 165:114–127.
Lewin, 1987, "Genes III", John Wiley and Sons, N.Y. pp. 642–649.
Moran et al., 1987, Vir. Immunol. 1:1–12.
Sanz et al., 1987, Proc. Natl. Acad. Sci. USA 84:1085–1089.
Wilkinson et al., 1987, Immunol. Lett. 15:17–22.
Wong et al., 1987, Journal of Immunology 139:1369–1374.
Zanetti et al., 1987, Immunology Today 8:18–25.
Jones et al., 1986, Nature 321:522–525.
Morrison et al., 1986, Mount Sinai J. Med. 53:175–180.
Oi et al., 1986, Bio Techniques 4:214–221.
Perez et al., 1985, Letters to Nature 316:354–356.
Mosmann, 1983, J. Immunol. Methods 65:55.
Swain et al., 1983, J. Exp. Med. 158:822–835.

CHIMERIC ANTIBODIES COMPRISING ANTIGEN BINDING SITES AND B AND T CELL EPITOPES

SPECIFICATION

This application is a continuation-in-part of U.S. Ser. No. 07/486,546, filed Feb. 28, 1990, now abandoned, of U.S. Ser. No. 07/687,376 filed on Apr. 18, 1991 now abandoned, and of U.S. Ser. No. 08/327,636 filed on Oct. 24, 1994, now abandoned, which are incorporated by reference herein.

1. INTRODUCTION

The present invention relates to chimeric antibodies which comprise a B cell epitope, a T cell epitope, and/or an antigen binding site. The chimeric antibodies may be produced by replacing at least a portion of an immunoglobulin molecule with the desired epitope or antigen binding site such that the functional capabilities of the epitope and the parent immunoglobulin are retained. The chimeric antibodies of the invention may be used to enhance an immune response against pathogens or tumor cells in subjects in need of such treatment.

2. BACKGROUND OF THE INVENTION

2.1. The Immune Response

Mammals, including man, possess the ability to mount an immune response as a defense against pathogens from the environment as well as against aberrant cells, such as tumor cells, which develop internally. The immune response is the result of complex interactions between a variety of cells and factors, but has two main components: a cellular component, in which cells directly attack an offending agent (bearing an antigen) and a humoral component, in which antibody molecules bind specifically to the antigen and aid in its elimination.

The primary cells involved in producing the immune response are lymphocytes, of which there are two principal classes, B cells and T cells. Antibodies are produced by B cells. A mature B cell which specializes in the production of antibody molecules is known as a plasma cell.

Mature T cells have been classified into four subpopulations based on the different tasks they perform. These subpopulations include (1) helper T cells ($T_h$), which are required for promoting or enhancing B cell antibody production; (2) cytotoxic (or cytolytic) T lymphocytes (CTL), which directly kill their target cells by cell lysis; (3) suppressor T cells ($T_s$), which suppress or down-regulate immunological reactions; and (4) T lymphocytes which participate in delayed type hypersensitivity reactions ($T_{h1}$).

These different subpopulations of T cells express a variety of cell surface proteins, some of which are termed "marker proteins" because they are characteristic of particular subpopulations. For example, most $T_h$ cells express the cell surface CD4 protein, whereas most CTL and $T_s$ cells express the cell surface CD8 protein. Additionally, mature T cells can be distinguished from immature T cells (thymocytes) by the presence of the cell surface T cell receptor (TCR), a transmembrane protein complex which is capable of recognizing antigen in association with self-antigens encoded by major histocompatibility complex ("MHC") genes.

Initiation and maintenance of immune responses involve cell to cell interactions and depend on the recognition of and interactions between particular proteins or protein complexes on the surface of B cells, T cells, and foreign substances called "antigens".

Both cell-mediated and antibody-mediated components of the immune response begin when a T or B cell recognizes a foreign antigen by binding to a specific site on the antigen; that specific site is known as an "epitope".

The cell-mediated response involves the lytic activity of CTL activated by exposure to antigen and proceeds in the absence of B cells. A CTL programmed to recognize a particular antigenic epitope (a "CTL epitope") will lyse a cell bearing that epitope on its surface.

For the antibody-mediated response to occur, a $T_h$ cell which has been activated by exposure to a foreign antigen (a "$T_h$ epitope") interacts with a B cell, which has been activated by exposure to a particular B cell epitope on the same foreign antigen, to stimulate the B cell to produce humoral proteins known as immunoglobulins or antibodies. The antibodies produced by the B cell recognize antigen bearing, on its surface, the B cell epitope.

Thus, the immune response toward an offending pathogen or tumor cell consists of concerted action between $T_h$, CTL and B cells which is largely triggered by antigen-mediated signals. This allows the immune response to be selectively directed toward the pathogen or tumor cells, and avoids the destruction of non-infected, non-malignant cells.

2.2. Immunoglobulin Genes

Exemplary of the basic components of antibody structure is human immunoglobulin G (IgG). As shown schematically in FIG. 1A, IgG is a tetrameric protein complex formed from two identical heavy (H) chains and two identical immunoglobulin light (L) chains. These chains are joined together by disulfide bonds into a Y-shaped antibody complex. In solution however, the molecule takes on a more globular shape.

Amino acid sequence analysis of immunoglobulins has led to the definition of specific regions with various functional activities within the heavy chains. Each light chain and each heavy chain has a variable region ($V_L$ and $V_H$, respectively) comprised within the first 100 amino acids located at its amino terminus. Three dimensional pairing of the $V_L$ and $V_H$ regions constitute the antigen-recognition portion or "antigen combining site" ("ACS") of the IgG molecule. Because of the tetrameric nature of immunoglobulins, there are two identical antigen combining sites per molecule. The variable domains of these chains are highly heterogeneous in sequence and provide the diversity for antigen combining sites to be highly specific for a large variety of antigenic structures. The heterogeneity of the variable domains is not evenly distributed throughout the variable regions, but is located in three segments, called complementarity determining regions ("CDRs"), as shown in FIG. 1B (Watson et al., 1987, Molecular Biology of the Gene, Fourth Edition, Benjamin/Cummings Publishing Co., Inc., Menlo Park, Calif., p. 845).

Each of the heavy chains also includes three or four constant regions (designated $C_{H1}$, $C_{H2}$, $C_{H3}$ and, when appropriate, $C_{H4}$), depending on antibody class, which do not vary significantly among antibodies of a single class. The constant regions do not participate in antigen binding, but are associated with a number of biological activities known as "effector functions", such as binding to Fc receptors on cell surfaces and to complement proteins. In addition, the heavy chains have a hinge region separating $C_{H1}$ and $C_{H2}$ from the remainder of the molecule. The hinge imparts flexibility to the tetramer.

The light chains have a single constant region ($C_L$). The pairing of $C_L$ and $C_{H1}$ produce the first constant domain, $C_1$, while the pairing of the $C_{H2}$ regions produces the second constant domain, $C_2$ and the pairing of the $C_{H3}$ regions produces the third constant domain, $C_3$.

A light chain pairs with a heavy chain through a disulfide bond which attaches $C_{H1}$ to $C_L$. The two heavy chains of the molecule pair together through disulfide bonds at the junction between the hinge region and $C_{H2}$.

Mammals are able to produce antibodies to a seemingly infinite variety of antigens. In order to provide such an extensive repertoire, immunoglobulin genes have evolved so as permit the production of vast numbers of different immunoglobulin proteins from a finite number of genes. This diversity is due, in part, to genetic rearrangement of immunoglobulin genes. A single gene, in an undifferentiated cell, contains a number of different regions.

FIG. 1C depicts the genetic events leading to the synthesis of kappa light chain. In the kappa light chain gene, there are three regions, a $V_K$ region, a $J_K$ region, and a $C_K$ region. Both the $V_K$ and $J_K$ regions contain a number of domains. FIG. 1D depicts the genetic events leading to the synthesis of an immunoglobulin heavy chain, and illustrates that heavy chain genes contain an even greater number of regions, including $V_H$, $D_H$, $J_H$, and constant regions, each of which contains multiple elements. Before a B cell can produce antibody molecules, its heavy and light chain immunoglobulin genes must rearrange to combine one element from each region. Providing yet more diversity, there are several immunoglobulin classes with varying features. For a review of immunoglobulin genetics and protein structure see Lewin, "Genes III", John Wiley and Sons, N.Y. (1987) and Benjamini and Leskowitz, 1988, Immunology, Alan R. Liss, Inc., New York, pp.75–84 (for FIGS. 1C and 1D).

2.3. Therapeutic Manipulations of the Immune Response

Genetic engineering techniques have been applied to components of the immune system in hopes of enhancing the natural immune response and to provide reagents for performing diagnostic tests.

Antibodies are extremely important in diagnostic and therapeutic applications due to their diversity and specificity. Molecular biology techniques have been used to increase the availability of antibodies for scientific applications.

For instance, a single antibody producing B cell can be immortalized by fusion with a tumor cell and expanded to provide an in vitro source of antibodies of a single specificity known as a "monoclonal antibody" (mAb). Such an immortal B cell line is termed a "hybridoma".

Until recently, the source of most mAb has been murine (mouse) hybridomas. Although they have been used extensively in diagnostic procedures, murine mAb are not well suited for induction of passive immunity or other therapeutic applications in mammals including humans and nonsyngeneic mice. Moreover, murine antibodies are recognized as foreign by other mammalian species and elicit an immune response which may itself cause illness. Human mAb would therefore be extremely useful in the treatment of a wide variety of human diseases.

To overcome the problems of immune responses to foreign mAb and the lack of suitable human mAb, at least in part, genetic engineering techniques have been used to construct so-called "humanized" immunoglobulin molecules which contain the antigen binding complementarity determining regions of the murine antibodies but in which the remainder of the molecule is composed of human antibody sequences which are not recognized as foreign. Jones et al., "Replacing the Complementarity-Determining Regions in a Human Antibody With Those From a Mouse", Nature, 321:522–525 (1986). These hybrid "humanized" antibodies eventually may be used as "immunotherapeutic" reagents in humans.

In further applications of genetic engineering technology, protein sequences corresponding to the epitopes of antigens of various organisms have been prepared both synthetically and by recombinant DNA techniques for use in vaccines. Administration of such synthetic epitopes has been problematic, however, in view of the short half-life of peptides in the mammalian body. In many cases, effective exposure to such peptides has been too brief to permit the induction of a satisfactory immune response.

3. SUMMARY OF THE INVENTION

The present invention relates to chimeric antibodies which comprise a B cell epitope, a T cell epitope, and/or an antigen binding site.

It is based, at least in part, on the discovery that the replacement of at least a portion of an immunoglobulin molecule with a peptide comprising a B cell epitope, T cell epitope, or antigen binding site may be accomplished without eliminating the functional activities of either the epitope/antigen binding site or the parent immunoglobulin molecule. According to the invention, antibody molecules comprising an inserted T cell or B cell epitope may effectively induce a T cell or B cell immune response, respectively.

In view of these properties, and because of the longer half-lives exhibited by immunoglobulin molecules relative to peptides, the chimeric antibodies of the invention may provide, in vaccine development, an attractive alternative to synthetic peptides bearing the same epitopes. Such chimeric antibodies may not only prolong exposure time to the antigen, but may recruit elements of the immune system so as to augment and improve the efficiency of the overall immune response.

In various embodiments of the invention, chimeric antibodies may be produced which contain more than one B cell epitope, T cell epitope, or antigen binding site, including combinations of these elements.

In one nonlimiting embodiment, a chimeric antibody comprises both a B cell epitope as well as a helper T cell epitope. Such an antibody may induce the production of antibodies directed toward the B cell epitope, thereby augmenting the effectiveness of the humoral component of the immune response.

In further nonlimiting embodiments of the invention, the recombinant antibody molecules are covalently linked to polyethylene glycol ("pegylated"). Such pegylated recombinant antibodies are capable of producing an enhanced immune response in the absence of adjuvants.

In preferred embodiments of the invention, where a chimeric antibody is to be used in a human subject, the constant region of the antibody comprises a majority of human immunoglobulin constant region peptide sequence so as to avoid an interspecies immune response, because the strongest antigenic determinants are located on the Ig constant regions.

4. DESCRIPTION OF THE FIGURES

Figure 6:
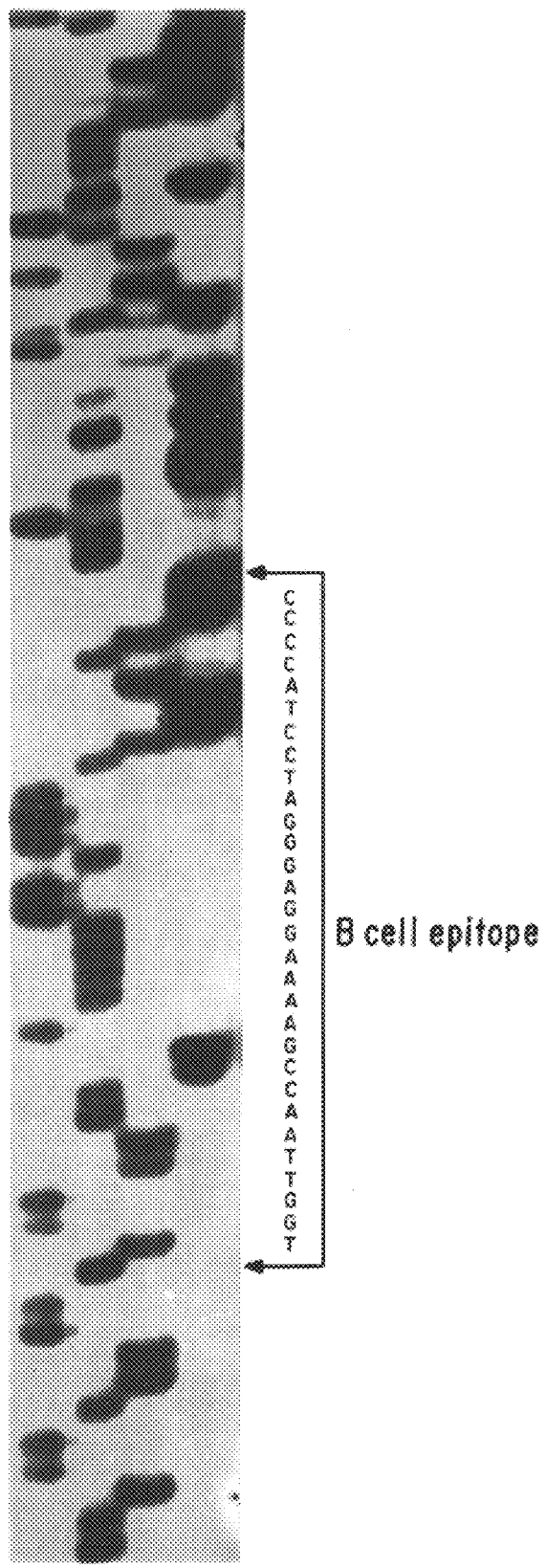

FIG. 6 presents nucleotide sequencing analysis of two clones, termed C3 and C8, which show the deletion of CDR2 sequence of 91A3 $V_H$ and insertion in the correct frame of sequence encoding the B cell epitope (SEQ ID NO: 16).

FIG. 7. Schematic representation and immunochemical properties of Ig-HIV-1 peptide chimeras.

(FIGS. 7A–C): The H and L chain variable regions (filled boxes) of the murine anti-arsonate 91A3 antibody (Rathburn et al., 1988, J. Mol. Biol. 202:383–395; Sanz et al., 1987, Proc. Natl. cad. Sci. USA. 84:1085–1089) were used along with the H and L chain constant regions (hatched boxes) of human Kappa and γ1 chains (Dangl et al., 1988, EMBO.J. 7:1994–1988; Oi et al., 1986, Bio Techniques 4:214–221) to generate Ig chimeras carrying HIV-1 $V_3$ determinants (open squares). Ig-$V_3$C, carries a 19 amino acid residue consensus sequence from the PND of the $V_3$ loop of HIV-1; Ig-$V_3$M, carries a 19 amino acid residue sequence from the PND of the $V_3$ loop of the WMJ2 HIV-1 isolate; and Ig-W is a control Ig that carries the natural D segment.

(FIGS. 7D to 7F): The Ig-HIV-1 peptide chimeras were assayed for heavy and light chain assembly (FIG. 7D) by a capture assay where 10 ng of purified chimeras were incubated on plates coated with anti-human kappa mAb and captured chimeras were revealed with $^{125}$I-labeled goat antibodies specific for the Fc region of human γ1. The antigenicity of HIV-1 peptides on the chimeras was assayed by incubating Ig chimera coated plates with rabbit antibodies specific for either the consensus (FIG. 7B) or the WMJ2 (FIG. 7F) HIV-1 $V_3$ sequences and bound rabbit antibodies were revealed with $^{125}$I-labeled goat anti-rabbit IgG antibodies. Ig-HA is a murine Ig chimera expressing a T helper epitope of the hemagglutinin antigen of influenza virus (Zaghouani et al., 1993, Science 259:224–227), and is used as negative control.

Figure 8A:
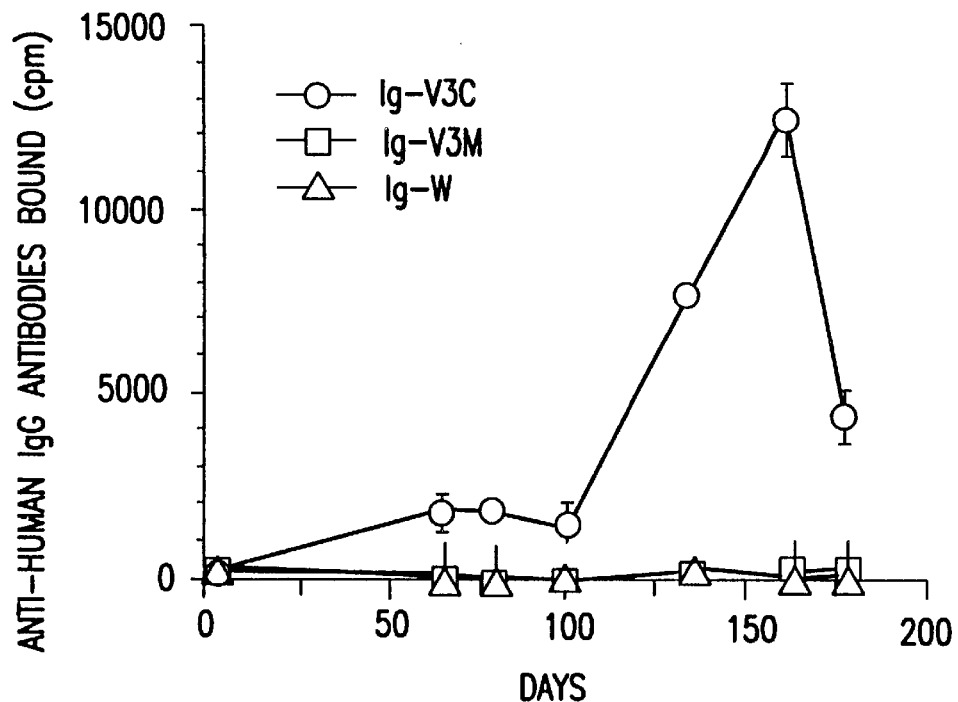
Figure 8B:
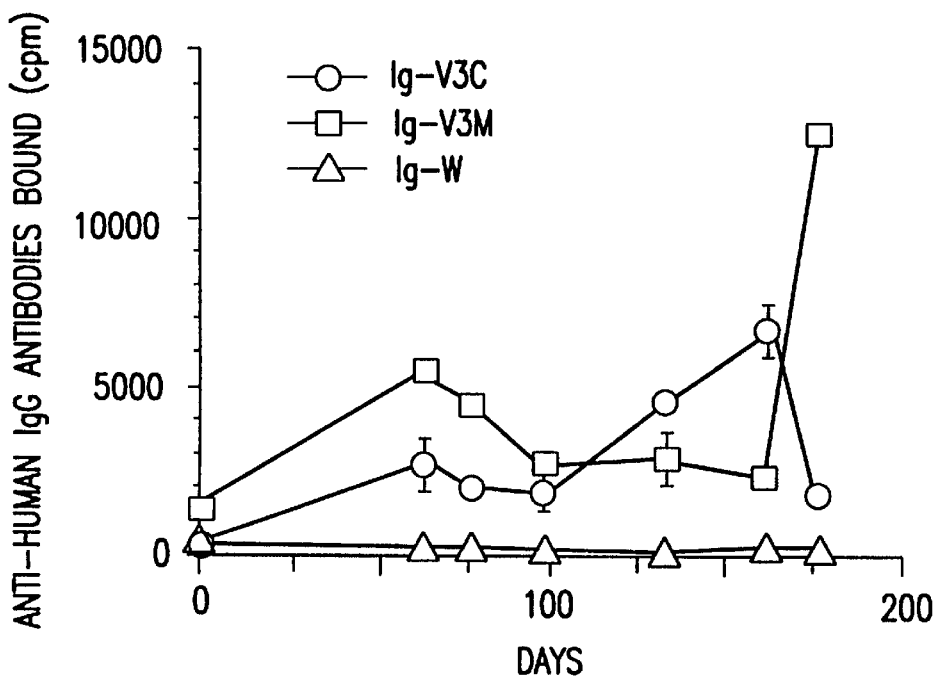
Figure 8C:
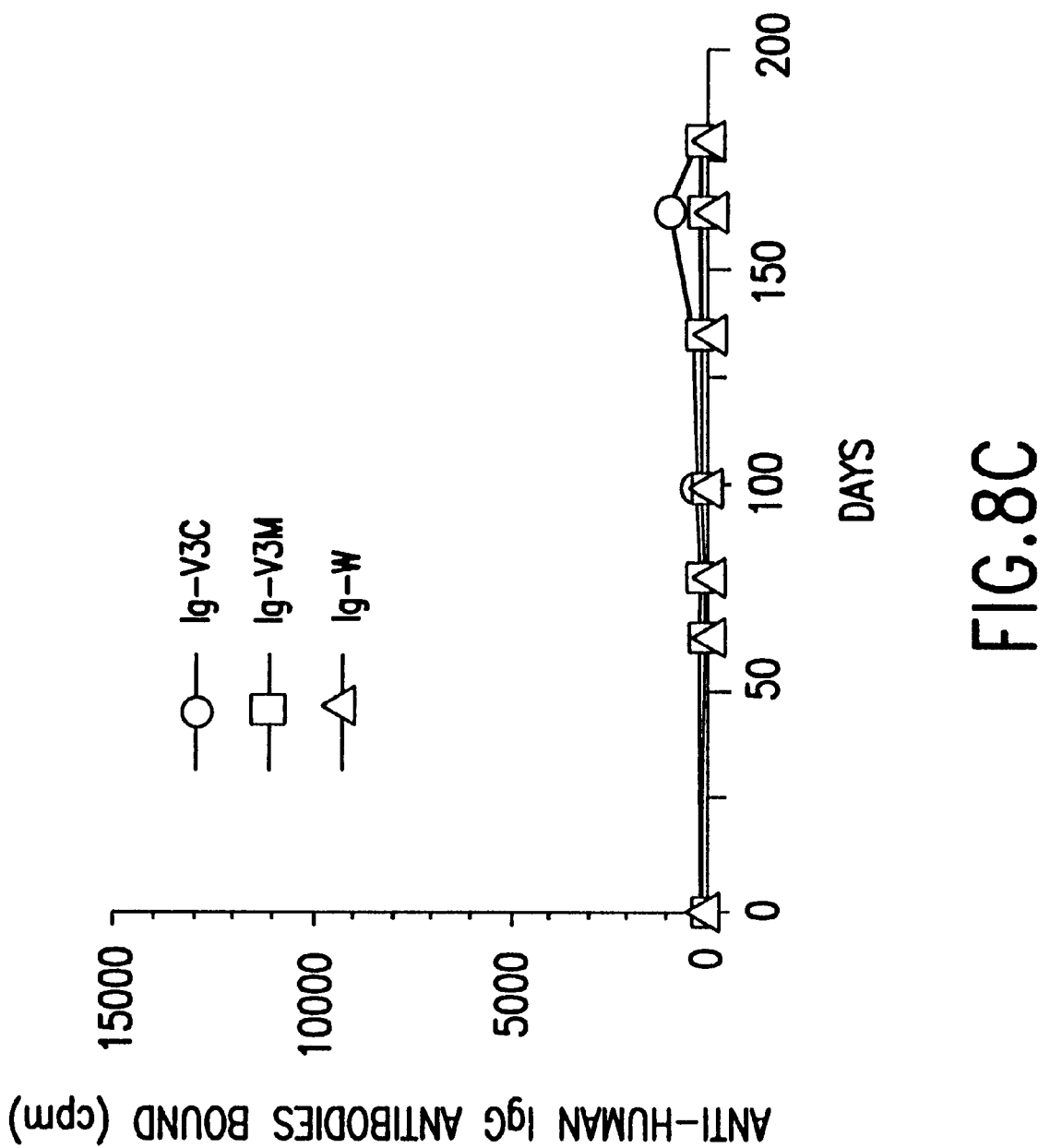

FIG. 8. Production of anti-PND antibodies subsequent to immunization of baboons with Ig-$V^3$C and Ig-$V_3$M. Adult baboons were immunized with the indicated Ig chimeras, bled and their sera were assayed for binding to $V_3$C-BSA conjugate (results shown in FIG. 8A), to $V_3$M-BSA conjugate (results shown in FIG. 8B), to 519–535-BSA conjugate (results shown in FIG. 8C), and to BSA (not shown) by radioimmunoassay. The immunization and bleeding schedule was as follows: baboons were bled at day 1 and were immunized with 500 µg of Ig-peptide chimeras emulsified in incomplete Freund's Adjuvant at day 15, and in Alum at days 29 and 43. The animal were bled at days 65, 80, and 101. They were boosted with 500 µg Ig-peptide chimeras in Alum at day 122 and bled at day 136. Finally, 500 µg Ig-peptide chimeras were given as a boost at day 150 and the animals were bled at days 164 and 178. The sera were tested at various dilutions (1:10, 1:100, and 1/1000) and the data shown are those obtained with 1:100 serum dilution. Each dilution was tested in triplicate wells and the indicated cpm represent the mean±SD after deduction of background cpm obtained on plates coated with BSA.

Figure 9:
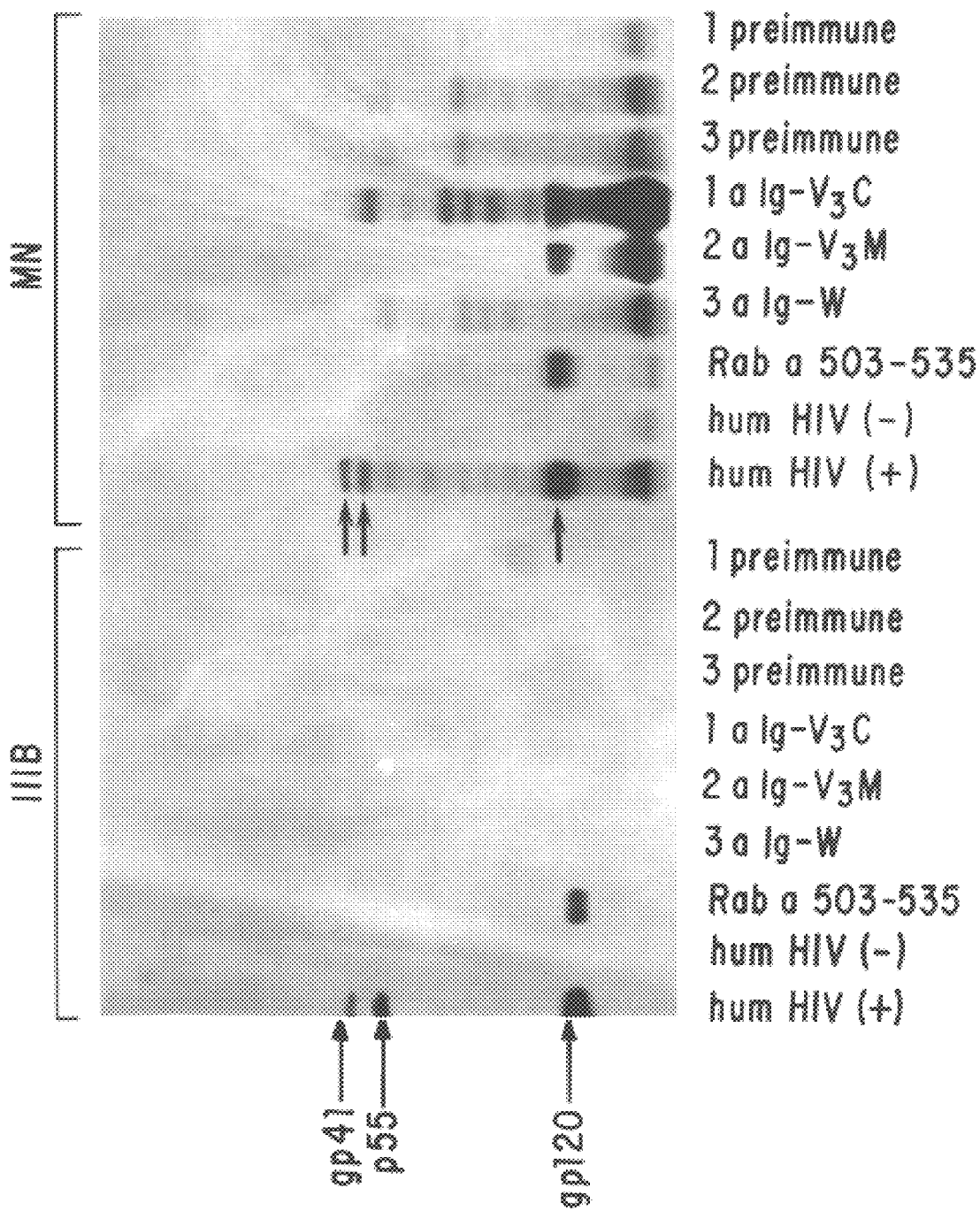

FIG. 9. Radioimmunoprecipitation of HIV-1 gp120 by anti-serum from baboons immunized with Ig-$V_3$M and Ig-$V_3$C. Precipitation was performed using lysates from MN (left panel) and IIIB (right panel) isolates. 1 preimmune, 2 preimmune, and 3 preimmune, are sera collected at day 1 from baboons numbered 1 to 3; 1 a Ig-$V_3$C, anti-serum from baboon number 1 immunized with Ig-$V_3$C collected at day 164; 2 a Ig-$V_3$M, anti-serum from baboon number 2 immunized with Ig-$V_3$M collected at day 164; 3 a Ig-W, anti-serum from baboon number 3 immunized with Ig-W collected at day 164; Rab a 503–535, a positive control anti-serum from a rabbit immunized with the peptide 503–535 which corresponds to a conserved sequence at the carboxy-terminal end of gp120 of HIV-1 and are known to precipitate the envelope protein (Zaghouani et al., 1991, Proc. Natl. Acad. Sci. USA 88:55645–5649); hum HIV (+), serum from HIV-1 infected individual; and hum HIV (−), serum from HIV negative individual. These precipitation patterns were obtained with 20 µl of baboon serum, 10 µl of rabbit serum and 1 µl of human serum.

Figure 10A:
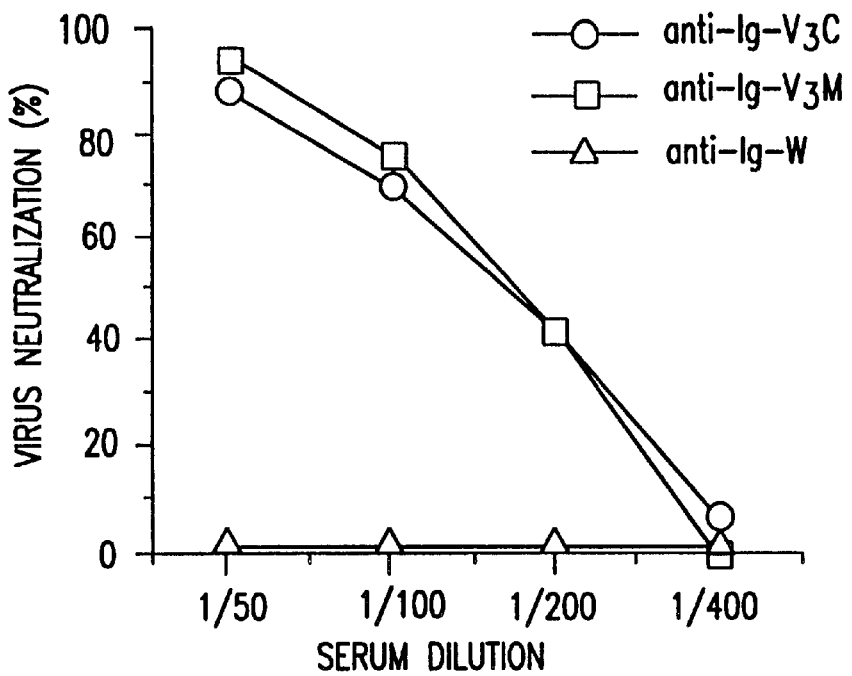
Figure 10B:
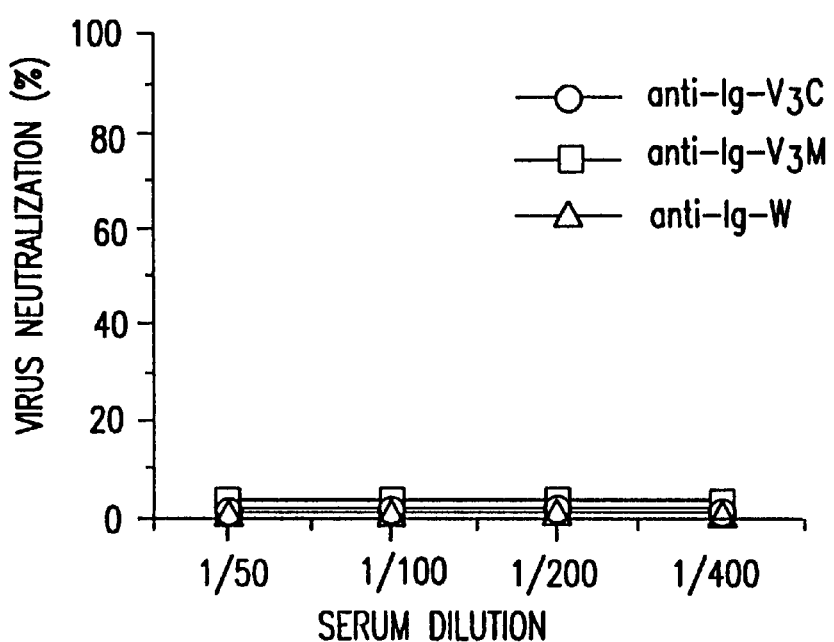

FIG. 10. Neutralization of MN isolate by anti-serum from baboon immunized with Ig-$V_3$M and Ig-$V_3$M. Sera from baboons immunized with indicated chimeras were tested for HIV-1 MN (as shown in FIG. 10A) and IIIB (as shown in FIG. 10B) neutralizing activity. All bleeds from day 1 to day 178 were tested and the data shown are those obtained with sera collected at day 164. The percent neutralization was calculated as described (Warren et al., 1992, J. Clin. Microbiol. 30:126–131; Warren et al., 1992, J. Virol. 66:5210–5215).

FIG. 11. Production of antibodies specific for $V_3$ derived peptides by human lymphocytes stimulated with Ig-$V_3$M and Ig-$V_3$M coupled to tetanus toxoid (Ig-$V_3$M-TT). PBMC from HIV-1 infected individuals (CE and SLF) as well as from a non infected co-worker (K) were incubated for 7 to 10 days with graded amounts of Ig-$V_3$M-TT (in FIGS. 11A, 11D and 11G), Ig-$V_3$M (in FIGS. 11B, 11E and 11H), or Ig-W-TT (in FIGS. 11C, 11F and 11I) and subsequently, the culture supernatants were tested for binding to $V_3$M-BSA conjugate (in FIGS. 11A, 11B, and 11C), to $V_3$C-BSA conjugate (in FIGS. 11D, 11E and 11F), to NP147–161-BSA (bottom panel) and to BSA (background control not shown). Each supernatant (50 µl) was tested in triplicate and the data are presented as mean±SD after deduction of background obtained on plates coated with BSA. The results shown are those obtained after 10 days of incubation of the cells with the Ig-peptide chimeras and are representative of two experiments. Similar results were obtained for the experiments carried out for a period of 7 days of incubation of the PBMC with the chimeric immunoglobulins.

Figure 12:
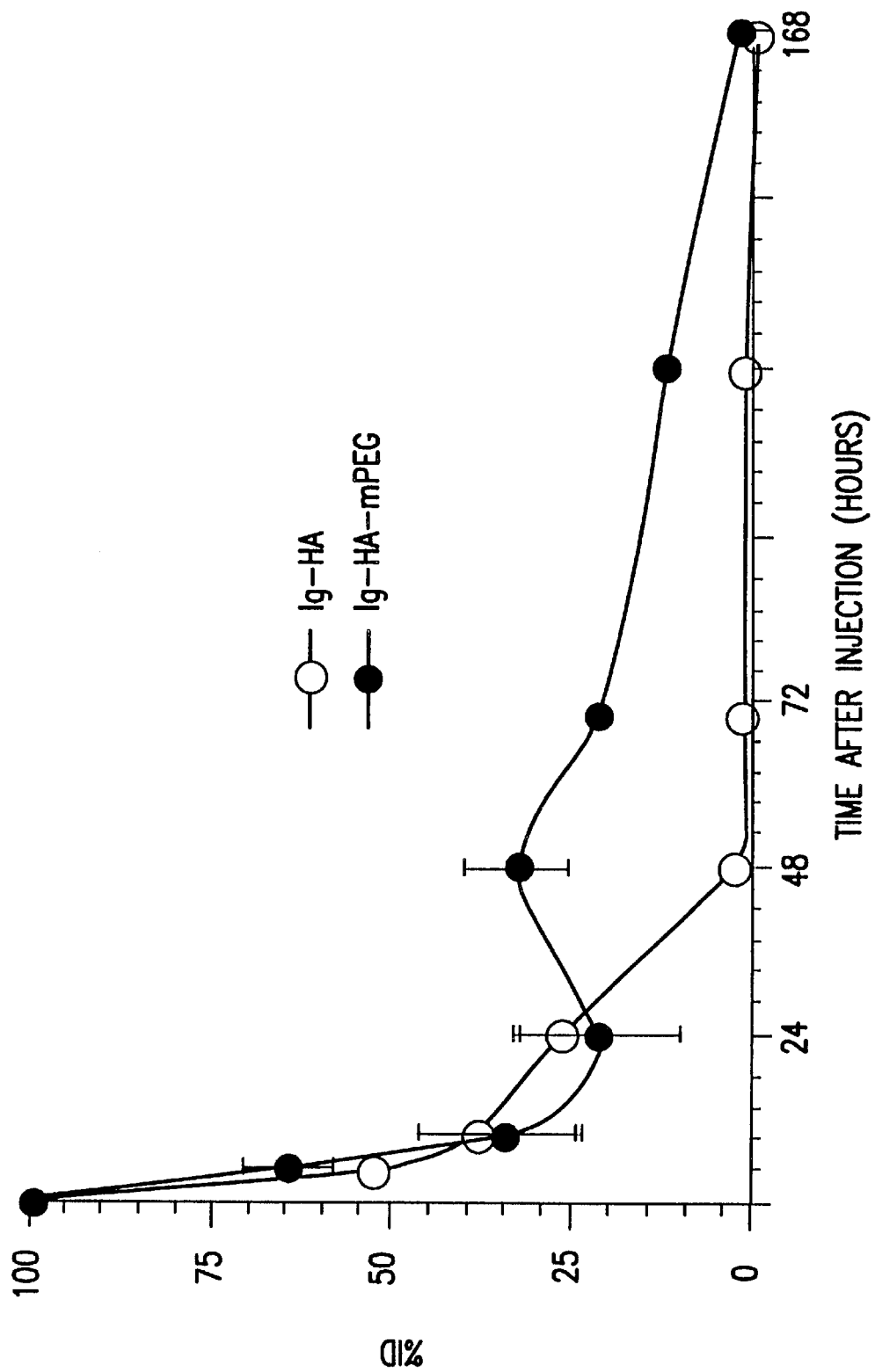

FIG. 12. Blood clearance of native and pegylated Ig-HA. Mice (three per group) were injected i.v. with $^{125}$I-labeled Ig-HA or Ig-HA-mPEG as indicated in Section 9.1. The mice were rested for 15 minutes to allow uniform distribution of radiolabeled material and then blood samples were collected at various intervals of time. Radioactivity content of total blood volume was estimated and considered as the total radioactivity injected (TRI). Blood samples were collected at indicated times and total residual radioactivity (TRR) was estimated. The percent of residual activity was estimated according to the following formula [1-(TRR/TRI)]×100. Each point represents the mean±SD of three mice.

Figure 13:
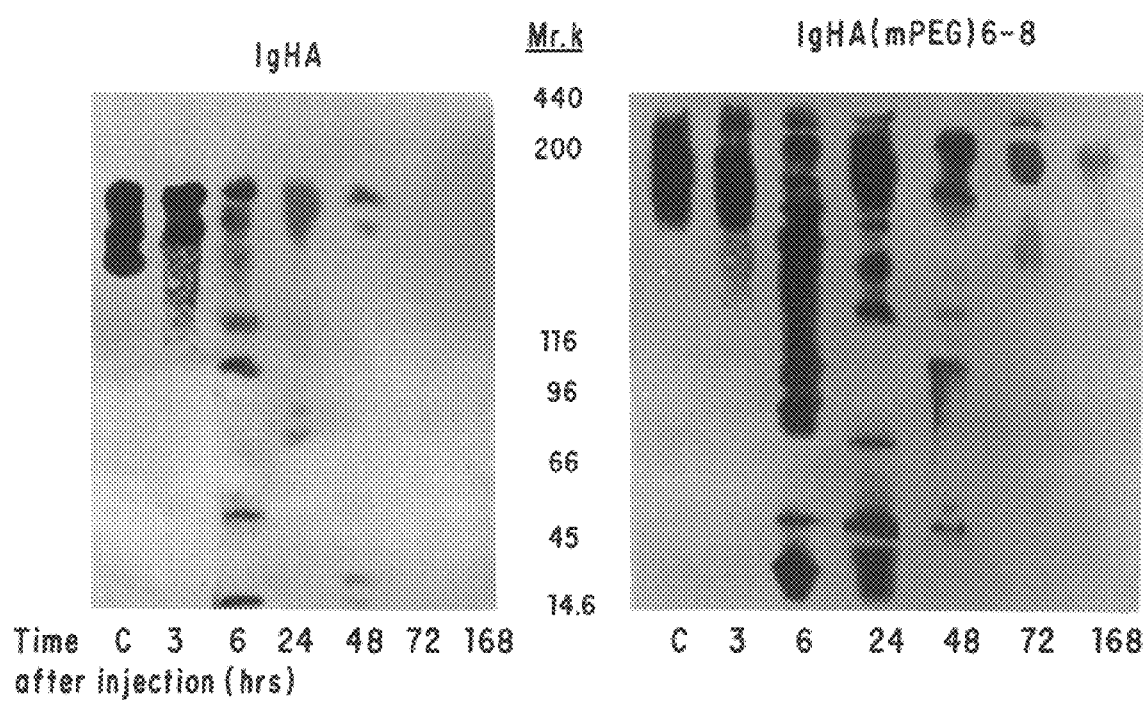
Figure 14A:
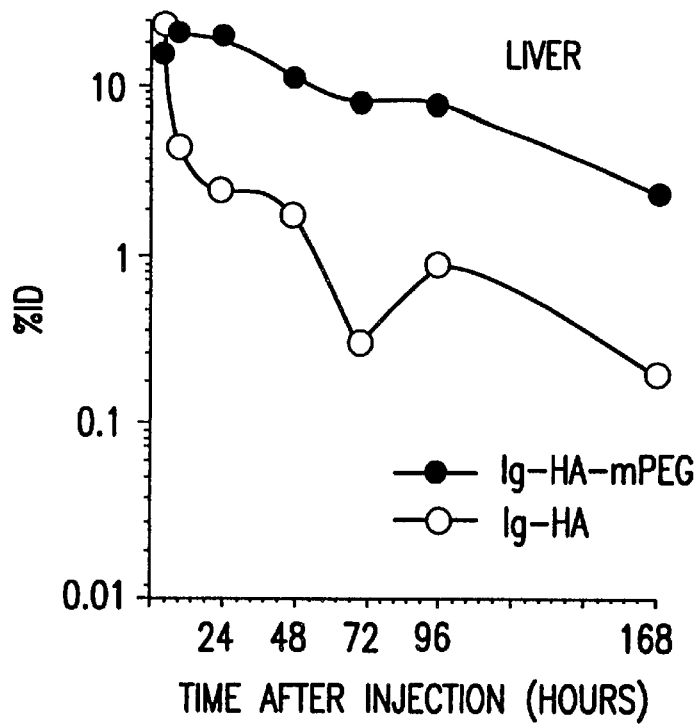
Figure 14B:
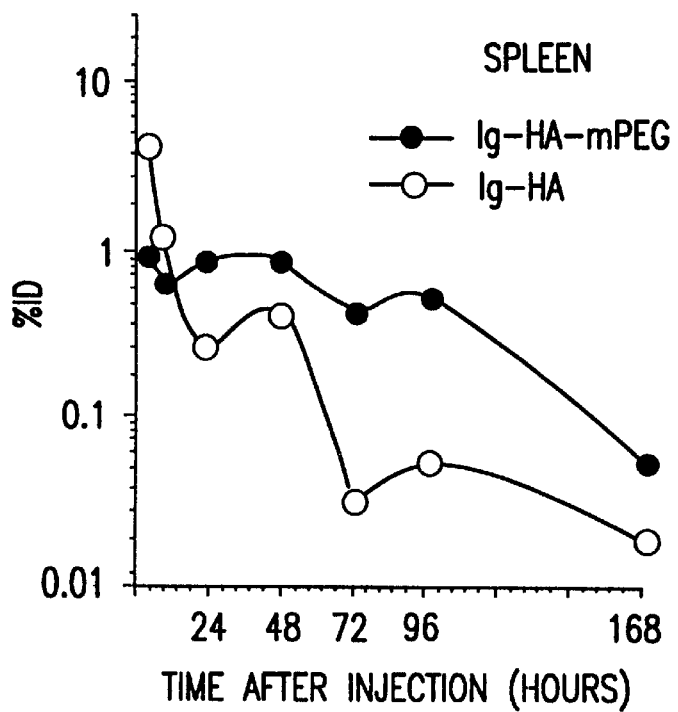
Figure 14C:
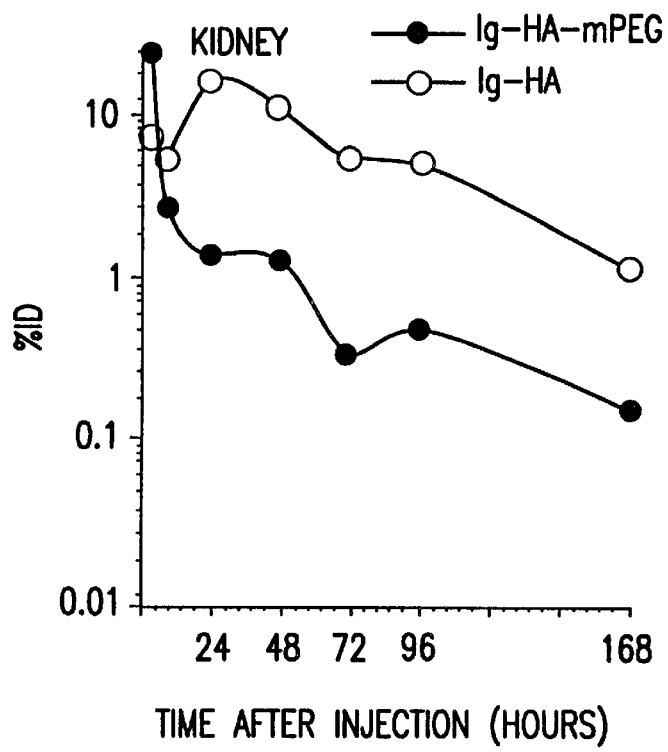
Figure 14D:
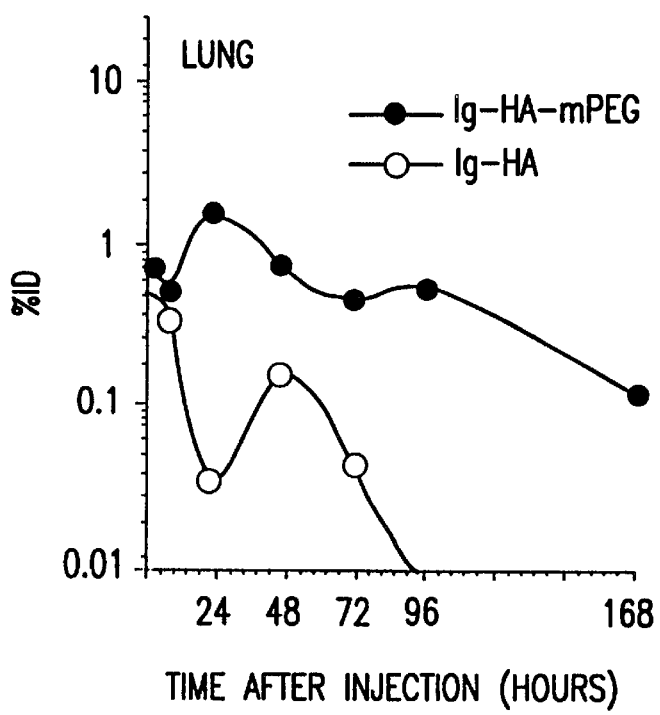

FIG. 13. In vivo proteolysis of native and pegylated Ig-HA. Serum samples from mice injected i.v. with $^{125}$I-labeled Ig-HA or Ig-HA-mPEG (20×10$^6$ cpm/mouse) were collected at indicated times after injection and 5 μl of serum was run on an 8–17% gradient polyacrylamide gel. Separated material was electrotransferred onto PVDF membranes and exposed to Kodak X-OMAT films. Left panel shows the pattern of in vivo degradation over time of samples collected from a mouse injected with Ig-HA. Right panel shows the pattern of in vivo degradation from a mouse injected with Ig-HA-mPEG. Samples of $^{125}$I labeled Ig-HA and Ig-HA-mPEG (5×10$^4$ cpm/5 μl) were analyzed in parallel in the corresponding panel and used as controls (C) of non degraded material prior to inoculation into mice.

FIG. 14. Tissue distribution of native and pegylated Ig-HA. Groups of seven mice each (15–17 g weight) were injected i.v. with $^{125}$I labeled Ig-HA or Ig-HA-mPEG. The mice were rested for 15 min to allow uniform distribution of the labeled material and blood samples were collected. Fragments of visceral organs were then resected at indicated times after injection. Tissue distribution of native or pegylated Ig-HA was estimated as % ID. Each point represents % ID for a mouse corresponding to the indicated time after injection.

FIG. 15. In vitro activation of HA110–120 specific LD1–24 T cell hybridomas by native and pegylated IG-HA. Graded amounts of chromatographically purified Ig-HA, Ig-HA-mPEG and Ig-NP-mPEG were incubated with 2PK3 antigen presenting cells ("APCs"; $10^4$) and LD1–24 T hybridoma cells (2×$10^4$). Activation of LD1–24 T cells was assessed 48 hours later by measuring IL-3 production in supernatant using the IL-3 dependent DA-1 cells (15×$10^4$) and MTT assay. Each point represents the mean of quadruplets plus or minus SD.

FIG. 16. In vivo priming of HA110–120 specific T cells by native and pegylated Ig-HA. Four groups of seven mice each were immunized subcutaneously at the base of the tail and in the foot pads with Ig-HA or IgHA-mPEG in either saline or CFA. Ten days later the draining lymph nodes were collected and cells were cultured for 5 days in standard conditions with graded amounts of various antigens. [$^3$H]-thymidine was added for 18 hours and incorporation was measured. FIGS. 16A and 16B represent the [$^3$H]-thymidine incorporation by lymph node cells from mice immunized with Ig-HA in saline and CFA, respectively. FIGS. 16C and 16D represent the [$^3$H]-thymidine incorporation by lymph node cells from mice immunized with Ig-HA-mPEG in saline and CFA, respectively. In all cases stimulation in vitro was carried out with graded amounts (0.5, 1, 5 and 10 $\mu$g/ml) of Ig-HA, Ig-NP, HA110–120 synthetic peptide, NP147–161 synthetic peptide or UV-inactivated PR8 virus. [$^3$H]-thymidine incorporation upon in vitro stimulation with concanavalin A ("ConA") for three days is also indicated. Each point represents the mean of quadruplet wells plus or minus SD, after subtraction of cpm obtained in the absence of antigen.

FIG. 17. Antibody response of mice immunized with native and pegylated Ig-$V_3$C. Groups of three mice were immunized with either Ig-$V_3$C (open circles) or Ig-$V_3$C-mPEG closed circles), bled at indicated intervals of time and the titers of antibodies to $V_3$C peptide (FIGS. 17A, 17B, 17C and 17D) and to human isotypic determinants (FIGS. 17E, 17F, 17G and 17H) were determined. In FIGS. 17A and 17C the mice were immunized subcutaneously with 100 $\mu$g of either Ig-$V_3$C or Ig-$V_3$C-mPEG emulsified in CFA and boosted two weeks later with 50 $\mu$g of antigens in Incomplete Freund's adjuvant (IFA). Arrows indicate the days of immunization. The other protocols of immunizations were performed with either three injections i.p. of 100 $\mu$g of antigen in saline at seven day intervals (in FIGS. 17B and 17F), or two injections i.p. of 100 $\mu$g of antigens in saline at seven day intervals (in FIGS. 17C and 17G), or a single injection i.p. of 100 $\mu$g of antigens in saline (in FIGS. 17D and 17H). The antibody titers were determined by RIA. Each point represents the mean plus or minus S.D. of three mice.

FIG. 18. Separation of Ig-HA-mPEG conjugates from unpegylated Ig-HA by HPLC on Q300 anion exchange column. FIG. 18A shows the elution profile of the material collected from peak 1 in FIG. 21 and loaded onto the Q300 column. FIG. 18B shows a control elution profile of a preparation of unpegylated Ig-HA.

FIG. 19. Detection of residual mPEG in AIgs-mPEG preparations by electrophoresis on Titan agarose Gel. Samples collected at various steps of purification were run on duplicate Titan gels and either stained with Coomassie/Ponceau (R250) or precipitated with TCA. Lane 1, IgHA-mPEG conjugate after purification on anion-exchange HPLC; lane 2, unpegylated IgHA; lane 3, mPEG 5,000 (4×$10^{-4}$ M); lane 4, IgHA-mPEG conjugate after first step of purification by gel filtration on AcA44 (not done in Coomassie staining).

FIG. 20. Analysis of homogeneity of AIg-mPEG preparations by SDS-PAGE. Samples collected subsequent to purification on anion-exchange HPLC were analyzed on 4–15% polyacrylamide gradient PhastGels (Pharmacia) under non-reducing conditions. Lanes 1 and 4, unpegylated Ig-HA and Ig-$V_3$C, respectively; lanes 2 and 4, Ig-HA-mPEG and Ig-$V_3$C-mPEG, respectively (content of peak 2 in FIG. 19); and lanes 3 and 6 highly derivatized Ig-HA and Ig-$V_3$C (content of peak 1 in FIG. 19).

FIG. 21. Removal of hydrolyzed mPEG from AIg-mPEG preparation by size exclusion chromatography. AcA44 Ultrogel column (80×1.6 cm) was calibrated at 0.4 ml/min flow rate with molecular weight markers (Pharmacia, LKB) and then loaded with 10 mg of IgHA-mPEG preparation. The column was equilibrated with either 0.1 M $NH_4HCO_3$ (as shown in FIG. 21A) or PBS (as shown in FIG. 21B). The peak labeled 1 contained the conjugates and peak 2 corresponds to free mPEG. A plus sign indicates the presence of free polymer as detected by Nessler's test.

5. DETAILED DESCRIPTION OF THE INVENTION

For clarity of presentation, and not by way of limitation, the detailed description of the invention is divided into the following subsections:

(1) B cell epitopes;

(2) T cell epitopes;

(3) antigen binding sites;

(4) engineering of immunoglobulin molecules;

(5) chimeric antibodies;

(6) replacement of a CDR loop of an immunoglobulin with an epitope; and (7) uses of antibodies of the invention.

5.1. B Cell Epitopes

The term "B cell epitope", as used herein, refers to a peptide, including a peptide comprised in a larger protein, which is able to bind to an immunoglobulin receptor of a B cell and participate in the induction of antibody production by the B cell.

For example, and not by way of limitation, the hypervariable region 3 loop ("V3 loop") of the envelope protein of human immunodeficiency virus ("HIV") type 1 is known to be a B cell epitope. Although the sequence of this epitope varies, the following consensus sequence, corresponding to residues 301–319 of HIV-1 gp120 protein, has been obtained: Arg-Lys-Ser-Ile-His-Ile-Gly-Pro-Gly-Arg-Ala-Phe-Tyr-Thr-Thr-Gly-Glu-Ile-Ile (SEQ ID NO: 1). Further description of the use of V3 loop peptide in the context of the present invention is set forth below.

Other examples of known B cell epitopes which may be used according to the invention include, but are not limited to, epitopes associated with influenza virus strains, such as Trp-Leu-Thr-Lys-Lys-Gly-Asp-Ser-Tyr-Pro (SEQ ID NO: 2), which has been shown to be an immunodominant B cell epitope in site B of influenza HA1 hemagglutinin, the epitope Trp-Leu-Thr-Lys-Ser-Gly-Ser-Thr-Tyr-Pro (SEQ ID NO: 3) (H3), and the epitope Trp-Leu-Thr-Lys-Glu-Gly-Ser-Asp-Tyr-Pro (SEQ ID NO: 4) (H2) (Li et al., 1992, J. Virol. 66:399–404); an epitope of F protein of measles virus (residues 404–414; Ile-Asn-Gln-Asp-Pro-Asp-Lys-Ile-Leu-Thr-Tyr (SEQ ID NO: 5); Parlidos et al., 1992, Eur. J. Immunol. 22:2675–2680); an epitope of hepatitis virus pre-Sl region, from residues 132–145 (Leclerc, 1991, J. Immunol. 147:3545–3552); and an epitope of foot and mouth disease VP1 protein, residues 141–160, Met-Asn-Ser-Ala-Pro-Asn-Leu-Arg-Gly-Asp-Leu-Gln-Lys-Val-Ala-Arg-Thr-Leu-Pro (SEQ ID NO: 6) (Clarke et al., 1987, Nature 330:381–384).

Still further B cell epitopes which may be used are known or may be identified by methods known in the art, as set forth in Caton et al., 1982, Cell 31:417–427.

5.2. T Cell Epitopes

The term "T cell epitope", as used herein, refers to a peptide, including a peptide comprised in a larger protein, which is associated with MHC self antigens and recognized by a T cell and which functionally activates the T cell.

For example, a $T_h$ epitope is recognized by a helper T cell and promotes the facilitation of B cell antibody production via the $T_h$ cell. Such epitopes are believed to arise when antigen presenting cells ("APCs") have taken up and degraded a foreign protein. The peptide products of degradation, which include the $T_h$ epitope, appear on the surface of the APC in association with MHC class II antigens.

Further, a CTL epitope is recognized by a cytotoxic T cell; when the CTL recognizes the CTL epitope on the surface of a cell, the CTL may induce lysis of the cell. CTL epitopes are believed to arise when an APC has synthesized a protein which is then processed in the cell's cytoplasmic compartment, leading to the generation of peptides (including the CTL epitope) which associate with MHC class I antigens on the surface of the APC and are recognized by $CD8^+$ cells, including CTL.

For example, and not by way of limitation, influenza A hemagglutinin (HA) protein bears, at amino acid residues 110–120, a $T_h$ epitope having the amino acid sequence Ser-Phe-Glu-Arg-Phe-Glu-Ile-Phe-Pro-Lys-Glu (SEQ ID NO: 7).

Other examples of known T cell epitopes include, but are not limited to, two promiscuous epitopes of tetanus toxoid, Asn-Ser-Val-Asp-Asp-Ala-Leu-Ile-Asn-Ser-Thr-Lys-Ile-Tyr-Ser-Tyr-Phe-Pro-Ser-Val (SEQ ID NO: 8) and Pro-Glu-Ile-Asn-Gly-Lys-Ala-Ile-His-Leu-Val-Asn-Asn-Glu-Ser-Ser-Glu (SEQ ID NO: 9) (Ho et al., 1990, Eur. J. Immunol. 20:477–483); an epitope of cytochrome c, from residues 88–103, Ala-Asn-Glu-Arg-Ala-Asp-Leu-Ile-Ala-Tyr-Leu-Gln-Ala-Thr-Lys (SEQ ID NO: 10); an epitope of Mycobacteria heatshock protein, residues 350–369, Asp-Gln-Val-His-Phe-Gln-Pro-Leu-Pro-Pro-Ala-Val-Val-Lys-Leu-Ser-Asp-Ala-Leu-Ile (SEQ ID NO: 11) (Vordermir et al., Eur. J. Immunol. 24:2061–2067); an epitope of hen egg white lysozyme, residues 48–61, Asp-Gly-Ser-Thr-Asp-Tyr-Gly-Ile-Leu-Gln-Ile-Asn-Ser-Arg (SEQ ID NO: 12) (Neilson et al., 1992, Proc. Natl. Acad. Sci. U.S.A. 89: 7380–7383; an epitope of Streptococcus A M protein, residues 308–319, Gln-Val-Glu-Lys-Ala-Leu-Glu-Glu-Ala-Asn-Ser-Lys (SEQ ID NO: 13) (Rossiter et al., 1994, Eur. J. Immunol. 24:1244–1247); and an epitope of Staphylococcus nuclease protein, residues 81–100, Arg-Thr-Asp-Lys-Tyr-Gly-Arg-Gly-Leu-Ala-Tyr-Ile-Tyr-Ala-Asp-Gly-Lys-Met-Val-Asn (SEQ ID NO: 14) (de Magistris, 1992, Cell 68:1–20). Still further $T_h$ epitopes which may be used are known or may be identified by methods known in the art.

As another example, and not by way of limitation, PR8 influenza virus nucleoprotein bears, at amino acid residues 147–161, a CTL epitope having the amino acid sequence Thr-Tyr-Gln-Arg-Thr-Arg-Ala-Leu-Val-Arg-Thr-Gly-Met-Asp-Pro (SEQ ID NO: 15).

Other examples of known CTL epitopes include, but are not limited to, those discussed in Rotzschke et al., 1991, Immunol. Today 12:447–455. Still further CTL epitopes which may be used are known or may be identified by methods known in the art.

5.3. Antigen Binding Sites

The term "antigen binding site", as used herein, refers to a receptor-like molecule, or a portion thereof, which is capable of binding to a second molecule, the antigen. For example, but not by way of limitation, the receptor-like molecule may preferably be an immunoglobulin molecule, and the antigen binding site may reside in the variable region of the molecule. In alternate embodiments, however, the receptor-like molecule may be a T cell receptor or other cell-surface receptor molecule, such as an Fc receptor, a complement receptor, a cytokine receptor, etc.

In certain embodiments of the invention, the antigen is an antigen expressed by a pathogen, such as a viral, protozoan, mycoplasmal, fungal or bacterial antigen. For example, and not by way of limitation, such antigens may be HIV gp120 protein, hepatitis B virus surface antigen, influenza virus hemagglutinin proteins, measles virus, poliovirus and rhinovirus antigens, etc.

In alternate embodiments of the invention, the antigen is a tumor specific antigen.

In additional embodiments, the antigen is a portion of an antibody molecule which comprises the combined antigenic determinants (idiotopes) that are directed at a particular second antigen. In such cases, the antigen binding site is functionally similar to an anti-idiotype antibody. It is well known that anti-idiotype antibodies carrying the internal image of microbial antigens as well as antibodies against TCR of T cells can stimulate humoral and cellular antimicrobial immunity.

In still further embodiments, the antigen is a cell surface antigen. For example, the antigen may be CD3, a protein associated with the T cell receptor (TCR) of CTL. Binding of antibody to CD3 on CTL may activate the CTL, thereby effecting non-specific cell lysis.

5.4. Engineering of Immunoglobulin Molecules

According to the invention, a B cell epitope, T cell epitope, or antigen binding site, or more than one of such elements, may be inserted into an immunoglobulin molecule (termed the "parent immunoglobulin molecule"). The molecule resulting from the insertion is termed a "chimeric immunoglobulin molecule", which may be incorporated into an antibody of the invention. The term "chimeric", as used herein, refers to a molecule which has been engineered to link together segments of nucleic acid or protein which are not typically linked together in nature. The two segments may originate from the same, or from different, species of organism. For example, it may be particularly advantageous to link together segments, all of which are derived from humans, so as to produce an entirely human chimeric antibody.

Such insertion may preferably be accomplished by replacing a segment of the gene encoding the parent immunoglobulin molecule with nucleic acid encoding the desired epitope or antigen binding site at a region of the nucleic acid encoding the parent immunoglobulin molecule which is not essential for expression or for function of the parent immunoglobulin protein molecule (but which may abolish its original specificity) and which will position the epitope or antigen binding site such that the biological function of the inserted peptide sequence (as either an epitope or antigen-binding site) may be retained. Such retention need not be complete; the function of the inserted peptide may be either enhanced or diminished relative to the natural peptide, but its activity cannot be eliminated completely.

Replacement of a segment of the gene, and consequent replacement of a segment of its encoded immunoglobulin molecule, is advantageous as compared to the addition of segments, because the addition of segments is associated with a limit to the length of segments which may be added. This is because if a long peptide is added, its insertion may not allow for proper folding of the immunoglobulin molecule and proper assembly with its partner immunoglobulin chain. Improperly folded molecules are frequently degraded rather than excreted. Furthermore, insertion of new amino acids, for example, but not by limitation, in the creation of a restriction endonuclease cleavage site, may create new, undesirable epitopes and thereby induce the formation of undesirable antibodies.

The nucleic acid encoding the parent immunoglobulin molecule may be DNA or RNA, and may be comprised in a vector molecule.

The identification of an appropriate insertion site in the parent immunoglobulin molecule includes at least two considerations. The first involves a determination of which regions of the parent immunoglobulin molecule are necessarily or desirably retained. For example, it may be desirable to maintain basic antibody structure, and to retain the constant regions of the molecule, in which case it may be particularly desirable to insert the epitope or antigen-binding site into a hypervariable region (CDR; see for example, section 5.6, infra). Further, it is undesirable to insert sequence encoding the epitope or antigen binding site into a region of the nucleic acid encoding the parent immunoglobulin molecule which is important for efficient transcription or translation or which is not transcribed into RNA or not translated into protein. It may not be necessary, however, for the antigen-binding specificity of the parent immunoglobulin to be retained; to the contrary, it may be desirable that such antigen-binding capability be lost, as loss of this capability may be indicative or consequent to the insertion of epitope or new antigen-binding sequence.

The second consideration relates to the functional activity of the inserted epitope or antigen binding site. Preferably the epitope or antigen-binding site is inserted so as to be positioned at a superficial location (i.e., an exposed area) on the chimeric immunoglobulin molecule, such that it is capable of interacting with a B cell or T cell or of binding to an antigen.

The epitope or antigen binding site (or more than one of such elements) may be inserted into the parent immunoglobulin molecule by any method known in the art. Preferably, nucleic acid encoding the epitope or antigen binding site may be inserted into the nucleic acid encoding the parent immunoglobulin molecule in such a manner that a portion of immunoglobulin-encoding sequence is replaced by the nucleic acid sequence encoding the epitope or antigen binding site. By replacing a portion of the sequence, the overall configuration of the immunoglobulin molecule may be minimally disturbed. In contrast, the addition of inserted sequences would be expected to distort the geometry of the immunoglobulin molecule; as the size or hydrophobicity/hydrophilicity of the inserted sequence increases, such effects may become problematic.

Most preferably, the nucleic acid encoding the epitope or antigen binding site is inserted into the immunoglobulin-encoding nucleic acid by polymerase chain reaction ("PCR") techniques.

Nucleic acid engineered to encode a chimeric immunoglobulin molecule according to the invention may be cloned using standard techniques. Detailed DNA cloning methods, exemplary of standard laboratory techniques, are provided in a variety of sources. See e.g. Sambrook et al., "Molecular Cloning A Laboratory Manual", Cold Spring Harbor Laboratory Press, NY (1989). Specific, nonlimiting examples of the preparation of nucleic acids encoding particular chimeric immunoglobulin molecules are set forth below.

Once the nucleic acid encoding a chimeric immunoglobulin molecule has been cloned, it may be introduced into a suitable host for expression of the encoded protein. The cloned nucleic acid may be first inserted into an appropriate expression vector or may be transfected into the cell as linear DNA for recombination with the host genome. Suitable expression vectors include but are not limited to plasmids, viruses and retroviruses. Choice of a suitable vector will be determined in part on the choice of the host used for protein expression.

Suitable hosts include but are not limited to bacteria, mammalian cell lines, whole animals such as transgenic mice and insect cell lines. Insect cell lines are less expensive to maintain and produce more protein compared to mammalian cell lines and are thus more suitable to large-scale protein production. Genes expressed by insect cell lines do not contain exons therefore the exons should be excised from nucleic acid encoding chimeric immunoglobulin molecules prior to their expression in insect cell lines. Excision is relatively straightforward and can be accomplished for instance directly by oligonucleotide directed site-specific mutagenesis or indirectly by cDNA cloning.

Transfer of the gene into the host can be done by any of the well known means in the art. For example, methods of gene transfer include but are not limited to $CaCl_2$ mediated transfection in the case of bacteria and in the case of eukaryotic cells, $CAPO_4$ mediated transfection, viral infection including retroviral latent infection, electroporation, liposome mediated DNA transfer and microinjection among others.

Any suitable method of purifying proteins produced by the host may be used in the practice of the present invention.

See e.g. Webb et al., "Cell-surface Expression and Purification of Human CD4 Produced in Baculovirus-infected Insect Cells", Proc. Natl. Acad. Sci. USA, 85:7731–7735 (1989); and Moran et al., "Characterization of Variable-Region Genes and Shared Crossreactive Idiotypes of Antibodies Specific for Antigens of Various Influenza Viruses", Vir. Immunol., 1:1–12 (1987).

In preferred embodiments of the invention, the chimeric immunoglobulin of the invention has a Y shaped base portion which is the same as some or all of the constant regions of human immunoglobulin. This use of human immunoglobulin avoids the problem of the modified immunoglobulin being recognized as a foreign species itself, and thus facilitates its use in human therapy. Additionally the base portion may confer effector functions on the molecule such as in vivo stability, Fc receptor binding, protein A binding, complement fixation, and placental transfer (in the case of IgG). It will thus be understood that modified sequences based on immunoglobulin molecules are within the scope of the present invention so long as the modification does not give rise to immune rejection problems.

For example, and not by way of limitation, the following general method may be used. The nucleic acid sequence encoding the epitope or antigen binding site may be analyzed to search for and identify a restriction enzyme (referred to as "enzyme A") which cleaves at one site in the nucleic acid sequence. If no such site is present, one may be engineered into the sequence; however, it should be noted that it is preferable not to add nucleic acid sequence, in that such addition may, as set forth above, distort the conformation of the encoded immunoglobulin molecule. Four PCR primers may then be prepared. The first PCR primer (termed "P1") may be essentially complementary to the sense strand of the nucleic acid encoding the parent immunoglobulin molecule. The second PCR primer (termed "P2") may be complementary to the antisense strand of the nucleic acid encoding the parent immunoglobulin molecule, but may further comprise, at its 5' end, a portion of the nucleic acid encoding the epitope or antigen-binding site to be inserted, which portion is in frame and spans the cleavage site for enzyme A and which replaces a portion of the parent immunoglobulin-encoding nucleic acid of similar size. The third PCR primer (termed "P3") may be essentially complementary to the antisense strand of the nucleic acid encoding the parent immunoglobulin molecule. The fourth PCR primer (termed "P4") may be complementary to the sense strand of the nucleic acid encoding the parent strand of the nucleic acid encoding the parent immunoglobulin molecule, but may further comprise, at its 5' end, a portion of the nucleic acid encoding the epitope or antigen binding site to be inserted, which portion is in frame and spans the cleavage site for enzyme A, and which replaces a portion of the parent immunoglobulin-encoding nucleic acid of similar size. The portions of nucleic acid sequence encoding epitope or antigen-binding site in P2 and P4 taken together contain the entire sequence encoding the epitope or antigen binding site to be inserted. P1 and P3 may be positioned on opposite sides of the designated insertion site. P1 and P2 primers may then be used in PCR to produce a fragment X. P3 and P4 primers may be used in PCR to produce a fragment Y. The resulting fragments may then be cleaved by enzyme A, and then fragments X and Y can be ligated together.

The ligated fragment XY may then be inserted, in the context of nucleic acid encoding appropriate regions of the parent immunoglobulin molecule, into a suitable vector, which may then be used to express chimeric immunoglobulin molecule, using standard techniques. If the chimeric immunoglobulin molecule is a heavy chain molecule, it is preferably expressed in a cell concurrently with the expression of a compatible light chain immunoglobulin molecule. For example, if the parent immunoglobulin is a heavy chain known to form a functional antibody with a particular light chain, the chimeric immunoglobulin is preferably expressed together with that light chain. A particularly preferred cell for expression of chimeric immunoglobulin is a non-secreting myeloma cell line, such as the BALB/c SP2/0 cell line, which may be obtained from the American Type Culture Collection, where the cell line is designated "SP2/0-Ag14", assigned the accession number ATCC CRL 1581.

Figure 1A:
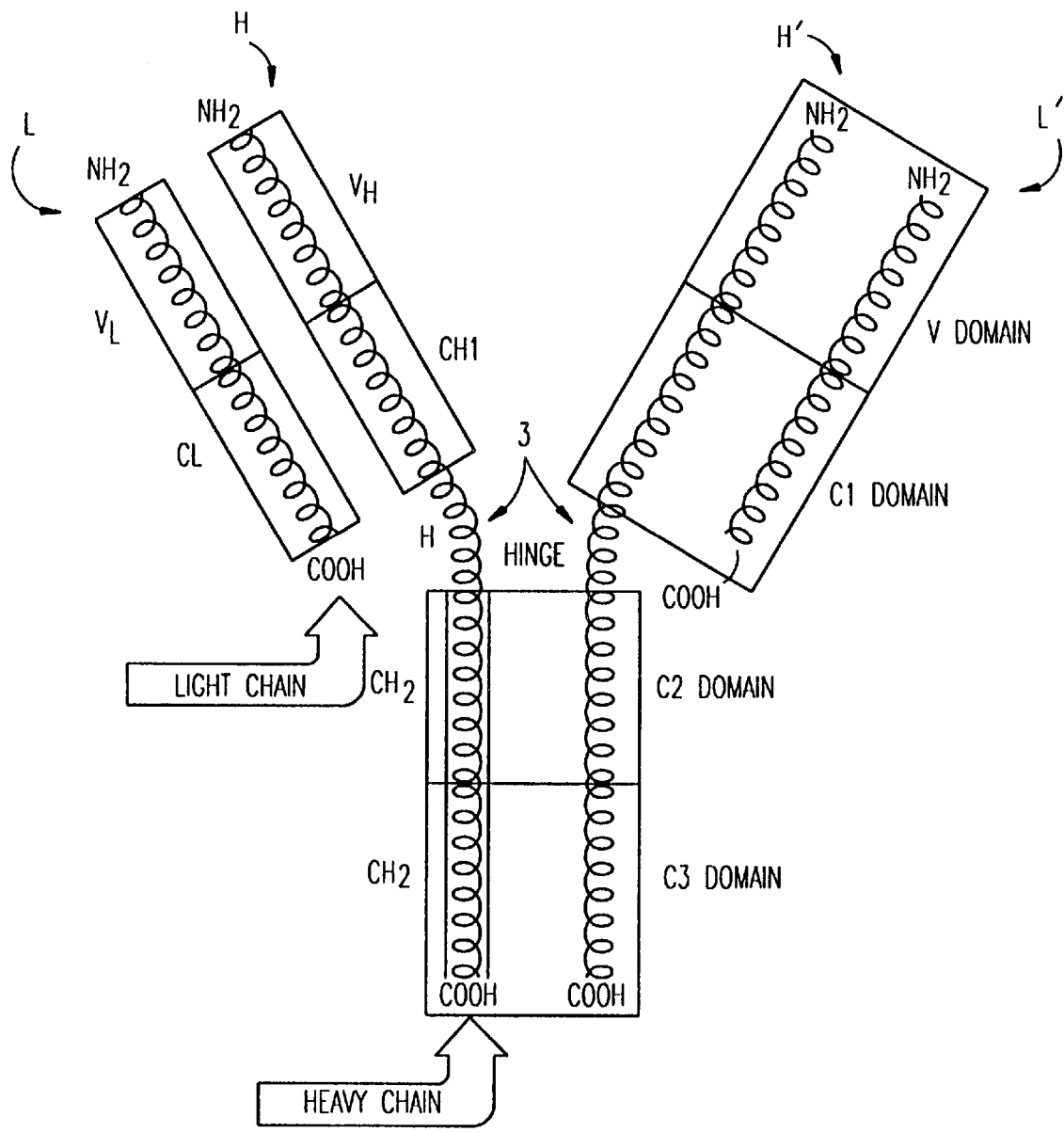
FIG. 1A is an illustration of an immunoglobulin molecule illustrating its Y shape, combining sites, hinge regions, light and heavy chains and their corresponding variable and constant domains.
Figure 1B:
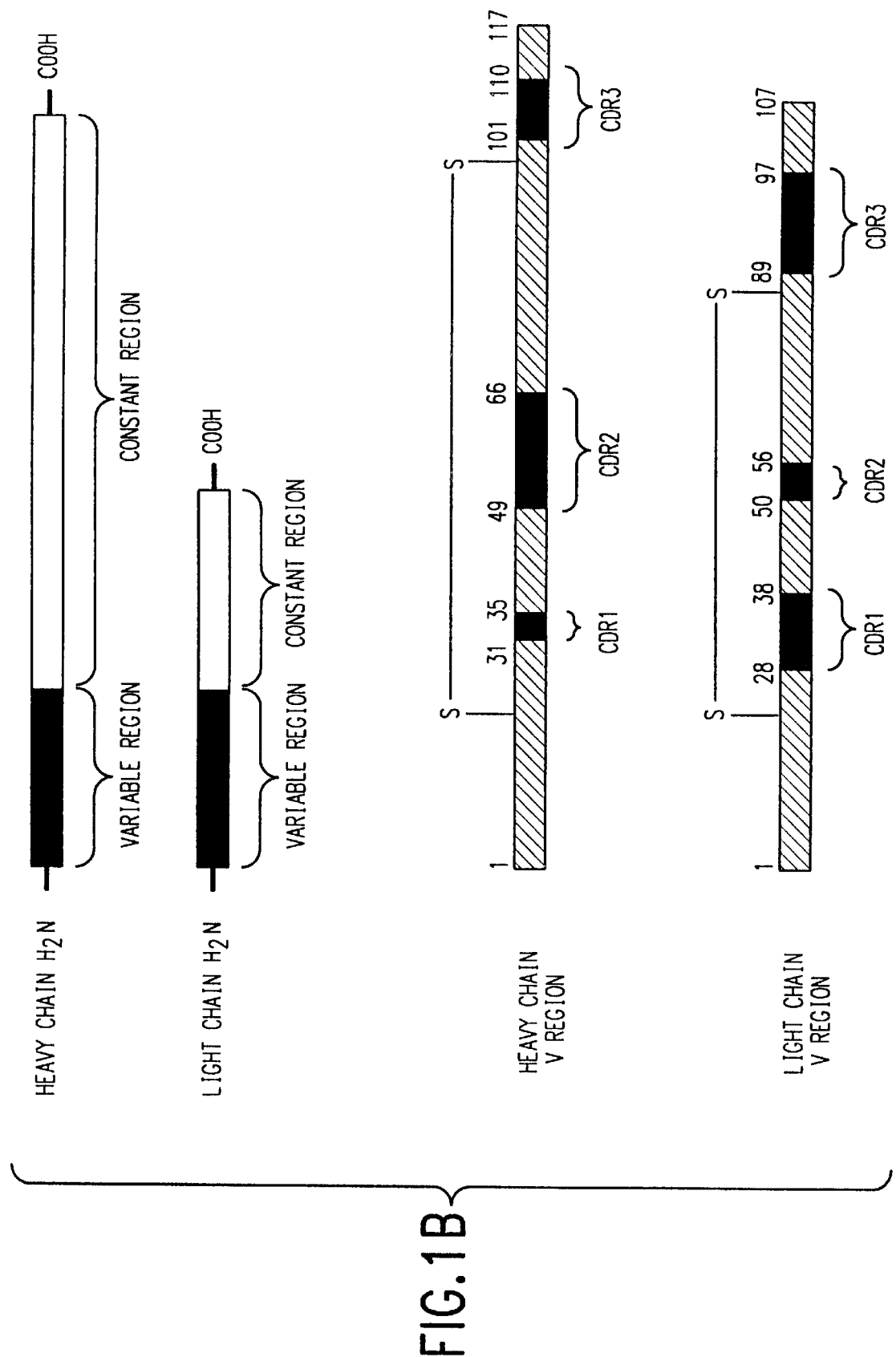
FIG. 1B depicts the location of variable and hypervariable (CDR) regions in light and heavy immunoglobulin chains. The numbers indicate typical amino acid positions, and S—S indicates a disulfide bridge.
Figure 1C:
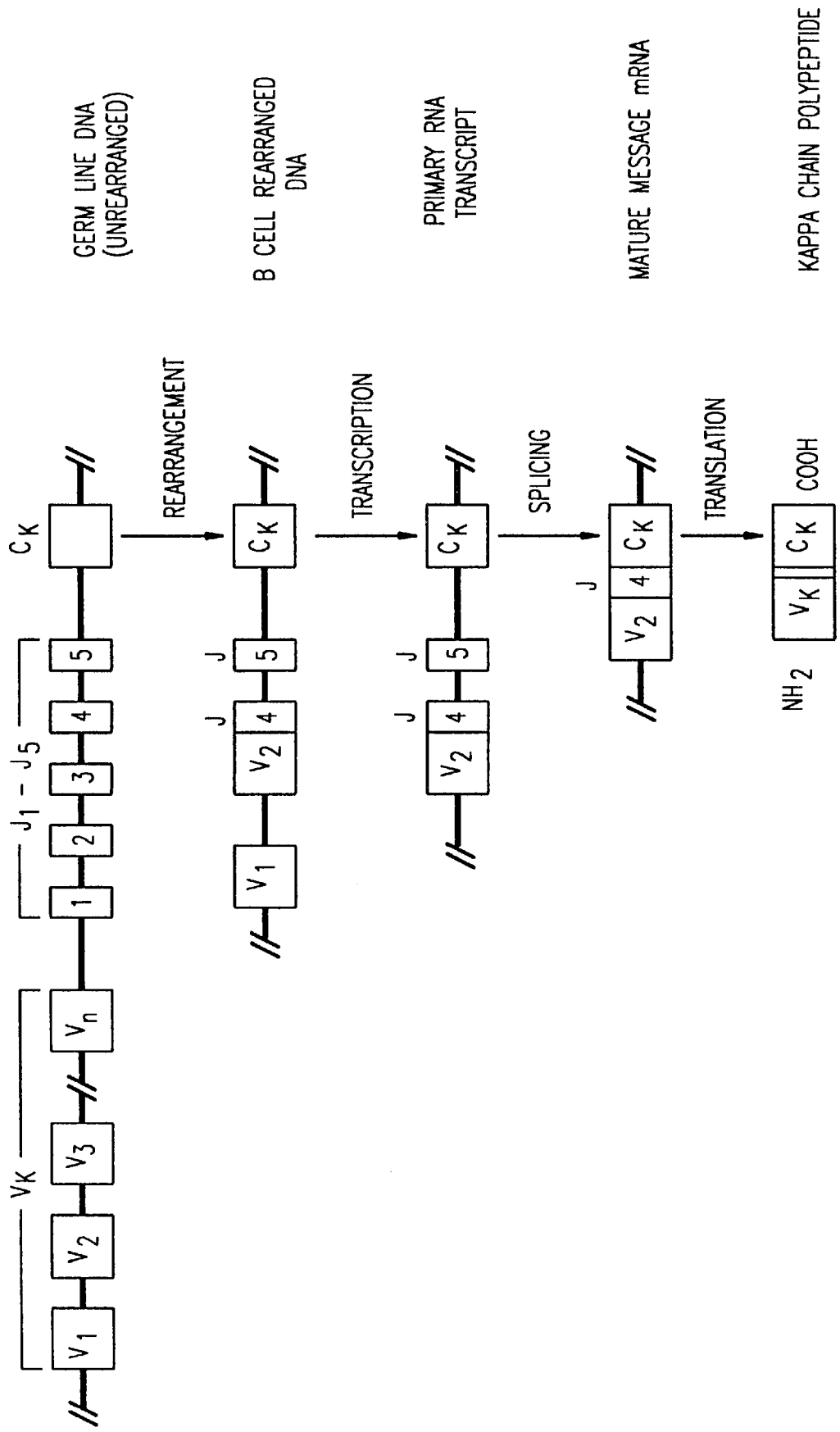
FIG. 1C is an illustration of immunoglobulin kappa light chain gene structure.
Figure 1D:
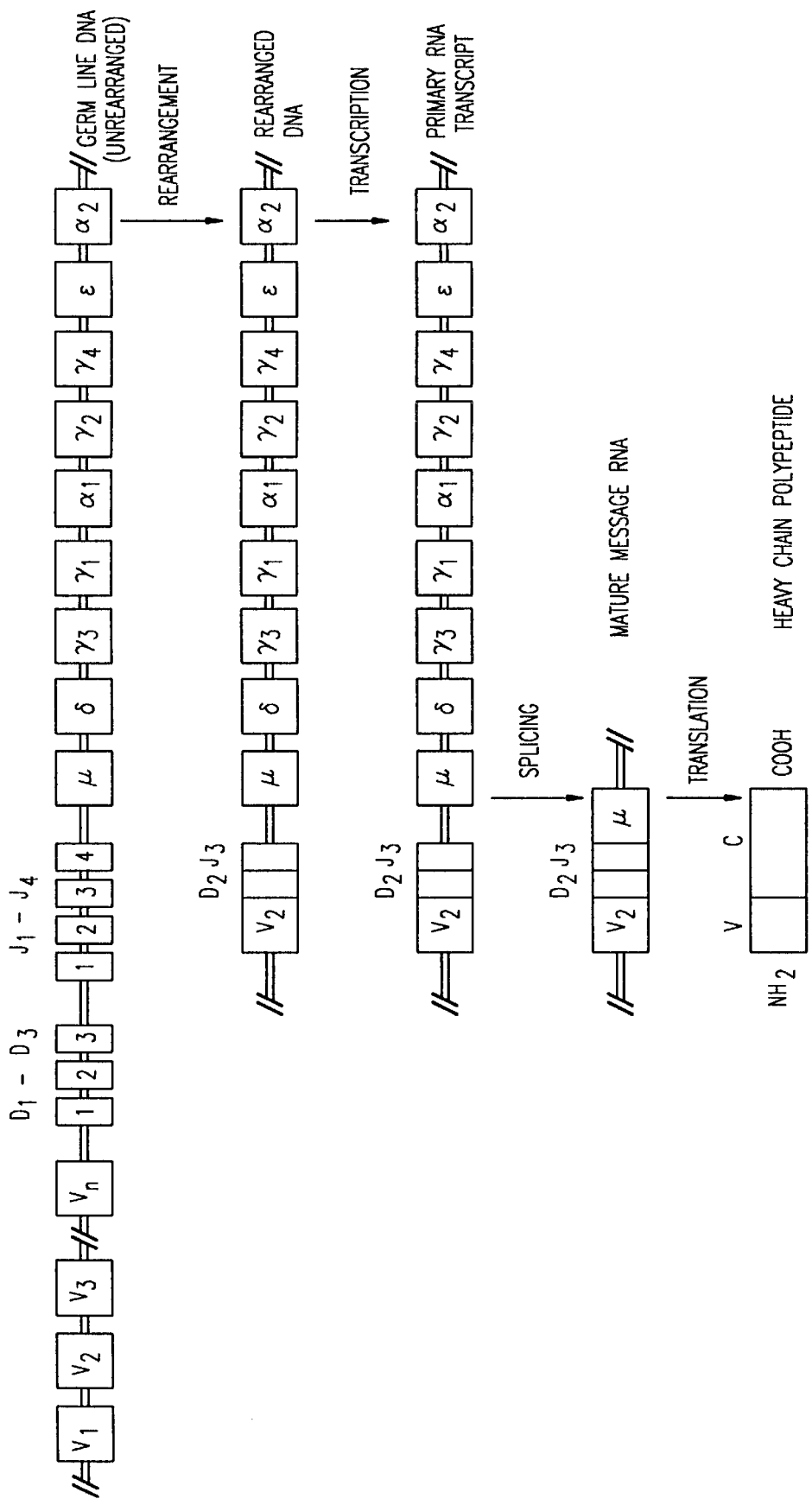
FIG. 1D is an illustration of immunoglobulin heavy chain gene structure.
Figure 2:
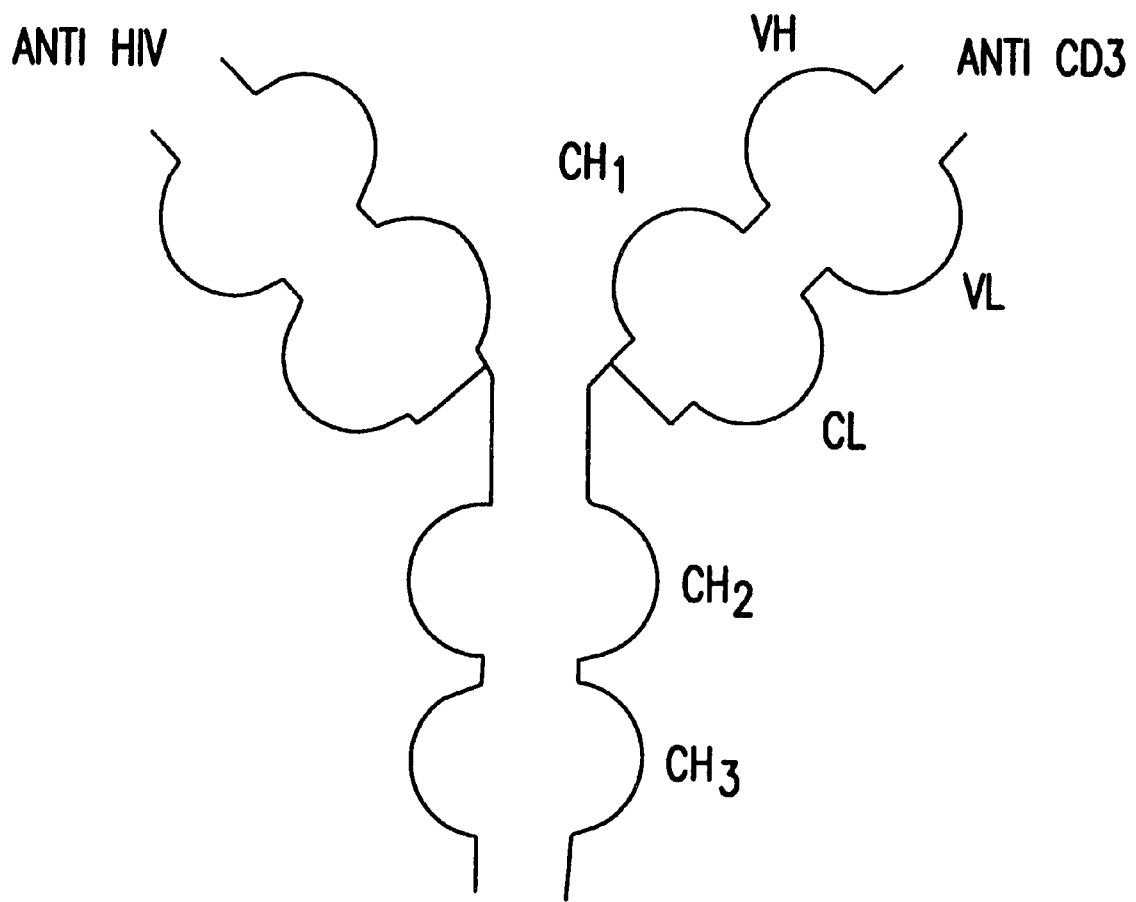
FIG. 2 is an illustration of a protein complex containing a single immunoglobulin combining site capable of recognizing a virus, virus infected cell or viral antigen, a single immunoglobulin combining site capable of recognizing and binding to CDR3 so as to activate CTL, and an immunoglobulin hinge region separating the combining sites from the immunoglobulin constant domain CH2 and CH3 regions.
Figure 3:
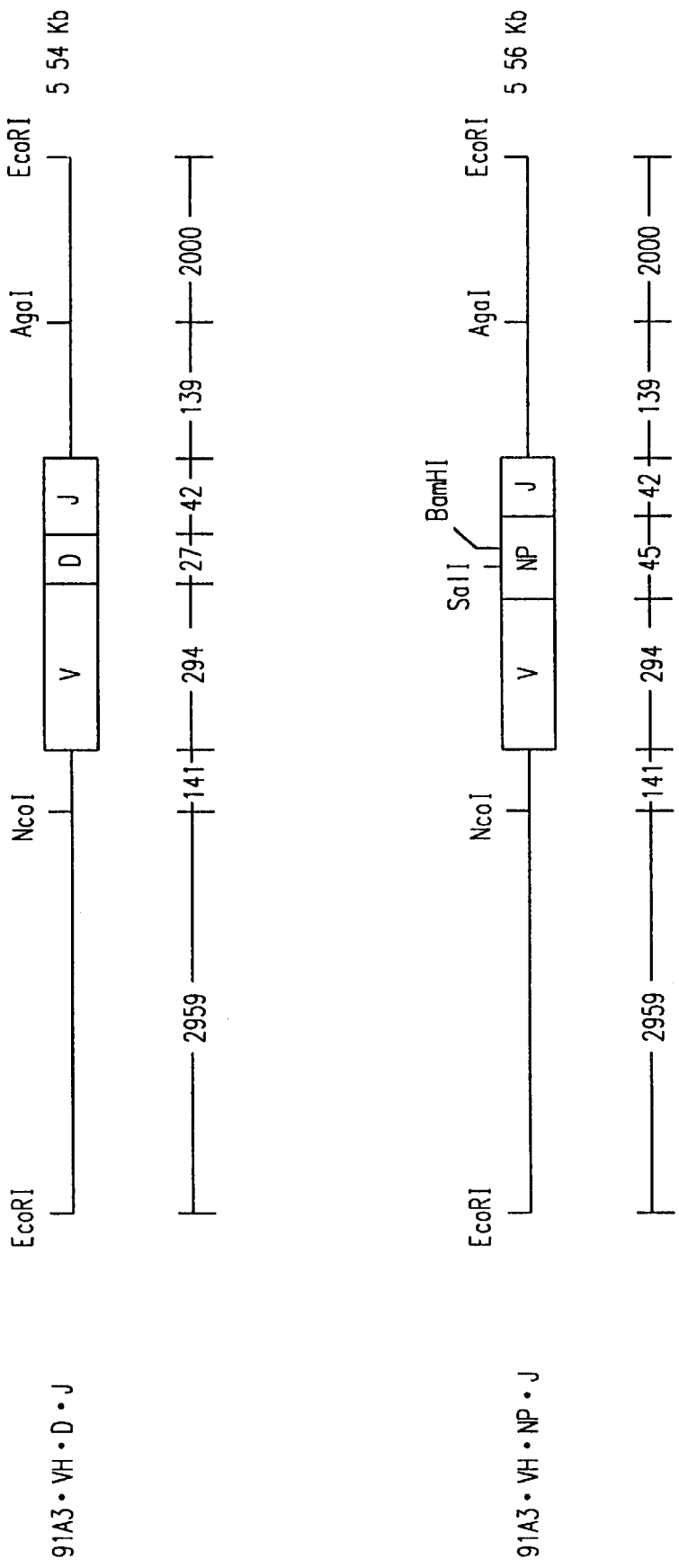
FIG. 3 is a schematic diagram of a DNA construct containing the VH-D-J gene.

In Example Sections 6, 7 and 8 provided below, two DNA expression vectors, pSV2gpt-91A3VH-CIgG2b and pSV2neo-91A3L, were utilized, which carry, respectively, a heavy and a light chain gene of an anti-arsonate antibody called 91A3. The pSV2gpt-91A3VH-CIgG2b carries an IgG2b constant region gene inserted in the HindIII restriction endonuclease site of the vector and a 5.5 kb DNA segment containing the rearranged VHDJ gene of the heavy chain of the 91A3 antibody inserted in the EcoRI restriction endonuclease site as shown in FIG. 3. The 5.5 kb fragment also contains the heavy chain Ig promoter and enhancer. The pSV2neo-91A3L carries the rearranged VL and CL genes and the necessary regulatory elements inserted into the EcoRI and BamHI restriction endonuclease sites.

It has now been shown that cotransfection of these vectors into the nonsecreting myeloma cell line, SP2/0 leads to the expression of a functional 91A3 antibody. This antibody derives its VH from the J558 family and its D segment is probably involved in antigen binding. These observations suggest that these D segments are surface exposed. In fact, the hydrophilicity profile of the 91A3 VH also predicts that its D segment is surface exposed. For these reasons the 91A3VHDJ was chosen to construct a chimeric immunoglobulin carrying various foreign epitopes, including a CD8 epitope from influenza virus nucleoprotein, a CD4 epitope from influenza virus hemagglutinin, and B cell epitopes from HIV-1 or influenza viruses.

In Example Section 7, below, the D segment of the heavy chain of the 91A3 antibody was replaced by influenza virus nucleoprotein (NP) epitope which is capable of being recognized by CTL cells. The 9 amino acid D segment of the heavy chain of the 91A3 antibody was replaced with a 15 amino acid NP CTL epitope as illustrated in FIG. 3. The NP epitope corresponds to amino acid residues 147–161 within the NP of PR8 virus and is known to induce virus specific CTLs in Balb/C but not C57BL/6 mice.

The construct was expressed in the SP2/0 myeloma cell line, and was recognized by anti-NP antibodies. Such transfected SP2/0 were killed by T cells specific for the NP epitope.

In the influenza system, anti-hemagglutinin ("anti-HA") antibodies play a major protective role since they prevent viral attachment. The anti-HA antibody response is T dependent requiring both helper T cells and B cells. Since the ultimate goal of a vaccine is to induce protective immunity, it may be desirable to produce a chimeric antibody bearing both B and $T_h$ cell epitopes.

A chimeric immunoglobulin molecule carrying a HA $T_h$ epitope was prepared (Zaghouani et al., 1993, Science 259:224–227) using methods analogous to those set forth above. The 5.5 kb DNA fragment encoding the heavy chain variable region ("$V_H$") of the 91A3 antibody was used in PCR mutagenesis (Zaghouani et al., 1992, J. Immunol. 148: 3604) to replace the D segment with a nucleotide sequence encoding a $T_h$ epitope of the HA of PR8 influenza virus. This epitope corresponds to amino acid residues 110 to 120 of HA and is recognized by CD4⁺ T cells in association with I-E$^d$ MHC class II molecules. The mutated VH gene, from which the D segment was deleted and the cognate peptide sequence inserted in the correct frame, was subcloned in a pSV2gpt vector upstream of the exons of the BALB/c gamma 2b constant region from which the MOPC 141 VDJ fragment had been excised. To express this gene with the homologous light chain gene, the vector was transfected into the non-Ig-secreting BALB/c myeloma B cell line SP2/0, together with a pSV2-neo vector carrying the rearranged 91A3 light chain gene. The resulting antibody was termed "Ig-HA".

Figure 5:
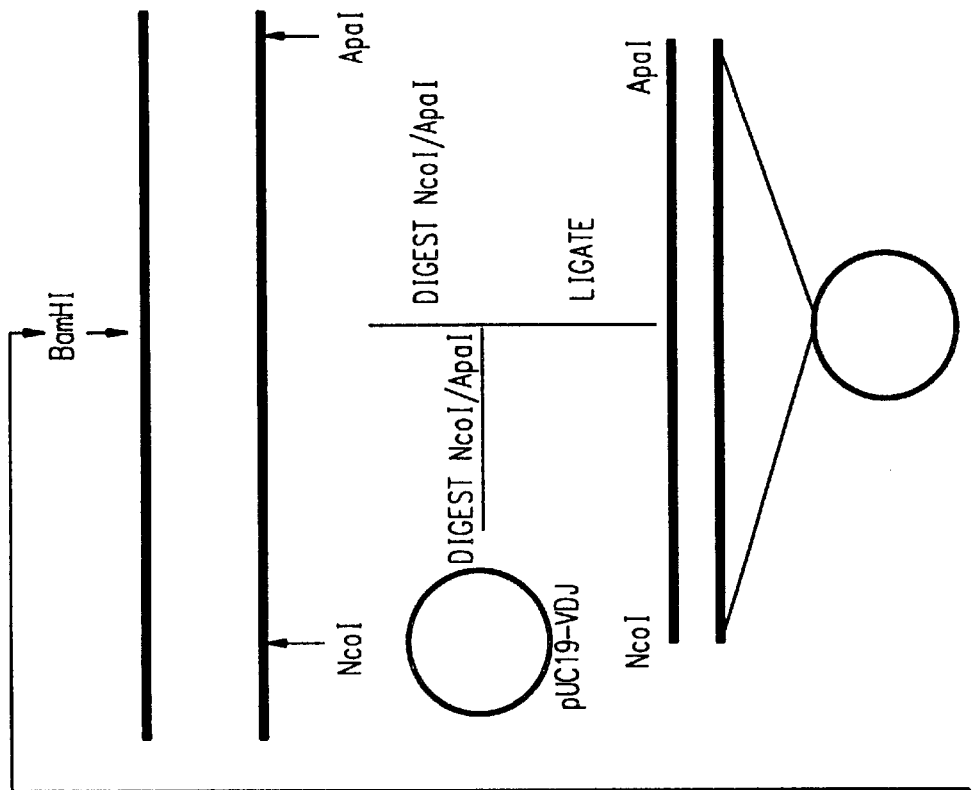
FIG. 5 illustrates the insertion of B cell epitope HA sequence in place of CDR2 segment.
Figure 5:
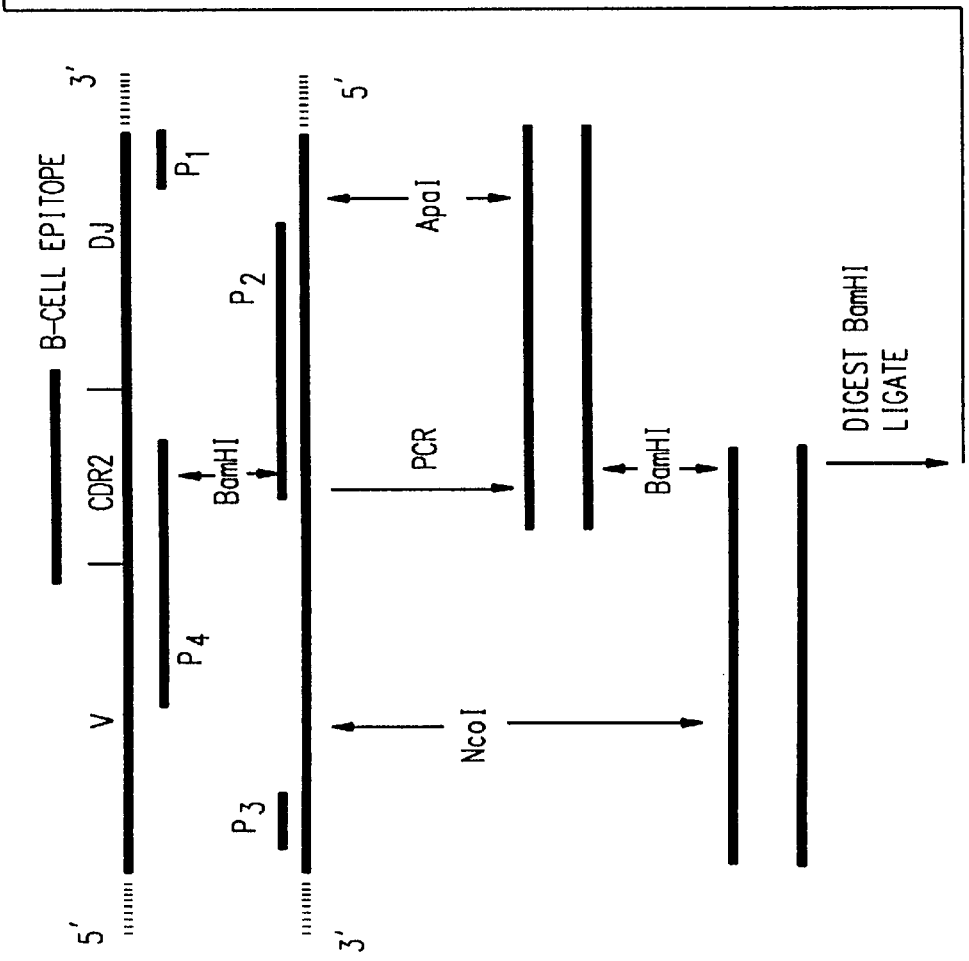

In order to introduce a B cell epitope into Ig-HA, the CDR2 loop of Ig-HA may be replaced with 10 amino acid residues, WLTEDEGSYP SEQ ID NO: 17, which have been shown to be an immunodominant B cell epitope in site B of PR8 virus hemagglutinin, using similar methods. A DNA fragment encoding the H chain V region, encompassing the H chain Ig promoter and enhancer, the leader sequence, the V-HA110–120-J chimeric variable region, and the major intron of Ig-HA may be subcloned and used as a template DNA along with four different primers in two sets of PCR reactions designed to replace the CDR2 loop with nucleotide sequences that will encode the HA B cell peptide. The sequences of the primers may be as follows: Primer P1 may have the sequence (5'-AGCTGAGGACAAAGAAGA-3') (SEQ ID NO: 18), complementary to sequences within the intron region downstream of the Apa I site. Primer P2 may have the sequence (5'-CCGAAAAGGAGGGA-TCCTATCCCAAGACCACACTGACTGTACACAAA-3') (SEQ ID NO: 19), which contains 5' unmatched sequences corresponding to a portion of the B cell epitope of HA and 3' sequences complementary to sequences starting at the last base downstream of the CDR2. Primer P3 may have the sequence (5'-CAAATCACCCAAGTGTATGGC-3') (SEQ ID NO: 20), which is complementary to noncoding sequences upstream of the NcoI site and primer and P4 may have the sequence (5'-GGGATAGGATCCCTC-CTTTTCGGTTAACCATCCAATCCATTCCAGCCCCT-GTCCAGGCCT-3') (SEQ ID NO: 21), which contains 5' sequences corresponding to a portion of the B cell epitope of HA epitope and 3' sequences complementary to sequences starting at the first base upstream of the CDR2 loop. In the first set of reactions, 100 ng of template DNA may be used with 500 ng of each primer P1 and P2 to generate a fragment spanning a portion of the B cell epitope and V-HA110–120-J and intron sequences. In the second set of PCR reactions, 100 ng of template DNA may be used with primers P3 and P4 (500 ng each) to generate a fragment spanning the opposite portion of the B cell epitope of HA, upstream V region sequences and leader and promoter sequences. The two fragments may then be digested with BamHI and ligated through this intentionally created site to generate a fragment containing the full B cell epitope sequence in place of CDR2. This fragment may be digested with NcoI and ApaI and subcloned into pUC19–91A3 $V_H$ from which an NcoI-ApaI fragment was cut out. FIG. 5 illustrates the insertion of B cell epitope of HA sequence in place of CDR2 segment. Nucleotide sequencing analysis (FIG. 6) of two clones produced according to the above method, termed C3 and C8, show the deletion of CDR2 sequence of 91A3 $V_H$-HA110–120 and insertion in the correct frame of sequence encoding the B cell epitope. The new 5.5 kb 91A3 doubly chimeric fragment may be subcloned into the EcoR1 site of the expression vector pSV2-gpt Cγ2b in front of the exons encoding the constant region of a BALB/c γ2b. The resulting vector may be cotransfected with pSV2-neo-91A3 $V_kJ_kC_k$ into the nonsecreting BALB/c myeloma B cell line, SP2/0. Positive clones secreting Ig-HA-B may be selected with mycophenolic acid and geneticin, and Ig-HA-B may be purified from transfectoma supernatant on a rat anti-mouse K light chain antibody-sepharose column.

The present invention provides for purified and isolated nucleic acid molecules encoding chimeric immunoglobulin molecules, as set forth above, to such nucleic acid molecules comprised in suitable vector molecules, and to cells and cell lines into which such nucleic acid molecules have been introduced.

5.5. Chimeric Antibodies

The present invention relates to chimeric antibodies which comprise parent immunoglobulin molecules to which have been added one or more elements selected from the group consisting essentially of B cell epitopes, T cell epitopes, and antigen binding sites. Such epitopes and/or antigen binding sites may preferably be added by genetic engineering of immunoglobulin genes, as described above.

The present invention provides for compositions comprising purified chimeric antibody molecules which comprise chimeric immunoglobulin molecules, as described above.

A first nonlimiting embodiment of the invention provides for a composition comprising purified antibody comprising a chimeric immunoglobulin molecule which comprises a B cell epitope. An example of such an antibody is set forth in Example Section 8, below.

A second nonlimiting embodiment of the invention provides for a composition comprising purified chimeric antibody comprising a chimeric immunoglobulin molecule which comprises a $T_h$ cell epitope. An example of such an antibody is Ig-HA, described above.

A third nonlimiting embodiment of the invention provides for a composition comprising purified chimeric antibody comprising a chimeric immunoglobulin molecule which comprises a CTL cell epitope. An example of such an antibody is set forth in Example Section 7, below.

A fourth nonlimiting embodiment of the invention provides for a composition comprising purified chimeric antibody comprising a chimeric immunoglobulin molecule which comprises an antigen binding site. For example, such an antigen binding site may be able to bind to CD3 antigen on the surface of CTLs, which may activate such CTLs.

In additional embodiments of the invention, recombinant antibodies may be produced which contain more than one B cell epitope, T cell epitope, or antigen binding site, including combinations of these elements. Such antibodies may be produced by any of the methods set forth above, including, but not restricted to, methods which replace portions of immunoglobulin genes and proteins. That is to say, the addition of nucleic acid or amino acid to immunoglobulin genes or proteins, resptectively, is within the scope of the invention. The following embodiments relate to antibodies which contain more than one epitope or antigen binding site.

A fifth nonlimiting embodiment of the invention provides for a composition comprising purified chimeric antibody comprising both a CTL epitope as well as a target antigen binding site. The CTL epitope and antigen binding site may reside within the same chimeric immunoglobulin molecule.

A sixth nonlimiting embodiment of the invention provides for a composition comprising purified chimeric antibody comprising both a B cell epitope as well as a $T_h$ epitope. The B cell epitope and $T_h$ epitope may reside within the same chimeric immunoglobulin molecule or in different chimeric immunoglobulin molecules. An example of such a chimeric antibody is described in the preceding section, and includes a B cell HA epitope as well a $T_h$ HA epitope. Further examples of B/$T_h$ combinations include, but are not limited to, combinations where both epitopes derive from the same pathogen, such as influenza virus, measles virus, respiratory syncytial virus, tetanus toxoid, HIV-1, and HIV-2, to name but a few. Preferably, the B cell epitope resides in the variable region of both arms of a Y-shaped immunoglobulin, and the $T_h$ epitope resides in the variable region of both arms of the Y-shaped immunoglobulin. Such a chimeric antibody may induce the production of antibodies directed toward the B cell epitope, thereby augmenting the effectiveness of the humoral component of the immune response.

A seventh nonlimiting embodiment of the invention provides for a composition comprising purified chimeric antibody comprising a B cell epitope and is covalently linked to a non-immunoglobulin molecule bearing a $T_h$ epitope. Preferably, the B cell epitope resides in the variable region of both arms of a Y-shaped immunoglobulin, and the $T_h$ epitope is covalently linked to the hinge region of the Y-shaped immunoglobulin. For example, the non-immunoglobulin molecule may be tetanus toxoid, as discussed in Example Section 8, below. Such a chimeric antibody may induce the production of antibodies directed toward the B cell epitope, thereby augmenting the effectiveness of the humoral component of the immune response.

An eighth nonlimiting embodiment of the invention provides for a composition comprising purified chimeric antibody comprising a first antigen binding site which recognizes a tumor cell or pathogen and a second antigen binding site that binds to a CTL surface protein, wherein binding of the second antigen binding site to the CTL surface protein activates the CTL. For example, the first antigen binding site may bind to a viral antigen, such as an influenza or HIV antigen, and the second antigen binding site may bind to CD3. FIG. 3 depicts such an antibody. The first antigen binding site may bind to viral antigen expressed on the surface of an infected cell, and the second antigen binding site may bind to a CTL, thereby bringing the CTL into proximity to the infected cell and activating the lytic activity of the CTL. Preferably, the first antigen binding site resides in the variable region of one arm of a Y-shaped immunoglobulin, and the second antigen binding site resides in the variable region of the other arm of the Y-shaped immunoglobulin.

Various chimeric antibodies which, according to the invention, comprise chimeric immunoglobulins bearing more than one B cell epitope, T cell epitope, or antigen binding site, may be prepared by a number of methods. Without limitation, these methods include the following. If one chimeric immunoglobulin molecule is to be expressed, nucleic acid encoding that molecule may be introduced into a cell for expression, as described above. If more than one chimeric immunoglobulin molecule is to be expressed, nucleic acid molecules encoding such molecules may be co-introduced into a cell for expression or, alternatively, nucleic acid encoding the various molecules may be introduced into separate parental cells which are later fused to produce a combination of chimeric immunoglobulin molecules. In such case, prior to fusion, each of the parental cells may be induced to express a different selectable marker, such that fusions between different species of parental cells may be identified by selecting for the presence of the appropriate combination of selectable markers. For example, genes encoding different selectable markers may be introduced into the different parental cell lines.

It has further been discovered that the stability of such recombinant antibodies and/or their ability to enhance the immune response is augmented when the antibodies are mildly derivatized with polyethylene glycol ("pegylated"). Mild derivatization of chimeric immunoglobulins with mPEG may significantly increase their half lives and stability without alteration of biological activity. The increase in half life may enhance the immunogenicity of such molecules and obviate the requirement for adjuvants. For example, and not by way of limitation, the beneficial effects of pegylation of various chimeric antibodies described herein is set forth in Example Sections 9 and 10, below.

5.6 Replacement of a CDR Loop of an Immunoglobulin with One or More Epitopes A preferred embodiment of the present invention relates to a chimeric immunoglobulin molecule produced by recombinant DNA technology which comprises a parent immunoglobulin molecule from which a CDR loop (a CDR region) has been deleted and replaced by a foreign peptide sequence corresponding to a T cell epitope or a B cell epitope. The T cell epitope can be a CTL epitope or a helper T cell epitope. The inserted T cell or B cell epitope occurs in the chimeric immunoglobulin molecule in place of the deleted CDR loop and retains its specificity as an epitope. Examples of such immunoglobulin molecules are set forth in Example Sections 7 and 8, and further examples of B and T cell epitopes are set forth in the preceding sections 5.1 and 5.2.

As used herein, a foreign peptide sequence refers to a peptide sequence which does not naturally occur at the region of the parent immunoglobulin molecule into which it is inserted. It is preferable that the B cell or the T cell epitope inserted in place of the deleted CDR loop of the parent immunoglobulin molecule be of approximately the same size as the deleted CDR loop.

A general method of preparing a chimeric immunoglobulin molecule of the present invention using the recombinant DNA technology and polymerase chain reaction is set forth in the preceding section 5.4. This general method can be modified and used in generating the chimeric immunoglobulin molecules described herein, which contain a B cell or a T cell epitope in place of the deleted CDR loop of the parent immunoglobulin molecule. Furthermore, a method of replacing a CDR3 loop (D segment) with a B cell epitope or a T cell epitope is specifically set forth in Example Sections 7 and 8 and a method of replacing a CDR2 loop is specifically set forth in the preceding section 5.4. These methods can be modified to be used in replacing a CDR1 loop with a B cell or a T cell epitope The CDR loop deleted and replaced by a B cell or a T cell epitope can be CDR1, CDR2, or CDR3 (D segment) of the heavy chain of the parent immunoglobulin molecule or it can be CDR1, CDR2, or CDR3 of the light chain of the parent immunoglobulin molecule.

The present invention also relates to a chimeric immunoglobulin molecule produced by recombinant DNA technology which comprises a parent immunoglobulin molecule from which a CDR loop (a CDR region) has been deleted and replaced by a foreign peptide sequence corresponding to a T cell epitope and from which another CDR loop (a CDR region) has been deleted and replaced by a foreign peptide sequence corresponding to a B cell epitope. The T cell epitope can be a CTL epitope or a helper T cell epitope. The CDR loop replaced by the T cell epitope and the CDR loop replaced by the B cell epitope are not identical. In such an immunoglobulin molecule, the T cell epitope and the B cell epitope both occur in the chimeric immunoglobulin molecule, each in place of the corresponding CDR loop which has been deleted, and retain their respective specificity as an epitope.

The chimeric immunoglobulin molecule containing both a T cell epitope and a B cell epitope, as described above, can have a variety of configurations. For example, the T cell epitope and the B cell epitope can each replace a CDR loop of the heavy chain of the parent immunoglobulin molecule, the CDR loop being selected from the group consisting of CDR1, CDR2, and CDR3 (D segment) or the T cell epitope and the B cell epitope can each replace a CDR loop of the light chain of the parent immunoglobulin molecule, the CDR loop being selected from the group consisting of CDR1, CDR2 and CDR3. It is also possible to engineer the chimeric immunoglobulin molecule such that the T cell epitope replaces a CDR loop located in the heavy chain of the parent immunoglobulin molecule, while the B cell epitope replaces a CDR loop located in the light chain thereof, or the other way around.

The T cell epitope and/or the B cell epitope inserted into the chimeric immunoglobulin molecule of the present invention can be a viral epitope. The viral epitope can be derived from the group consisting of respiratory syncytial virus, measles virus, rotavirus, hepatitis C virus, influenza virus, and human immunodeficiency virus.

The present invention also provides for compositions comprising chimeric immunoglobulin molecules described herein above. The present invention further provides vaccines comprising those compositions and a suitable carrier and methods of conferring immunity to a subject against a pathogen which comprises administering to the subject an effective amount of vaccines. Utilities of the chimeric immunoglobulin molecules of the present invention, including their diagnostic in vitro utilities are set forth in section 5.7.

The present invention further provides purified and isolated recombinant nucleic acid molecules encoding the chimeric immunoglobulin molecules described herein, expression vectors into which those recombinant nucleic acid molecules are introduced, and host cells transfected with those vectors.

The present invention provides a method of preparing the chimeric immunoglobulin molecule comprising deleting a portion of nucleic acid sequence encoding a parent immunoglobulin molecule and replacing the deleted portion with a foreign nucleic acid sequence encoding a T cell epitope to form a chimeric nucleic acid sequence, the replaced nucleic acid sequence encoding a CDR loop of the parent immunoglobulin molecule, and then expressing the chimeric nucleic acid sequence, such that the T cell epitope occurs in the parent immunoglobulin molecule in place of the deleted CDR loop and maintains its specificity as an epitope.

By using a nucleic acid sequence encoding a B cell epitope in place of the nucleic acid sequence encoding the T cell epitope in the method described above, a chimeric immunoglobulin molecule containing a B cell epitope can be prepared, such that the B cell epitope occurs in place of the deleted CDR loop in the parent immunoglobulin molecule and maintains its specificity as an epitope.

The present invention also provides a method of preparing the chimeric immunoglobulin molecule comprising deleting and replacing a first portion of nucleic acid sequence encoding a parent immunoglobulin molecule with a foreign nucleic acid sequence encoding a T cell epitope and deleting and replacing a second portion of nucleic acid encoding the parent immunoglobulin molecule with a foreign nucleic acid sequence encoding a B cell epitope to form a chimeric nucleic acid sequence, the first portion encoding a CDR loop of the parent immunoglobulin molecule and the second portion encoding another CDR loop of the parent immunoglobulin, and then expressing the chimeric nucleic acid sequence, such that the T cell epitope and the B cell epitope occur in the parent immunoglobulin molecule in place of the deleted CDR loops and maintain their specificity as epitopes.

In one embodiment of the present invention, the parent immunoglobulin used in preparing the chimeric immunoglobulin molecules described above is a human immunoglobulin molecule. In another embodiment of the present invention, the parent immunoglobulin is a murine immunoglobulin molecule. In yet another embodiment of the invention, the parent immunoglobulin molecule comprises the constant domain of the human immunoglobulin molecule and the variable domain of the murine immunoglobulin molecule.

The present invention also relates to a method of increasing the stability and the half life of the chimeric immunoglobulin molecules of the present invention which comprises mildly derivatizing the chimeric immunoglobulin molecules with polyethylene glycol. The present invention further relates to compositions comprising these chimeric immunoglobulin molecules which have been mildly derivatized by reacting the chimeric immunoglobulin molecules with polyethylene glycol (pegylated), vaccines comprising these pegylated chimeric immunoglobulin molecules, and methods of immunizing a subject against pathogens which comprises administering to the subject an effective amount of the pegylated chimeric immunoglobulin molecules.

5.7. Use of Antibodies of the Invention

The chimeric antibodies of the present invention may be useful in the diagnosis and treatment of a wide variety of malignancies and viral infections. They are particularly well suited for treatment of infections by viruses which upon infection of the host cell cause expression of viral coat proteins prior to cell death. In most cases this cellular expression of viral coat proteins leads to a cell surface form of such proteins. Examples include but are not limited to the hemagglutinin protein complex of influenza virus, the env proteins of murine leukemia virus, the env proteins of Rous sarcoma virus and the env proteins of HIV. Often the viral protein expressed by infected cells is the same viral coat protein which recognizes and binds to the cell receptor protein to initiate infection. This is true in the case of HIV.

Accordingly, the present invention provides for a method of treating a viral (or bacterial, protozoan, mycoplasmal, or fungal) infection comprising administering, to a subject in need of such treatment, an effective amount of a composition comprising purified recombinant antibody, as described in the preceding section. The term "treating" as used herein refers to an amelioration in the clinical condition of the subject, and does not necessarily indicate that a complete cure has been achieved. An amelioration in clinical condition refers to a prolonged survival, a decreased duration of illness, or a subjective improvement in the quality of life of the subject.

The present invention provides for a method of enhancing an immune response directed toward a viral, protozoan, mycoplasmal, bacterial or fungal pathogen, in a subject in need of such treatment, comprising administering, to a subject in need of such treatment, an effective amount of a composition comprising purified recombinant antibody, as described in the preceding section. The phrase "enhancing an immune response" refers to an increase in cellular and/or humoral immunity. In preferred embodiments, the amount of cellular and/or humoral immunity is increased in the subject by at least 25 percent. Such an enhanced immune response may be desirable during the course of infection, or before infection may have occurred (for example, in the context of a vaccine).

The present invention also provides for a method of treating a malignancy or other neoplasm comprising administering, to a subject in need of such treatment, an effective amount of a composition comprising purified recombinant antibody, as described in the preceding section. In addition to the definition of "treating" set forth above, tumor regression, such as a decrease in tumor mass or in the number of metastases, of preferably at least 25 percent would be considered "treating".

Further, the present invention provides for a method of enhancing an immune response directed toward a malignancy or other neoplasm, in a subject in need of such treatment, comprising administering, to a subject in need of such treatment, an effective amount of a composition comprising purified recombinant antibody, as described in the preceding section.

The foregoing methods may also be practiced by administering, to a subject in need of such treatment, a cell expressing chimeric immunoglobulin molecules. For example, B cells may be harvested from a subject suffering from an infection with a pathogen or from a malignancy. The collected B cells may be transfected with genes encoding chimeric immunoglobulins comprising the appropriate T cell epitope. Tranfected B cells expressing the chimeric immunoglobulin may then be reintroduced into the subject in order to sensitize the subject to the pathogen or malignancy and thereby enhance the subject's immune response toward the pathogen or malignancy.

As with all pharmaceutical compositions, the effective amounts of the antibodies of the invention may be determined empirically. Factors to be considered include the condition to be treated, whether or not the antibody will be complexed with or covalently attached to a toxin, route of administration for the composition, i.e. intravenous, intramuscular, subcutaneous, etc., and the number of doses to be administered. Such factors are known in the art and it is well within the skill of physicians to make such determinations without undue experimentation.

The recombinant antibodies of the invention offer a number of in vitro utilities, and the invention provides for methods based on such utilities. Such utilities include, but are not limited to, the following.

An antibody comprising a chimeric immunoglobulin molecule which comprises a B cell epitope may be used to label B cells. For example, such an antibody may be detectably labelled, and may be used to quantitate the number of B cells binding to the particular epitope in a sample of lymphocytes collected from the subject. Similarly, such an antibody, which need not be detectably labelled, may be used to test the ability of a subject to mount a humoral response to the particular B cell epitope. The inability of lymphocytes of a subject to produce antibodies after exposure to the chimeric immunoglobulin may indicate that the subject is not capable of developing humoral immunity to the epitope. Further, such an antibody may be used to collect B cells which recognize the epitope; for example, the antibody may be fluorescently labelled, so that the B cells may be collected by fluorescence-activated cell sorting.

An antibody comprising a chimeric immunoglobulin molecule which comprises a $T_h$ cell epitope may be used to used to test the ability of a subject to mount an immune response to the particular $T_h$ cell epitope. For example, peripheral blood lymphocytes may be collected from a test subject, and then, in a standard proliferative assay, may be exposed to the chimeric immunoglobulin molecule bearing the $T_h$ epitope. The amount of proliferation may then be determined, and may be compared to the degree of proliferation exhibited by peripheral blood lymphocytes from a control subject who has not been exposed to the epitope. A result, in which the amount of proliferation exhibited by the lymphocytes from the test subject is significantly greater than the amount of proliferation exhibited by the lymphocytes from the control subject, positively correlates with prior exposure of the test subject to the epitope, and may indicate that the test subject is or has been infected with a pathogen containing the epitope.

An antibody comprising a chimeric immunoglobulin molecule which comprises a CTL cell epitope may be used to test the ability of a subject to mount a cellular response to the particular CTL cell epitope. For example, peripheral blood lymphocytes may be collected from a test subject and exposed to the detectably labelled target cells (such as hybridoma cells) expressing chimeric immunoglobulin bearing the CTL epitope. The ability of the peripheral blood lymphocytes to lyse the target cells provides an evaluation of the ability of the subject to mount an effective cell-mediated immune response against a pathogen or tumor cell expressing the CTL epitope. The inability of lymphocytes of a subject to exhibit cytotoxic activity may indicate that the subject is not capable of exercising cellular immunity to the epitope.

An antibody comprising a chimeric immunoglobulin molecule which comprises an antigen binding site may be used in diagnostic assays to detect the presence of a particular target antigen, which binds to the antibody binding site. For example, a sample collected from a subject may be immobilized, and then reacted with an effective amount of the chimeric immunoglobulin molecule. Labelled secondary antibodies, directed against the immunoglobulin molecule, may then be used to detect the presence of, and/or quantitate the amount of, chimeric immunoglobulin bound. The presence of bound chimeric immunoglobulin may be used to confirm the presence of, and/or quantitate the amount, of target antigen present. Antigens that may be detected in this manner may include prostate specific antigen, Hep BS Ag, HIV antigens, etc.

The following examples are meant to illustrate but not limit this invention.

6. EXAMPLE: PREPARATION OF RECOMBINANT ANTIBODIES COMPRISING VARIOUS EPITOPES

All enzymes were used according to the manufacturer's instructions (New England Biolabs, Beverly, Mass.). Unless otherwise specifically mentioned, DNA cloning was performed according to the methods described in Maniatis et al., "Molecular Cloning a Laboratory Manual," Cold Spring Harbor Press, Cold Spring Harbor N.Y. (1982).

Using this method the D segment of VH region of 91A3 anti-arsonate antibody is replaced with one of:

(a) The consensus sequence of the B cell epitope of the cysteine loop of gp12O. The sequence of this epitope varies, however, a consensus sequence deduced from 245 HIV isolate sequences borne by 245 isolates was established. The amino acid sequence of the consensus corresponds to residues 301–319 of gp12O and is as follows: Arg-Lys-Ser-Ile-His-Ile-Gly-Pro-Gly-Arg-Ala-Phe-Tyr-Thr-Thr-Gly-Glu-Ile-Ile (termed "V$_3$C") (SEQ ID NO: 1)

(b) The T cell epitope of residues 12–35 of HIV-1 H×B2 isolate Glu-Leu-Asp-Arg-Trp-Glu-Lys-Ile-Arg-Leu-Arg-Pro-Gly-Gly-Lys-Lys-Lys-Tyr-Lys-Leu-Lys-His-Ile-Val (SEQ ID NO: 22)

(c) A T cell epitope of HIV-1 reverse transcriptase; residues 325–349 Ala-Ile-Phe-Gln-Ser-Ser-Met-Thr-Lys-Ile-Leu-Glu-Pro-Phe-Arg-Lys-Gln-Asn-Pro-Asp-Ile-Val-Ile-Tyr-Gln (SEQ ID NO: 23)

(d) The amino acid sequence corresponding to the amino acid residues of the principal neutralizing determinant (PND) of WMJ2 HIV-1 isolate at the same positions as the consensus sequence of (a) Arg-Arg-Ser-Leu-Ser-Ile-Gly-Pro-Gly-Arg-Ala-Phe-Arg-The-Arg-Glu-Ile-Ile-Gly (termed "V$_3$M") (SEQ ID NO: 24)

(e) The amino acid sequence corresponding to amino acid residues 519–535 of HIV-1 IIIB isolate Ala-Val-Gly-Ile-Gly-Ala-Leu-Phe-Leu-Gly-Phe-Leu-Gly-Ala-Ala-Gly-Ser (SEQ ID NO: 25)

(f) The amino acid sequence corresponding to residues 110–120 of the hemagluttin of influenza A virus Ser-Phe-Glu-Arg-Phe-Glu-Ile-Phe-Pro-Lys-Glu (SEQ ID NO: 7)

(g) The NP 147–161 peptide corresponding to nucleoprotein of PR8 influenza virus peptide The-Tyr-Gln-Arg-The-Arg-Ala-Leu-Val-Arg-The-Gly-Met-Asp-Pro (SEQ ID NO: 15) and (h) The influenza virus B cell epitope W-L-T-E-K-E-G-S-Y-P (SEQ ID NO: 26).

The foregoing epitopes were inserted into the V$_H$ gene of the 91A3 anti-arsonate antibody by replacing the parental D segment (CDR3, for PR8 HA110–120) or CDR2 (for PR8 HA B cell epitope) using methods exemplified by the insertion of the NP epitope, described in detail in the following section.

7. EXAMPLE: INSERTION OF THE NP CTL EPITOPE INTO AN ANTI-ARSONATE PARENT IMMUNOGLOBULIN MOLECULE

7.1. Preparation of the Chimeric Immunoglobulin Molecule

Figure 4:
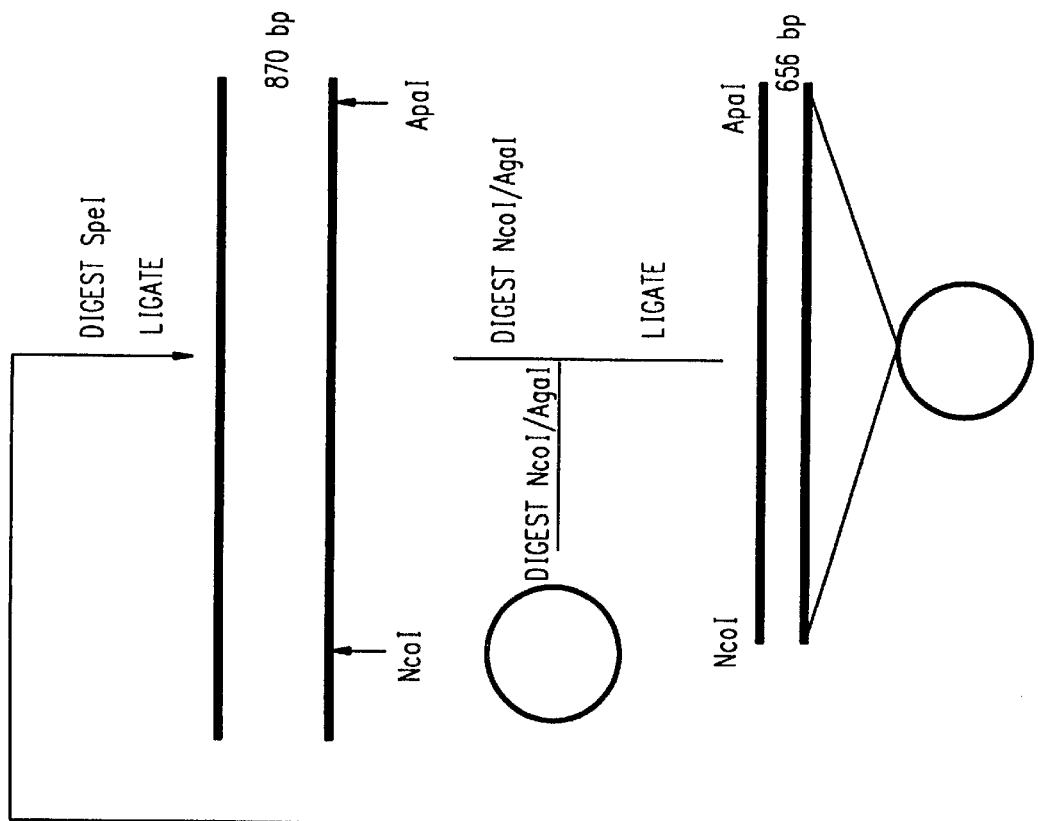
FIG. 4 is a flow diagram showing a cloning scheme of the VH-D-J region.
Figure 4:
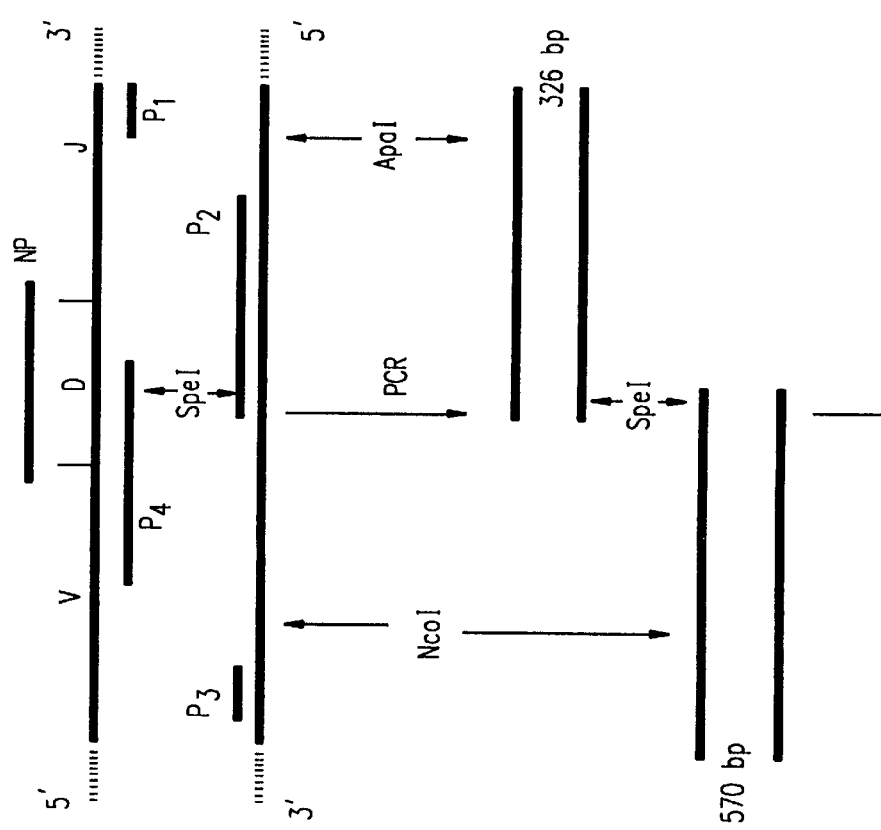

The procedure for deleting the 27 nucleotides coding for the D segment of the heavy chain of the 91A3 antibody, and the insertion of 45 bases corresponding to the NP epitope, is summarized in FIG. 4.

Briefly, cloning was done by subcloning the 5.5 kb 91A3VHDJ fragment into the EcoRI restriction endonuclease site of the pUC19 plasmid. Two unique restriction endonuclease sites (NcoI and ApaI, 638 bp apart,) surrounding the D region were identified. The primers P1 and P3, shown in FIG. 4, are exactly complementary to their corresponding strands. However P2 matches with its complementary strand down to the last nucleotide 5' of the D region (filled part of the bar). The remaining 30 nucleotides (hatched part of the bar) are those of the NP epitope. Primer P4 contains nucleotides complementary to the corresponding strand down to the last nucleotide 5' of the D region. The remaining unmatched nucleotides correspond to 30 bases of the NP epitope. An SpeI restriction endonuclease site was created within the overlapping nucleotides between P2 and P4.

Using polymerase chain reaction, two fragments were produced. In one set of reactions, the annealing of the P3 and P4 primers to the plasmid resulted in the production of 570 bp fragment. In another set of reactions, the annealing of P1 and P2 to plasmid provided a 326 bp fragment. To delete the NP overlapping sequences, both fragments were digested with SpeI. The ligation of fragments, sharing each half of the NP epitope, generated an 870 bp fragment containing the 45 bp NP epitope inserted in-frame. The following steps consist of digesting both the original pUC19-VHDJ91A3 and the 870 bp fragment with the restriction endonucleases NcoI and ApaI. The ligation of the 656 bp fragment into the digested plasmid provides a vector possessing the coding region of the NP epitope instead of the D segment. The 5.5 kb EcoRI VH-NP.J fragment was then subcloned into the EcoRI restriction endonuclease site of the expression vector.

Cotransfection was done using the gene pulsar transfection apparatus according to the manufacturer's instructions (Biorad). Cotransfection of the pSV2gpt-91A3-VHNPJ-CIgG2b and the pSV2neo-91A3LY plasmids into the non-secreting myeloma cell line SP2/0 and selection with mycophenolic acid and geneticin (G418) resulted in the synthesis and secretion of the 91A3-NP chimeric antibody.

7.2. The Chimeric Immunoglobulin Contains the NP Epitope

The results presented in Tables 1 and 2 show that chimeric immunoglobulin bearing the influenza virus NP epitope bound rabbit anti-NP antibodies, indicating that the NP epitope had been successfully inserted into the 91A3 antibody. Further, the chimeric immunoglobulin exhibited substantially diminished binding to arsonate, presumably because the D segment, which plays an important role in the binding of arsonate, was replaced with viral NP peptide.

TABLE 1

Immunochemical Properties of Immunoglobulins Produced by SP2/0 Coinfected with pSV2gpt-91A3gpt-91A3V-NP-J and pSV2neo-91A3L

| Binding to | 91A3HL-NP | 91A3HL |
|---|---|---|
| Ars BSA | 15,445 ± 101 | 792 ± 22 |
| Rabbit Antimouse IgG2b | 42,724 ± 127 | 41,422 |

Binding to arsonate was determined by incubation of 10 ng of antibody on a microtiter plate coated with either arsonate BSA or BSA alone and bound antibodies were revealed with $^{125}$I rat antimouse κ antibody. Binding to anti-isotype antibody was performed by incubation of 10 ng of antibodies on plates coated with rat antimouse κ mAB and bound antibody was revealed using $^{125}$I goat antimouse IgG2b antibodies.

TABLE 2

Binding Properties of 91A3 Chimeric Immunoglobulin (in cpm)

| Binding to | 91A3HL-NP (chimeric) | 91A3HL (parent) |
|---|---|---|
| Arsonate BSA | 792 ± 22 | 15,445 ± 101 |
| Anti-NP antibodies | 5,616 ± 217 | 1,246 ± 76 |

Binding to arsonate-BSA was carried out as described above. Binding to rabbit anti-NP antibodies was assessed by incubating transfectoma supernatants on microtiter plates coated with affinity chromatography purified anti-NP antibodies and bound antibodies were revealed using $^{125}$I goat antimouse IgG2b.

7.3. The Chimeric Immunoglobulin Activates CTLS

NP-specific CTL were able to kill SP2/0 transfected with chimeric immunoglobulin gene, indicating that the NP epitope was expressed on the cell surface, as in cells infected with the virus.

NP-specific cytotoxic T cell clones were generated from BALB/c mice immunized with PR8 influenza virus and expanded in vitro with irradiated spleen cells coated with 5 μg NP 147–161 peptide. The cytotoxicity assay was carried out by incubating $^{51}$Cr-labeled target cells and NP-specific CTL at 10:1 E/T ratio for 4 hours.

The data in Table 3 (panel A) show that the CTL clone is able to kill PR8 and X31 influenza virus infected P815 cells (H-$2^d$) as well as P815 cells coated with NP 147–161 peptide. No significant killing was seen with P815 cells coated with irrelevant NP 365–379 peptide (IASNENMDAMESSTS) (SEQ ID NO: 27) known to be recognized in association with H-$2D^b$ by C57BL/6 CTL. Panel B shows the ability of NP specific CTL to kill SP2/0 cells, transfected with the 91A3 heavy chain gene carrying the NP 147–161 sequence (SP2/0-91A3H-NP147–161). The CTLs also killed cells cotransfected with 91A3H-NP147–161 and wild-type 91A3 light chain gene (91A3HL-NP147–161). The CTLs were not able to lyse SP2/0 transfected with wild-type, 91A3H, 91A3L or 91A3HL genes. However, SP2/0 transfected with wild type H and L gene (91A3HL) and coated with NP147–161 were killed by the CTLs.

TABLE 3

Killing of SP2/0 cells transfected with plasmid carrying the $V_H$-NP chimeric gene ($V_{HC}$), by NP-specific CTL

| | Target Cells | % Specific (1) | $^{51}$Cr release (2) |
|---|---|---|---|
| A | P815 | 14 | 12 |
| | P815 coated with NP147-161 | 77 | 49 |
| | P815 coated with NP365-379 | 14 | 10 |
| | P815 infected with PR8 | 59 | 51 |
| | P815 infected with X31 | 77 | 64 |
| | P815 infected with B Lee | 19 | 9 |
| B | SP2/0 | ND* | 2 |
| | SP2/0/91A3L | 9 | ND |
| | SP2/0/91A3HL coated with NP147-161 | 30 | ND |
| | SP2/0/91A3HL coated with NP365-379 | 7 | ND |
| | SP2/0/91A3H | 2 | ND |
| | SP2/0/91A3HL | 4 | ND |
| | SP2/0/91A3H-NP147-161 | 44 | 39 |
| | SP2/0/91A3HL-NP147-161 | 28 | 21 |

*ND = not done

These results clearly show that cells transfected with chimeric immunoglobulin genes bearing an epitope of influenza virus recognized by CTL are killed by CTL as are influenza infected cells or cells artificially (in vitro) coated with peptide.

In further experiments we found that SP2/0 cells or even BALB/c spleen cells that were pulsed with soluble 91A3HL-NP147–161 (also designated Ig-NP) and labelled with $^{151}$Cr were not killed by the specific CTL. This is in agreement with the general observation that only proteins synthesized by the target cells themselves are presented by MHC class I molecules and recognized by CTLS. This is because they are processed in a compartment that allows the peptides to be transported to the endoplasmic reticulum where they bind MHC class I antigen. Soluble Ig-NP is processed in the endosomal compartment and therefore the NP147–161 generated from it will not be able to encounter MHC class I antigen.

8. EXAMPLE: INDUCTION OF ANTIBODIES TO HIV 1 BY IMMUNIZATION OF BABOONS WITH CHIMERIC IMMUNOGLOBULIN MOLECULES 8.1. Preparation of Chimeric Immunoglobulin Polymerase chain reaction (PCR) mutagenesis as described in Zaghouani, H. et al., J. Immunol., 148, 3604–3609 and Zaghouani et al., 1993, Science, 259, 224–227 was used to create $V_H$ genes encoding HIV-1 sequences described in Example 6(a) and (d) above.

Figure 7C:
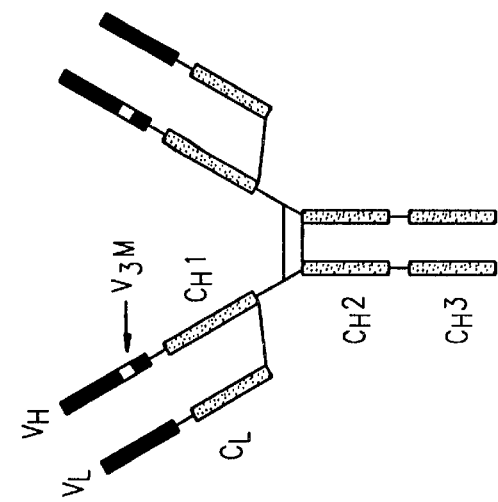
Figure 7B:
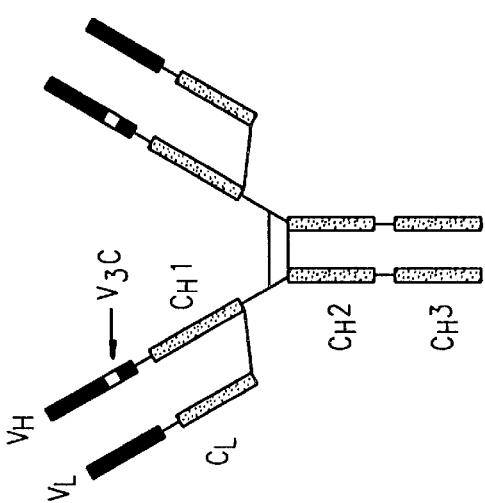
Figure 7A:
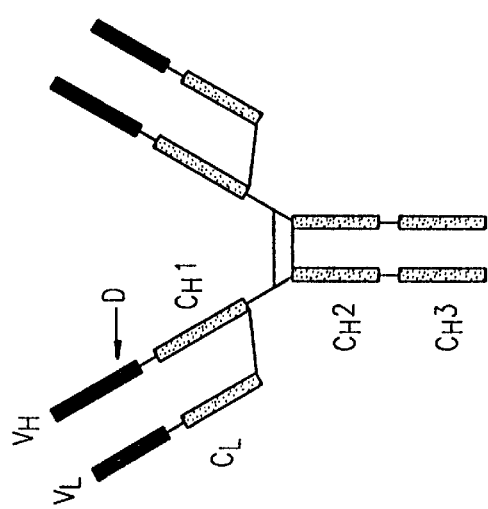
Figure 7F:
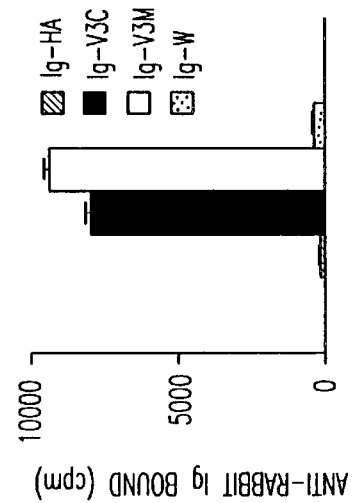
Figure 7E:
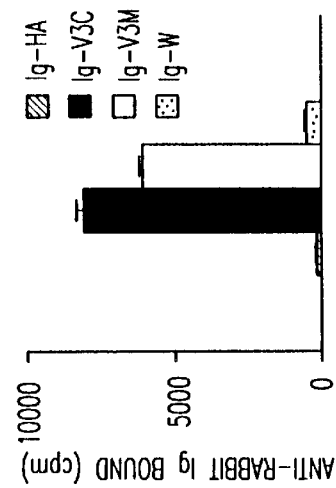
Figure 7D:
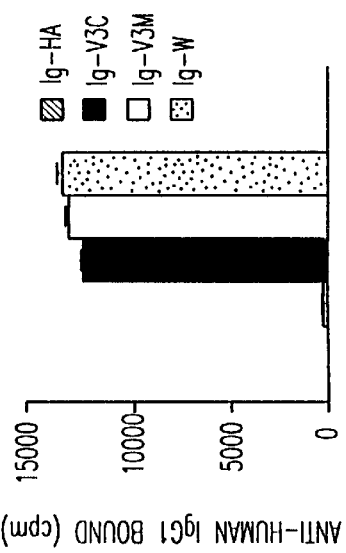

These chimeric $V_H$ genes as well as the wild type 91A3 $V_H$ gene were subcloned into the EcoRI site upstream of the exons encoding a human γ1 constant region within the plasmid pSV2ΔHgptDNSV$_H$-hC1γ as described in Dange, J. C. et al. EMBO J. 7, 1994–1988 (1988) from which the EcoRI dansyl (DNS) $V_H$ gene was cut out. Thus, three constructs were generated: pSV2ΔHgpt91A3V$_H$-V$_3$C-hCγ1 carries nucleotide sequences encoding the consensus V$_3$C peptide (Example 1(a)) in place of the D segment; pSV2ΔHgpt91A3V$_H$-V$_3$M-hCγ1, carries nucleotide sequences encoding the V$_3$M peptide (Example 1(d)) instead of the D segment; and pSV2ΔHgpt91A3V$_H$-D-hCγ1, carries nucleotide sequences encoding the natural D segment. In each plasmid, the nucleotide sequences encoding the HIV peptide and surrounding regions were determined and confirm their insertion in the correct frame.

Expression of these [murine 91A3V$_H$]-[human γ1 constant region] heavy chain genes with a [murine 91A3V$_L$]-[human K constant region] light chain was accomplished as follows: The 8 kb BamHI fragment encoding the entire 91A3 light chain gene as described in Sanz et al., Proc. Natl. Acad. Sci. U.S.A. 84, 1085–1989 (1987) was subcloned into the BamHI site of pUC19 plasmid. Subsequently, a Hind III fragment encompassing the light chain promotor and the variable region coding sequences was cut out from this plasmid and subcloned into the Hind III site of pSV184ΔHneoDNSV$_K$-hC$_K$ (upstream of the gene encoding a human kappa constant region) from which the dansyl V$_K$ (DNSV$_K$) was excised as described in Oi, V. T. & Morrison, S. C., Bio Techniques, 4 214–221 (1986). This plasmid which will encode a murine 91A3 V$_K$-human C$_K$ light chain is designated pSV184ΔHneo91A3$_K$-hC$_K$. Gene cloning, plasmid purification, hybridization, and DNA fragment separation and elution from agarose gels were carried as described in Zaghouani et al., J. Immunol., 148, 3604–3609 (1992). Nucleotide sequencing was carried out by the dideoxy method using a Sequenase kit available from U.S. Biochem according to the manufacture's instructions. The plasmids pSV2ΔHgpt91A3V$_H$-V$_3$C-hCγ1, pSV2ΔHgpt91A3V$_H$-V$_3$M-hCγ1, pSV2ΔHgpt91A3V$_H$-D-hCγ1, were separately cotransfected with pSV184ΔHneo91A3V$_K$-hC$_K$ into the non-Ig secreting murine myeloma B cell line, SP2/0, by electroporation (220 volts, 960 μFarads) as described in Zaghouani et al., J. Immunol., 148, 3604–3609 (1992) and Zaghouani et al., Science, 259, 224–227 (1993). Transfectants expressing both heavy and light chains were doubly selected using mycophenolic acid and geneticin as described in Zaghouani et al., 1992, J. Immunol. 148:3604–3609.

8.2. Results

Immunochemical properties of Ig-peptide chimeras

Plasmids pSV2ΔH-gpt-91A3V$_H$-hCγ1, pSV2ΔII-gpt-91A3V$_H$-V$_3$C-hCγ1, and pSV2Δ11-gpt-91A3V$_H$-V$_3$M-hCγ1 were separately cotransfected with pSV184ΔH-neo-91A3V$_k$-hC$_k$ into the non-Ig secreting murine myeloma B cell line, SP2/0, and Ig producing transfectants were doubly selected using G418 and mycophenolic acid. As indicated in FIGS. 7A–7C, three different Ig molecules were generated in which the heavy and light chain variable regions are of the murine 91A3 anti-arsonate antibody while the constant regions are derived from human γ1 and kappa chains. Ig-V$_3$C carries V$_3$C peptide in place of the D segment within the CDR3 loop of the V$_H$ gene, and Ig-V$_3$M carries V$_3$M peptide in place of the D segment. Ig-W is a control molecule encoded by unmodified genes, and therefore carries the parental D segment. These Igs were affinity purified on anti-human kappa mAb column and assayed for chain assembly and HIV peptide expression. When Ig-V$_3$C, Ig-V$_3$M and Ig-W are captured by an anti-human kappa mAb, they bind $^{125}$I-goat anti-human Fcγ1 antibodies to the same extent indicating that the replacement of the D segment with V$_3$C and V$_3$M preserved the Ig structure without affecting chain assembly or the overall folding of the molecule (FIG. 7D). The control molecule Ig-HA which is entirely murine Ig did not bind to anti-human antibodies. Furthermore, Ig-V$_3$C and Ig-V$_3$M but not Ig-W or Ig-HA bind rabbit antibodies specific for either V$_3$C (FIG. 7E) or V$_3$M (FIG. 7E) peptides. These results indicate that V$_3$C and V$_3$M peptides borne by Ig-V$_3$C and Ig-V$_3$M, respectively, are exposed and preserved their antigenicity when expressed in the CDR3 loop of Ig.

Induction of HIV-1 neutralizing antibodies in baboons immunized with chimeric Igs. Groups of baboons were immunized with either Ig-V$_3$C, Ig-V$_3$M, or control Ig-W and serum samples collected before and after immunization were tested for the presence of antibodies to V$_3$C and V$_3$M peptides and to a negative control peptide, 519–535 corresponding to the conserved amino acid residues 519–535 of HIV-1 111B isolate. The results of representative baboons are illustrated in FIGS. 8A, 8B and 8C. Baboons that were immunized with either Ig-V$_3$C, or Ig-V$_3$M produced antibodies to the gp120 V$_3$ loop derived peptides while those immunized with Ig-W did not. These antibodies are specific for V$_3$ peptides and did not bind 519–535 peptide. While Ig-V$_3$M induced antibodies that react only with V$_3$M peptide, Ig-V$_3$C induced cross-reactive antibodies that bind to both V$_3$M and V$_3$M peptides. A significant level of antibodies was detectable at day 65 (14 days after the third immunization). However, higher antibody levels were obtained at day 164 (14 days after the fifth immunization). While antibodies from rabbits immunized with V$_3$C-KLH or V$_3$M-KLH conjugates react with both V$_3$C and V$_3$M peptides, the antibodies from the baboon immunized with Ig-V$_3$M react only with V$_3$M peptide. This may be related to individual variation in the response, to a different folding of V$_3$M peptide in Ig-V$_3$M versus in V$_3$M-KLH conjugate and/or to a weaker response of the baboon probably due to poorer T cell help.

In further experiments we investigated whether these serum antibodies from baboons immunized with Ig-V$_3$ chimeras could bind native HIV-1 gp120 envelope protein. The results depicted in FIG. 9, indicate that serum from baboons immunized with either Ig-V$_3$C, or Ig-V$_3$M bind a 120 kd protein when incubated with MN virus lysates as does the control human serum from HIV-1 infected individual. A rabbit anti-serum raised against peptide 503–535 binds to the envelope protein of both MN and IIIB isolates, while the baboon serum did not bind to gp 120 of IIIB isolate. No binding to either MN or IIIB proteins is obtained when the lysates are incubated with serum from a baboon immunized with Ig-W. These results indicate that immunization of baboons with Ig-V$_3$C and Ig-V$_3$M induces antibodies that bind native envelope protein of HIV-1.

To investigate the effect that baboon anti-serum could have on HIV-1 virus infection of susceptible cell lines we carried out in vitro neutralization assays using MN and IIIB isolates as infectious material and Sup T1 as target cells. As can be seen in FIGS. 10A and 10B, anti-serum (bleed day 164, 14 day after the fifth immunization) from baboons immunized with either Ig-V$_3$C or Ig-V$_3$M neutralize HIV-1 MN but not IIIB isolate, while anti-serum from a baboon immunized with Ig-W failed to neutralize any of the two isolates. Significant HIV-1 MN neutralizing activity was detected in samples collected at days 101 (36 days after the third immunization), 136 (14 days after the fourth immunization, and 164 (14 days after the fifth immunization). The dose effect relationship between neutralization and serum dilution indicates that neutralization is dependent of the amount of serum antibodies.

Figure 11A:
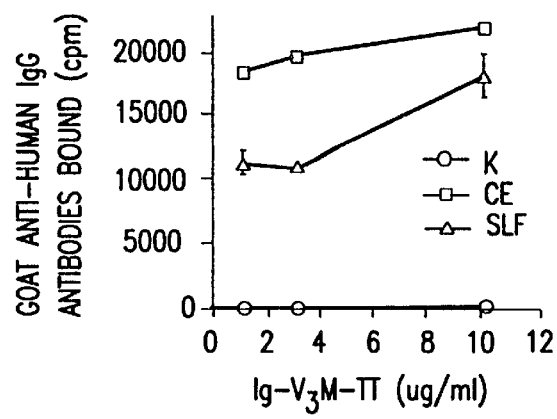
Figure 11B:
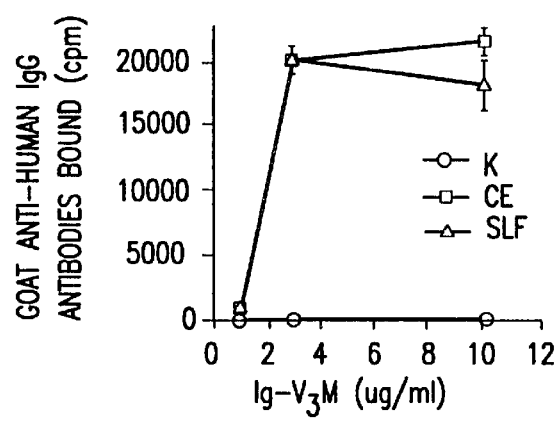
Figure 11C:
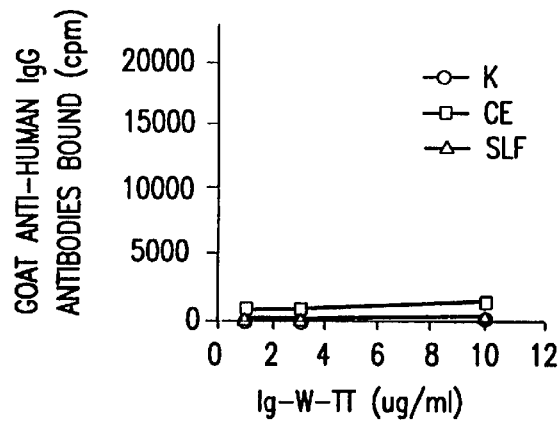
Figure 11D:
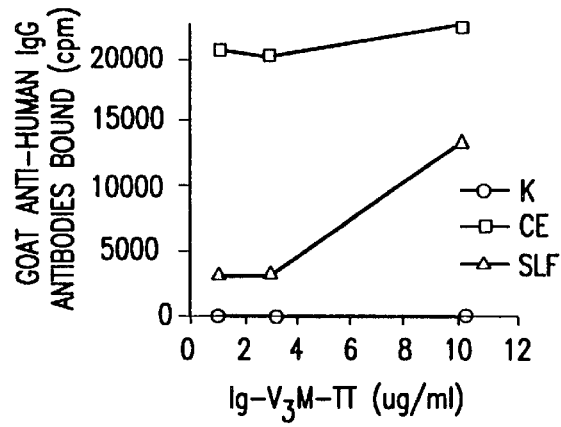
Figure 11E:
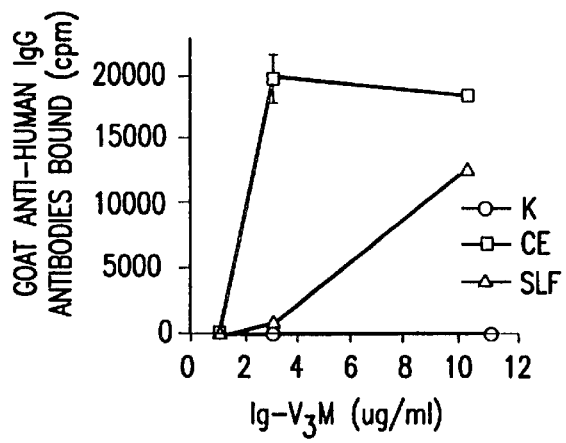
Figure 11F:
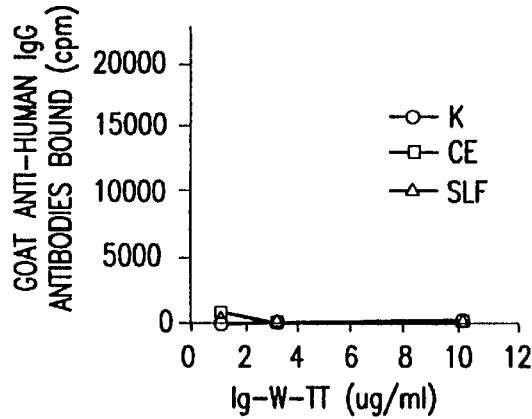
Figure 11G:
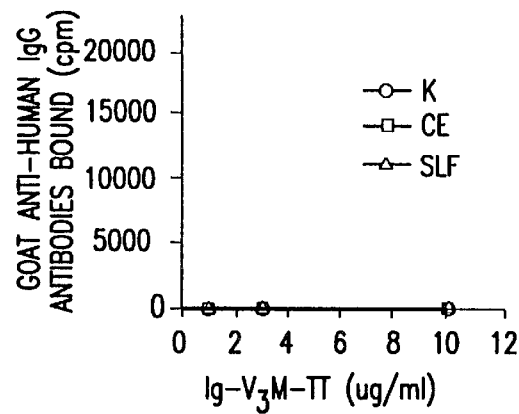
Figure 11H:
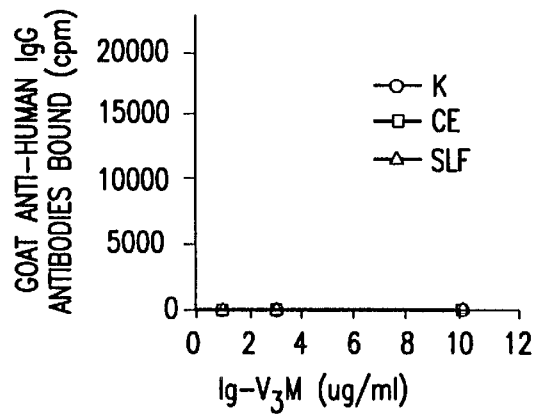
Figure 11I:
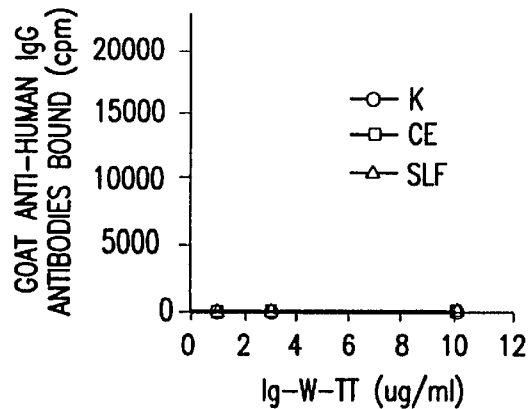

In vitro production of antibodies specific for HIV-1 derived peptides by human lymphocytes stimulated with Ig-peptide chimeras. Since Ig-peptide chimeras carrying HIV-1 envelope derived epitopes were able to induce HIV-1 neutralizing antibodies in baboons, we carried out in vitro experiments to determine whether human lymphocytes could similarly produce anti-HIV-1 antibodies subsequent to in-vitro stimulation with the chimeras. In preliminary experiments we tested serum from 20 HIV-1 infected asymptomatic patients for presence of antibodies that specifically react with V$_3$M and V$_3$C peptides. Among these, 9 individuals had antibodies that bound both HIV-1 envelope derived V$_3$M and V$_3$C peptides (not shown). Two of these individuals, CE and SLF, and one non-infected, healthy subject control were selected for study. Peripheral blood mononuclear cells (PBMC) from these individuals were incubated with the Ig-peptide chimeras either coupled or uncoupled to tetanus toxoid (TT) for a period of 7 to 10 days and culture supernatants were assayed for presence of antibodies to HIV-1 derived peptides. As indicated in FIGS. 11A to 11I, when lymphocytes from patients were incubated with either Ig-V$_3$-TT or Ig-V$_3$, they produced antibodies that bound to both V$_3$M and V$_3$C peptides (FIGS. 11G and 11H). Incubation with Ig-W did not stimulate the production of antibodies specific for the HIV-1 derived peptides (FIGS. 11C and 11F) indicating a specific stimulation of lymphocytes by the HIV-1 peptide borne by the Ig chimeras. Lymphocytes from the non infected subject (K), did not produce any detectable antibody to the HIV-1 derived peptides indicating that the cells producing the HIV-1 specific antibodies are memory cells that have previously been primed to respond to these epitopes. Optimal antibody production required lower amounts of antigen when the chimeras were coupled to TT suggesting that mobilization of TT specific T cells may have provided help for antibody production.

9. EXAMPLE: DERIVATIZATION OF CHIMERIC IMMUNOGLOBULINS WITH PEG

9.1. Materials and Methods

Mice. Six week old BALB/c mice were purchased from Jackson Laboratory (Harbor, Me.).

Antigens. The synthetic peptide HA110–120 (SFERFEIFPKE) (SEQ ID NO: 17) corresponds to amino acid residues 110–120 of HA of PR8 influenza A virus (Zaghouani et al., 1993, Science 259:224), NP 147–161 (TYQRTRALVRTGMDP) (SEQ ID NO: 15) corresponds to residues 147–161 of NP of PR8 influenza A virus (Zaghouani et al., 1992, J.Immunol., 148: 3604.) and V$_3$C peptide (RKSIHIGPGRAFYTTGEII) (SEQ ID NO: 1) corresponds to a consensus sequence predicted from the comparison of the $V_3$ cysteine bridged loop sequences of gp120 envelope proteins of 245 HIV-1 isolates (see above). Peptides were synthesized and RP-HPLC purified at IAF Biochem (Laval, Quebec, Canada). KLH and BSA conjugates of the synthetic peptides were prepared using standard techniques.

Ig-HA and Ig-$V_3$C were genetically engineered in our laboratory as described above. Ig-HA is a BALB/c IgG2b expressing in the CDR3 loop a T cell epitope (HA110–120) from the HA of PR8 influenza A virus. Ig-NP, is also a BALB/c IgG2b expressing in CDR3 loop the NP147–161 CTL-epitope. Ig-$V_3$C is a mouse variable-human γ1/k constant regions expressing within the heavy chain CDR3 loop a B cell epitope from the $V_3$ cysteine bridged loop of the envelope protein of HIV-1. Ig-W, is the wild type mouse $V_H$ and $V_L$ variable-human γ1/k constant regions used as a control for Ig-$V_3$C. Ig-HA and Ig-NP, were affinity purified from culture supernatant on a rat anti-mouse k chain-sepharose column. Ig-$V_3$C and Ig-W were affinity purified on a mouse anti-human k chain antibody (HP605)-sepharose column.

PR8 influenza A virus was prepared from allantoic fluid of embryonated eggs on a sucrose gradient. An UV inactivated PR8 virus was used in these experiments.

Derivatization of Chimeric Ig with mPEG

Ig-HA, Ig-NP, and Ig-$V_3$C (see above) were derivatized with 2,4,6-trichloro-s-triazine activated mPEG 5,000 (Sigma) and purified to homogeneity. Briefly, a 50 times molar excess of mPEG was added to 10 mg of chimeric Ig in 10 ml of 0.1 M tetraborate buffer, pH 9.6. The mixture was stirred vigorously for four hours at room temperature and the preparations were concentrated to 1.5 ml in CENTREX UF-2 ultraconcentrators of 100,000 MWCO (Schleicher & Schuell). The residual unreacted mPEG was removed by size exclusion chromatography on AcA44 Ultrogel column and homogeneous populations of Ig-mPEG with 6–8% derivatized lysines were isolated by anion exchange HPLC on Q300 column (for details of procedure, see Example Section 10, below). The degree of mPEG derivatization was estimated by fluorescamine assay as described (Cunningham-Rundles et al., 1992, J.Immunol.Methods 152: 177). Briefly, graded amounts (0.25, 0.5 and 1 $\mu$g) of Ig-HA-mPEG, Ig-$V_3$C-mPEG conjugates and native Ig-HA or Ig-$V_3$C, were dissolved in 25 $\mu$l of PBS and mixed with an equal volume of fresh fluorescamine in acetone (150 g/ml). Samples were incubated for 5 min at room temperature and then adjusted to 1 ml with PBS. The absorbance was then measured at 475 nm emission versus 390 nm excitation and the percent of pegylated lysines was estimated according to the following formula I-($OD_{475}$ Ig-mPEG/$OD_{475}$ native Ig)x1OO. The homogeneity of the conjugates was confirmed by SDS-PAGE and agarose electrophoresis.

Blood circulation. Ig-HA and Ig-HA-mPEG preparations (100 $\mu$g in 100 $\mu$l of PBS) were radiolabeled with $^{125}$I using the chloramine method and the free iodine was then removed by gel filtration on PD10 columns (Pharmacia). Groups of three BALB/c mice were injected i.v. with 200 $\mu$l of PBS containing 20x$10^6$ cpm (4 $\mu$g) of $^{125}$I-labeled native Ig-HA or Ig-HA-mPEG. Fifteen minutes later (time required for uniform distribution of labeled Ig) the mice were bled and the radioactivity in 20 $\mu$l of serum was counted. Total radioactivity per mouse was estimated on the basis that 7.3% of body weight is blood and 55% of the blood volume is serum (Klibanov et al., 1991, Biochim.Biophys.Acta 1062: 142). The radioactivity estimated at 15 min was considered as the total radioactivity injected. To investigate the clearance of Ig-HA and Ig-HA-mPEG, mice were bled 3, 6, 24, 48, 72, and 168 hours after injection. Blood clearance rates were expressed for each group as percentage of residual radioactivity at various intervals of time.

Organ distribution. To study the tissue distribution of the native Ig-HA and Ig-HA-mPEG conjugates, two groups of seven mice each (15–17 g weight) were injected i.v. with 200 $\mu$l PBS containing 20x$10^6$ cpm of $^{125}$I-labeled native Ig-HA or Ig-HA-mPEG. Mice were bled after 15 min and the blood radioactivity was estimated as above. Fragments of liver, spleen, lung and kidney were then resected by 3, 6, 24, 48, 72, and 168 hours after inoculation and the radioactivity was measured in a γ counter. Tissue distribution was expressed as index of distribution (% ID) of $^{125}$I-Ig-HA or $^{125}$I-Ig-HA-mPEG. ID represents the percentage of radioactivity per gram of wet organ versus the radioactivity measured in blood at 15 min after injection (Kitamura et al., 1990, Biochem. Biophys. Res. Commun.: 1387).

Western blot analysis. To investigate in vivo proteolysis of the native and pegylated Ig-HA, blood samples from mice injected with $^{125}$I-Ig-HA or $^{125}$I-Ig-HA-mPEG as for the clearance studies, were analyzed by SDS-PAGE under non reducing conditions. Briefly, serum samples (5 $\mu$l) collected at various intervals of time were electrophoresed on 8 to 17% polyacrylamide gradient gels (ExcelGels, Pharmacia) for 2 hours, at 150 volts and 40° C. using a Multiphore II system (Pharmacia). Separated proteins were electrotransferred from the gel onto PVDF membranes (0.22$\mu$, Millipore, Waters Co.) for 30 minutes at 450 mAmps. Membranes were dried and exposed to Kodak X-OMAT films overnight at −70° C.

In vitro T cell proliferation assay. 2PK3 B lymphoma cells (H-2d) were used as APCS. Irradiated (2,200 rads) APCs ($10^4$) were incubated for 48 hours in round bottom 96-well plates with graded amounts of Ig-HA, Ig-HA-mPEG or Ig-NP-mPEG, and 2x$10^4$ of HA110–120 specific T hybridoma cells LD1–24 (Haberman et al., J. Immunol. 145:3087). Supernatants were then harvested and IL-3 production as a measure of T cell proliferation was determined using 1.5x$10^4$ of IL-3 dependent DA- I cells and the calorimetric MTT assay (Zaghouani et al., Science 259:224, Mosmann, 1983, J. Immunol. Methods 65: 55).

In vivo T cell proliferation assay. The proliferative response of lymph node cells from BABL/c mice immunized with IG-HA or Ig-HA-mPEG were assessed for [$^3$H]-thymidine incorporation. Four groups of seven mice each were immunized subcutaneously at the base of the tail and in the foot pads with 100 $\mu$g of Ig-HA or Ig-HA-mPEG emulsified in either 200 $\mu$l of PBS or 200 $\mu$l of PBS/CFA (1:1 v/v). Ten days later, the draining lymph nodes were collected and the cells were cultured in flat bottom 96-well microtiter plates (2x$10^5$ cells per well) with 0.5, 1, 5, and 10 $\mu$g/ml of HA110–120, NP147–161, Ig-HA, Ig-NP, UV-inactivated PR8 virus, ConA (1 $\mu$g/ml) or no antigen. Cultures were set up in quadruplets from pooled lymph node cells, incubated under standard conditions for 5 days (or 3 days in the case of ConA), and pulsed for the last 18 hours with 1 $\mu$Ci of [$^3$H]-thymidine per well. The cells were then harvested and the radioactivity was measured in a P scintillation counter. The mean of cpm obtained in the absence of antigen was subtracted from the mean of cpm obtained in the presence of antigens.

Radioimmunoassay. Detection of the anti-$V_3$C peptide antibodies in mice sera was carried out by radioimmunoassay as follows: microtiter plates were coated with 50 µl of PBS containing 5 µg/ml of $V_3C$ peptide coupled to BSA ($V_3C$-BSA), BSA, or NP147–161-BSA for 18 hours at 40° C. The plates were extensively washed with PBS and then blocked with 3% BSA in PBS at room temperature. After 4 hours the plates were washed with PBS and serial serum dilutions (50 µl) in 1% BSA-PBS were added. The plates were incubated for 2 hours at 37° C. After washing with PBS-0.05% Tween 20, bound antibodies were revealed by incubating the plates for 2 hours at room temperature with $5\times10^4$ cpm of $^{125}$I-rat anti-mouse k chain mAb. Plates were then washed and bound radioactivity was measured in a γ counter. The amount of anti-$V_3C$ antibodies in mice sera was estimated by extra-polation on a standard curve constructed with affinity purified mouse polygonal anti-$V_3C$ antibodies. These polyclonal anti-$V_3C$ antibodies were obtained from BALB/c mice immunized with $V_3C$-KLH conjugate (100 µg) in CFA and then boosted weekly, three times with $V_3C$-KLH conjugate (50 µg) in incomplete Freund adjuvant (IFA). The antibodies were affinity purified on a $V_3C$-BSA-sepharose column.

Detection of anti-human isotypic antibodies in mice sera was carried out by radioimmunoassay as follows: microtiter plates were coated with 50 µl of PBS containing 2 µg/ml of Ig-W for 18 hours at 40° C. The plates were then treated as above. The amount of mouse anti-human Ig antibodies was estimated by extrapolation on a standard curve constructed with a stoichiometric mixture of mouse anti-human γ1 mAb (Zymed Laboratory) and HP6053 mouse anti-human kappa mAb (ATCC).

9.2. Results

Preparation of homogeneous populations of pegylated Ig chimeras

Ig-HA and Ig-$V_3C$ were mildly pegylated and homogeneous conjugates with 6–8% mPEG substitution of the lysine residues were purified as described in Section 10, below. The conjugate preparations were rendered free of residual adducts such as free hydrolyzed mPEG and highly conjugated or unconjugated Ig by size exclusion chromatography performed on AcA44 Ultrogel column followed by anion-exchange HPLC on Q300 column. Homogeneous populations of Ig-HA-mPEG and Ig-$V_3C$-mPEG conjugates with 6–8% mPEG substituted lysine residues as determined by fluorescamine assay, were used for further investigations.

Blood clearance and tissue distribution of native and pegylated Ig chimeras

Clearance rates. The clearance rates of Ig-HA-mPEG from blood circulation were analyzed in parallel to those of the native Ig-HA. $^{125}$I-labeled Ig-HA-mPEG and Ig-HA were injected i.v. into BALB/c mice and the radioactivity was measured in blood samples collected at various intervals of time. As depicted in FIG. 12, the native Ig-HA was cleared at 48 hours after injection while lg-HA-mPEG persisted in peripheral blood up to 7 days. Ig-HA-mPEG showed a two phase clearance characterized by an initial rapid decline followed by a much slower decline.

Resistance to in vivo proteolysis. Serum samples from mice injected with $^{125}$I-labeled native Ig-HA or Ig-HA-mPEG were collected at various intervals of time and analyzed by Western blot analysis. Both native and pegylated Ig-HA showed important degradation between 6 and 24 hours after injection. By 48 hours, the majority of the proteolytic products were cleared from the blood, and by 72 hours intact Ig molecules were detected only in samples from mice injected with Ig-HA-mPEG (FIG. 13).

Tissue distribution. We carried out kinetic studies to estimate the amount of radioactivity in various tissues at various intervals of time after injection of the radiolabeled conjugates. The tissue distribution of $^{125}$I-Ig-HA and $^{125}$I-Ig-HA-mPEG was studied in liver, spleen, lung and kidney resected at 0.25, 3, 6, 24, 48, 72 and 168 hours after injection. As illustrated in FIG. 14, both Ig-HA and Ig-HA-mPEG are taken up by the various organs to the same extent but the amounts of Ig-HA-mPEG retained in the organs were higher than those of native Ig-HA. It should be noted that in lungs, while Ig-HA-mPEG was still present by 168 hours, the native Ig-HA was cleared by 72 hours. Overall, these results indicate that pegylated Ig-HA molecules persist longer than the native Ig-HA in the blood, and higher amounts of the pegylated Ig-HA were retained in organs with lymphoid tissues.

Figure 15:
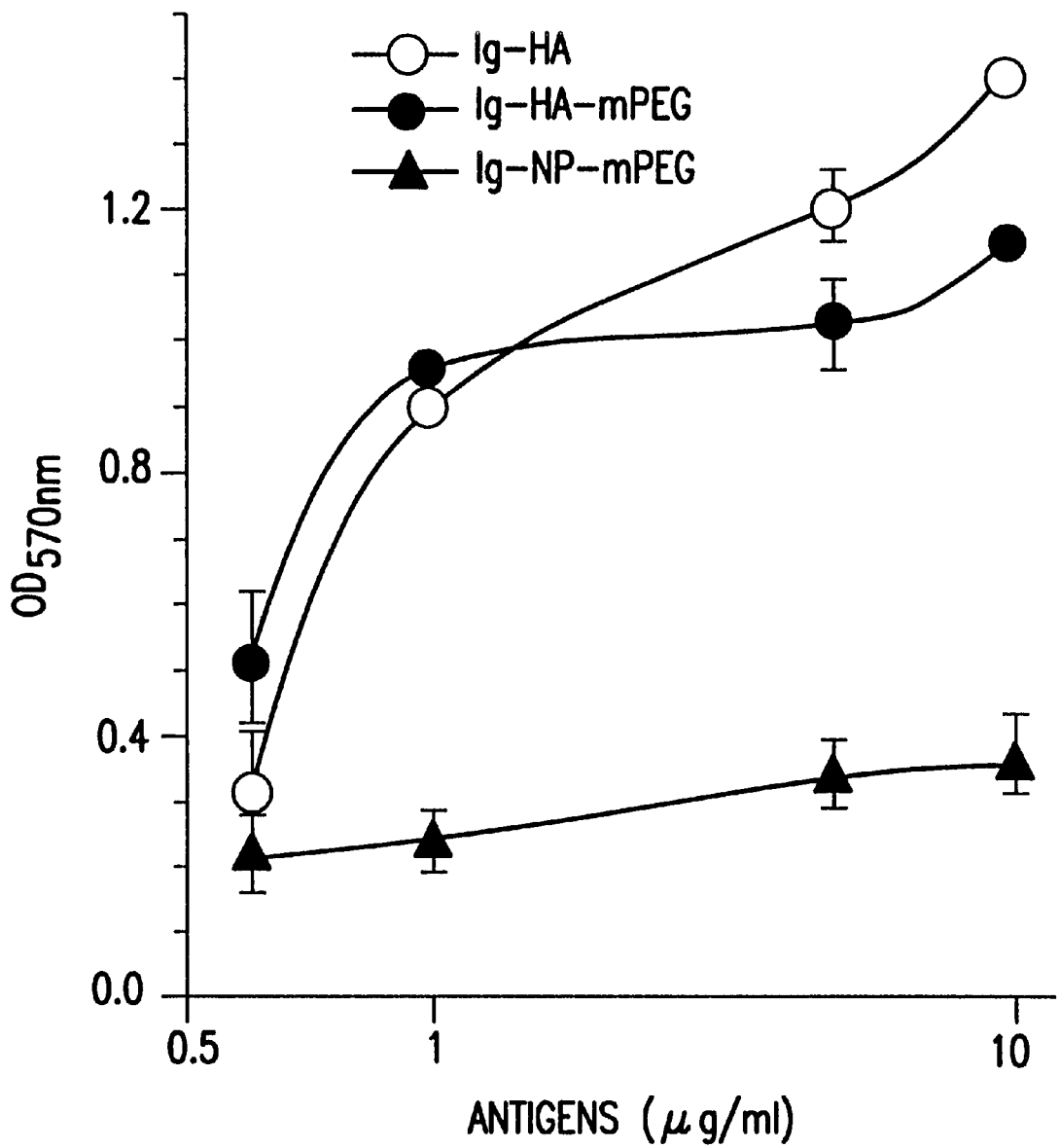

The cellular immune response to HA110–120 peptide expressed by pegylated Ig-HA chimera In vitro activation of HA110–120 specific T cell hybridoma. To assess the effect of mPEG derivatization on the immunogenicity of Ig-HA, we studied in vitro T cell activation by native Ig-HA and Ig-HA-mPEG. This was carried out using HA110–120 specific T hybridoma cells, LD1–24 and measurement of IL-3 release by these cells subsequent to activation by the various antigens. FIG. 15 shows that Ig-HA-mPEG activates the specific T cells to the same extent as native Ig-HA. This indicates that mPEG derivatization of the chimeric Ig did not affect the delivery and subsequent presentation of the HA100–120 peptide to the T cells. No activation was observed with pegylated Ig-NP, a molecule carrying a CTL epitope from NP of PR8 influenza A virus instead of the HA110–120 helper epitope.

Figure 16A:
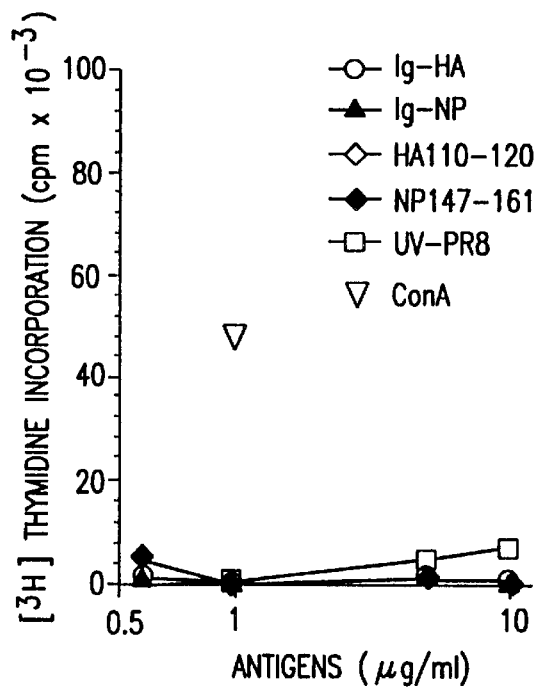
Figure 16B:
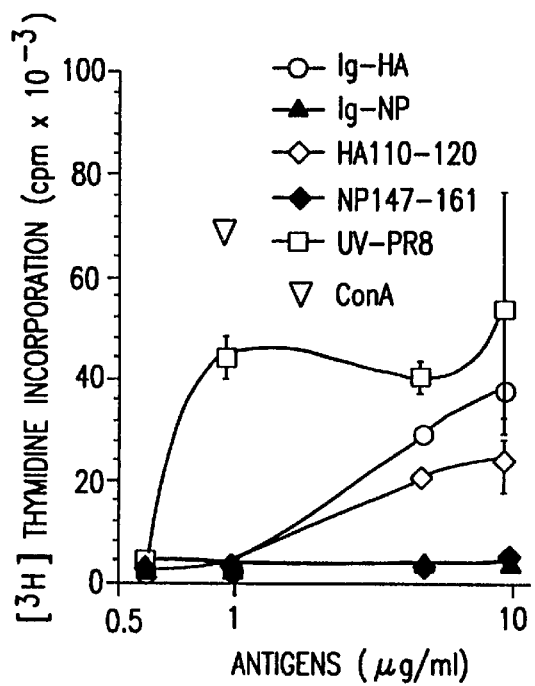

In vivo priming of HA110–120 specific T cells. In a previous work, we showed that immunization of BALB/c mice with Ig-HA in CFA primed animals to mount a specific proliferative response (Zaghouani, et al., 1993, Science 259:224). In this study, we compared the immunogenicity of native and pegylated Ig-HA administered in either saline or CFA (FIGS. 16A to 16D). Lymph node cells from BALB/c mice were harvested ten days after immunization and stimulated in vitro for 5 days with various antigens. Immunization with native Ig-HA in CFA primed T cells for in vitro proliferative response upon incubation with Ig-HA, UV-inactivated PR8 virus and HA110–120 peptide but not Ig-NP or NP 147–161 peptide (FIG. 16B). Similar responses were obtained when the mice were primed with Ig-HA-mPEG in CFA (FIG. 16D).

Figure 16C:
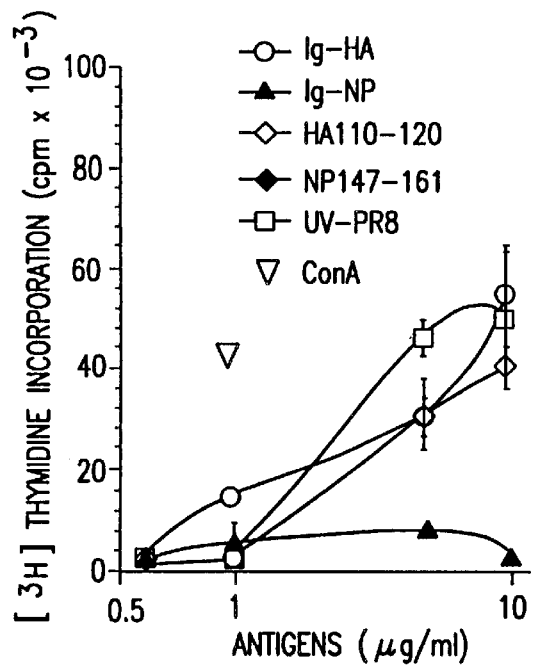
Figure 16D:
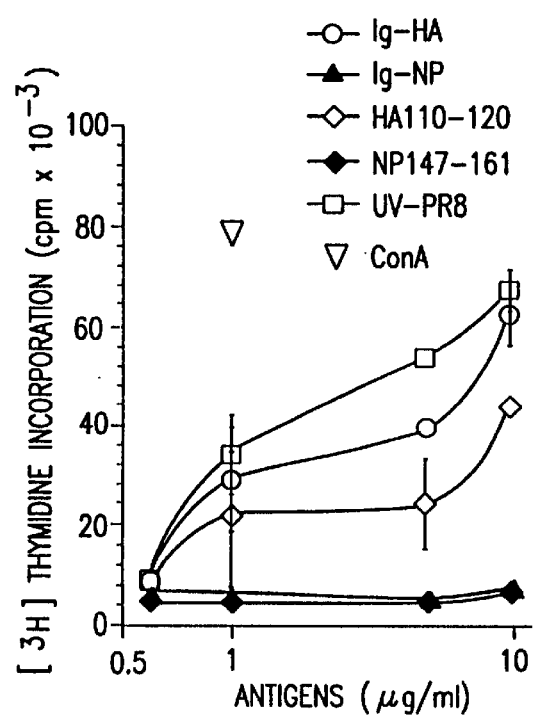

More striking, a strong and specific proliferative response was obtained when the mice were primed with Ig-HA-mPEG in saline (FIG. 16C). No response was detected when the mice were immunized with native Ig-HA in saline (FIG. 16A). This strongly suggest that the requirement for adjuvant was obviated when Ig-HA was derivatized with mPEG 5,000.

Figure 17A:
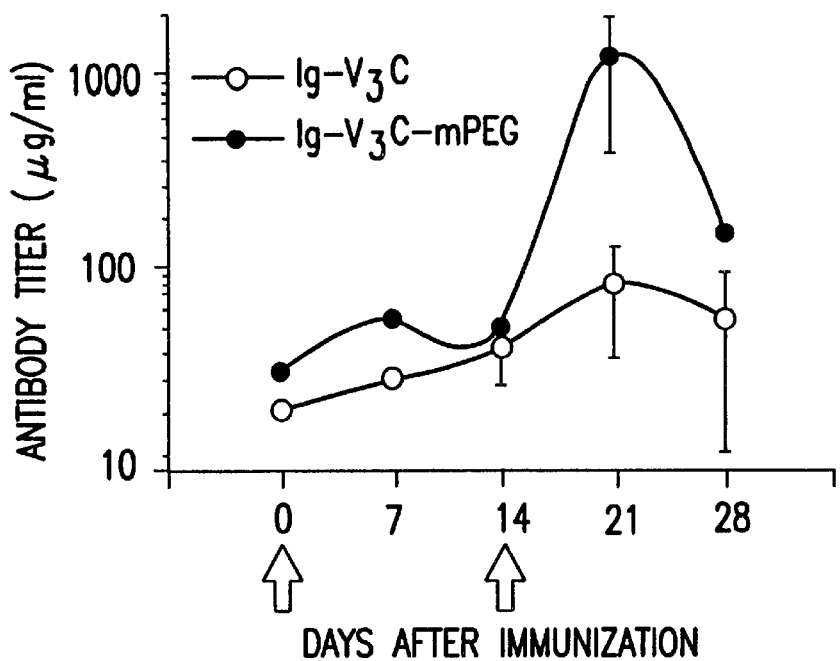

Effect of Ig-V3C derivatization with mPEG on the antibody response to $V_3C$ peptide and to Ig-xenogeneic determinants The kinetics of antibody response elicited by native and pegylated Ig-$V_3C$ was studied in BALB/c mice following different immunization schedules (see the legend for FIG. 17A). As mentioned above, Ig-$V_3C$ is a chimeric molecule made up of murine $V_H$ gene expressing the consensus $V_3C$ peptide, murine $V_k$ gene and human γ1 and κ constant region genes. Therefore, we measured by RIA the antibody response against the $V_3C$ epitope as well as against isotypic determinants of human constant regions.

Figure 17B:
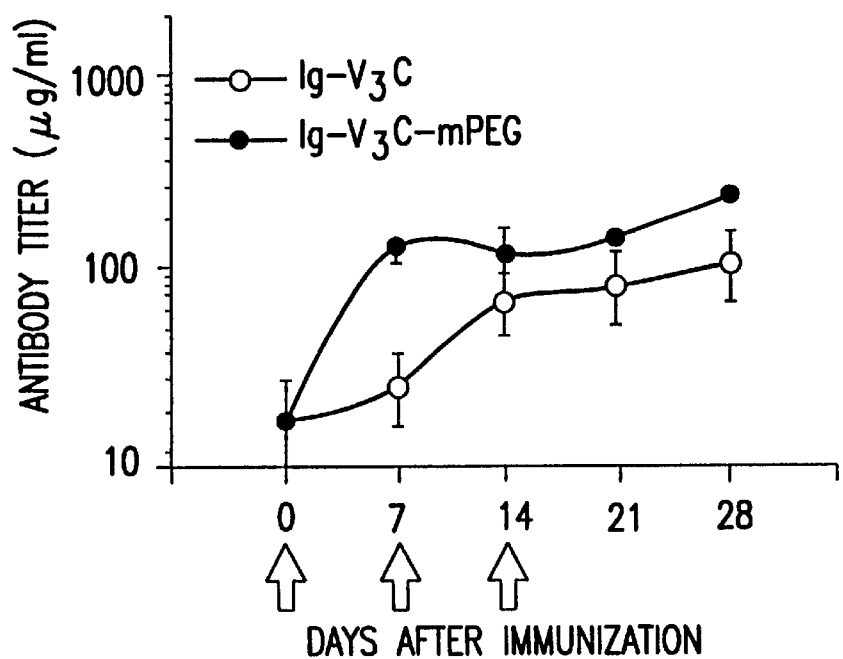
Figure 17C:
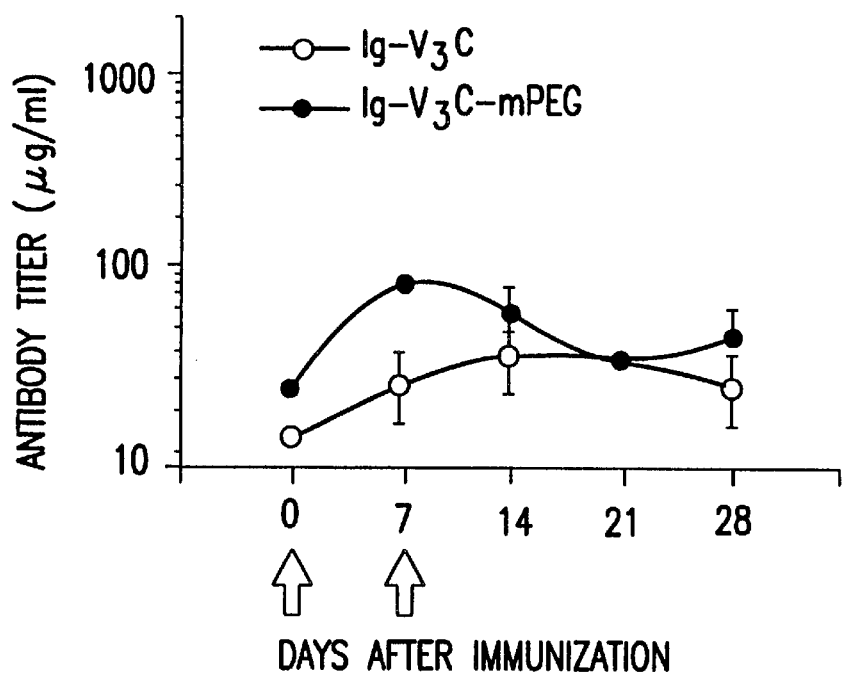
Figure 17D:
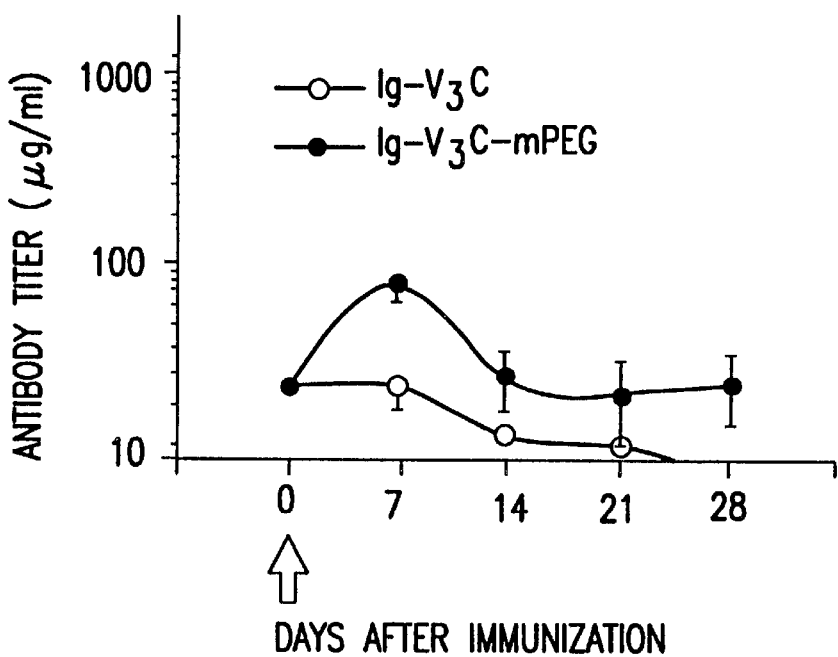

The study showed a sharp increase of the antibodies to $V_3C$ peptide after immunization with Ig-$V_3C$-mPEG in CFA followed by a boost in IFA (FIG. 17A). More importantly, immunization of animals with Ig-$V_3C$ or Ig-$V_3C$-mPEG in saline induced a $V_3C$ specific antibody response (FIGS. 17B, 17C and 17D). This response was slightly higher in animals immunized with Ig-$V_3$C-mPEG. The antibody response was stronger when the animals were immunized 3 times in saline (FIG. 17B versus FIGS. 17C and 17D).

Figure 17E:
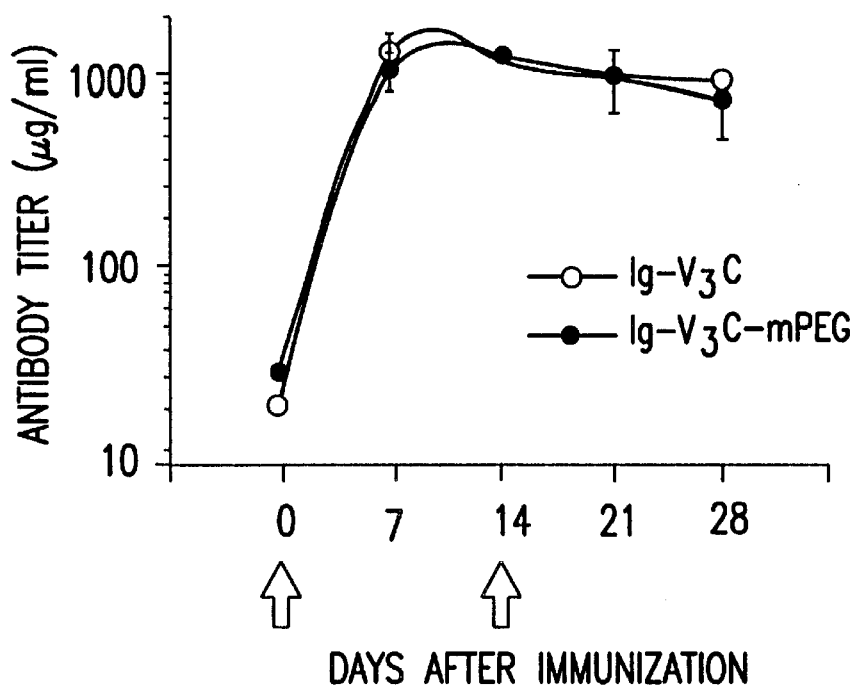
Figure 17F:
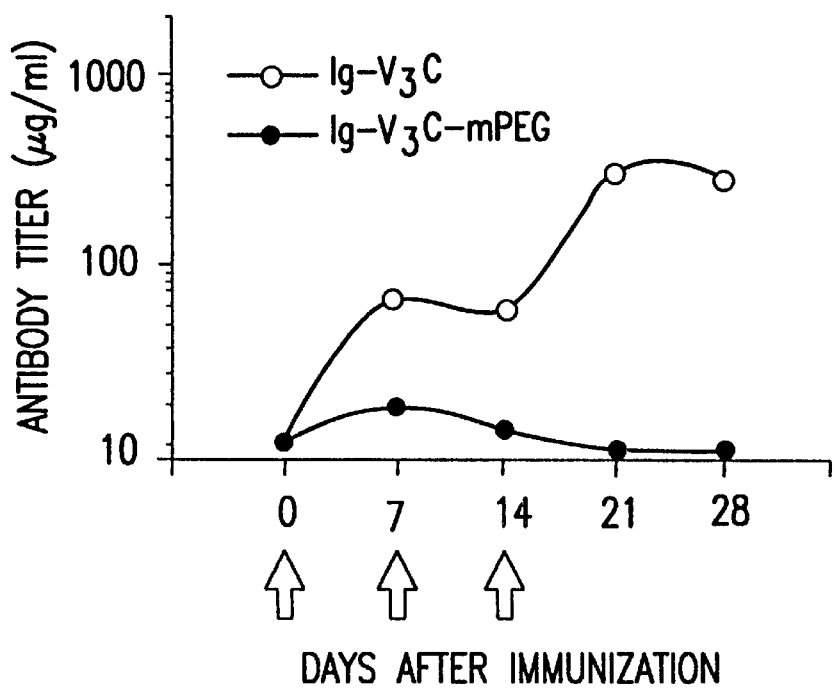
Figure 17G:
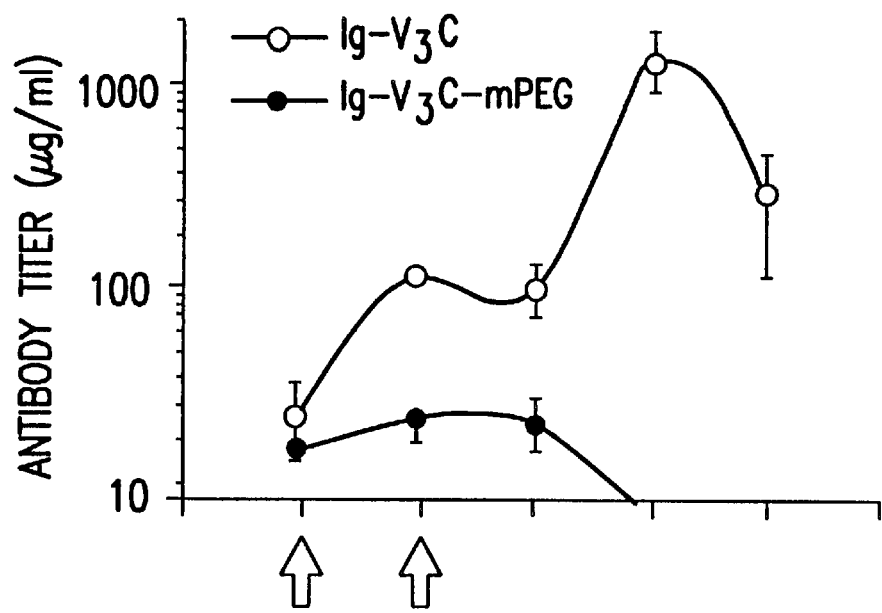
Figure 17H:
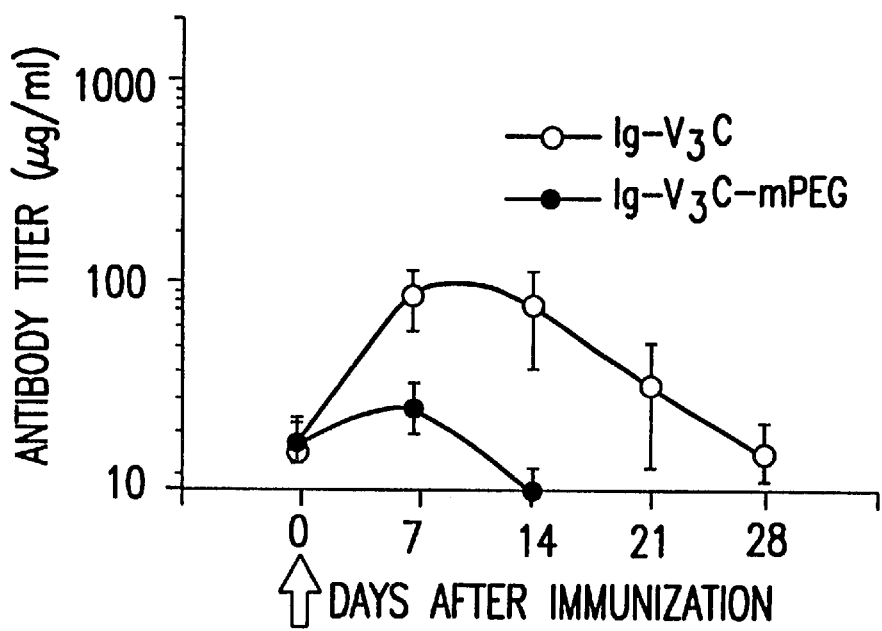

The animals immunized with native chimeric Ig in CFA showed high antibody response to isotypic determinants of human constant regions (FIG. 17E). However, while immunization in saline with native Ig-$V_3$C also induced a strong anti-human antibody response, immunization with Ig-$V_3$C-mPEG in saline elicited no significant response (FIGS. 17F, 17G and 17H).

10. EXAMPLE: PURIFICATION OF PEGYLATED IMMUNOGLOBULIN

During pegylation of a protein, various degrees of derivatization may occur as a consequence of the micro heterogeneity of the protein, the distribution of both the number and the position of attachment of PEG units, the inherent polydiversity of PEG polymers, and microenvironmental conditions of the reaction. In addition, dioxy PEG that can crosslink proteins may be present in commercial preparations as a result of hydrolysis of the ethylene oxide monomers during the polymerization process (Selisko et al., 1993, J. Chromatogr. 641: 71–79; Harris et al., 1985, in "Partitioning in Aqueous Two-Phase Systems", D. E. Brooks and D. Fisher (Editors), Academic Press, Orlando, Fla., p.593). Thus, protein-mPEG preparations may contain species of highly pegylated and/or crosslinked proteins in addition to the residual adducts. Purification of homogeneous populations of conjugates is therefore required prior to their use in biological systems. Purification of protein-PEG conjugates has generally consisted of a single step chromatographic removal of free PEG polymers (Kitamura, et al., 1991 Cancer Res., 51: 4310–43115; Cunningham-R. A. et al., 1992, J. Immunol. Methods, 152: 177–190; Snider et al., 1992, J. Chromatogr. 599: 141–155; Jackson, et al., 1987, Anal-Biochem. 165:114–127). Herein, we describe a two step procedure able to remove completely the residual adducts and to isolate homogeneous populations of mPEG derivatized immunoglobulins.

10.1. Materials and Methods

Chemicals

AIgs (Ig-HA and Ig-$V_3$C) were generated in our laboratory as described above. PhastSystem electrophoresis apparatus, PhastGels 4–15% gradient of polyacrylamide and cyanogen bromide activated Sepharose CL-4B were purchased from Pharmacia, LKB. AcA44 Ultrogel and dialysis bags of 75,000 MWCO were from Spectrum, Co. Ultra concentrators of 100,000 MWCO (CENTREX UF-2, 2 ml volume) were from Schleicher & Schuell. Rat hybridoma cells secreting monoclonal anti-murine k chain antibodies and HP6053 mouse hybridoma producing anti-human k chain antibodies were from ATCC. The Q300 HPLC column (250×4.6 mm, 300 micron particle size) was from Rainin. Nessler reagent and 2,4,6-trichloro-s-triazine activated monomethoxypolyethlene glycol MW 5,000 (mPEG 5,000) were from Sigma. The agarose gels (Titan Gel High-Resolution Protein kit) were from Helena Laboratories.

Experimental

Purification of AIgs. IgHA and Ig-$V_3$C were affinity purified on a rat anti-murine k chain and mouse anti-human k chain antibody-Sepharose columns, respectively. Affinity purified AIgs were equilibrated in 0.1 M sodium tetraborate, pH 9.6 and concentrated to 1 mg/ml by ultracentrifugation using tubes of 100,000 MWCO.

Derivatization of AIgs with mPEG. 10 mg of each AIg were derivatized with 2,4,6-trichloro-s-triazine activated mPEG 5,000 as described in Jackson, et al., 1987, Anal-Biochem. 165:114–127. Briefly, a 50 times molar excess of mPEG was added to 10 mg AIgs in 10 ml of 0.1 M tetraborate buffer, pH 9.6. The mixture was stirred vigorously for four hours at room temperature. The conjugate preparations were concentrated to 1.5 ml in tubes of 100,000 MWCO and further purified.

Chromatographic purification of AIg-mPEG conjugates. AIg-mPEG preparations were applied on AcA44 Ultrogel filtration column (80×1.6 cm) equilibrated with 0.1 M $NH_4HCO_3$, pH 8.5 and flow rate of 0.4 ml/min. Fractions were collected at 4 min interval, dried by speed vacuum centrifugation and resuspended in 0.5 ml of 5 mM sodium-acetate, pH 5. Each fraction was then analyzed for protein content by Biuret micro assay, and for the presence of free hydrolyzed mPEG by Nessler's reagent as described (Wilkinson et al., 1987, Immunol.Lett. 15: 17–22). Fractions of the conjugates free of hydrolyzed mPEG were then rechromatographed on a Q300 anion-exchange HPLC column equilibrated with 5 mM sodium acetate, pH 5 using a 45 minutes linear gradient from 5 to 500 mM sodium acetate, pH 5, and flow rate of 0.5 ml/min. Fractions from Q300 column were dialyzed in Spectrapor bags with 75,000 MWCO against PBS and concentrated in CENTREX UF-2 tubes.

Electrophoretic analyses of AIg-mPEG conjugates. Homogeneity of AIg-mPEG conjugate was analyzed by SDS-PAGE and residual mPEG was detected by electrophoresis on agarose cels. The SDS-PAGE was performed in non reducing conditions as described by Laemmli (Laemmli, 1970, Nature (London), 227: 680–685). Briefly, Samples (5 $\mu$g) were resuspended in 5 $\mu$l of sample buffer (0.1% SDS, 0.1 M Tris-HC1 6 M urea, pH 8.5) and incubated at 37° C. for 2 hours. Samples were run on 4–15% gradient PhastGel (Pharmacia) at 250 Volts and 5 Watts for 45 minutes at 15° C. The gel was then fixed and silver stained. Electrophoresis on agarose Titan gels was carried out according to the manufacture's instructions. Samples (10 $\mu$g in 5 $\mu$l barbital buffer) were run at 250 Volts for 30 minutes on duplicate gels. One gel was stained with a mixture of 0.1% Coomassie Blue R-250 and 1% Ponceau S, and the second gel was immersed in 20% trichloroacetic acid (TCA) in water for 30 seconds and immediately photo-scanned.

Fluorescamine assay. Graded amounts (1, 0.5 and O25 $\mu$g) of AIg-mPEG or AIgs in 25 $\mu$l of PBS were mixed with equal volume of fresh fluorescamine in acetone (150 g/ml) and incubated for 5 min at room temperature. Samples were then brought to 1 ml with PBS and absorbency was measured at 475 nm emission versus 390 nm excitation. The percent of pegylated primary amines was estimated according to the following formula 1-($OD_{475}$AIgs-mPEG/$OD_{475}$AIgs)×1OO (Neville, et al., 1991, presented at the American Association of Pharmaceutical Scientists', Sixth Annual Meeting, Washington, D.C., Nov. 17–21, 1991). The improved resolution obtained with ammonium bicarbonate may be related to better neutralization of the active charges on gel matrix and therefore lower interactions between free mPEG polymer and the matrix.

Removal of other residual adducts from the AIg-mPEG conjugates. Because no one step procedure for the separation of protein-mPEG conjugates from residual adducts is described, we chose a method that includes a first step removal of hydrolyzed mPEG and a subsequent step that removes other residual adducts such as underivatized or highly derivatized AIgs. Since the size exclusion limit of the AcA44 Ultrogel column is 140 kD, hydrolyzed mPEG can be removed but the other residual adducts can not. The removal of excess PEG is required because it could interfere with the isolation of the conjugates from the other residual adducts in the subsequent anion exchange chromatography step. Preliminary experiments performed on anion-exchange HPLC columns as a single step of purification, showed poor resolution and low yields even if minimal amounts of sample were applied on the column. In fact, the conjugates showed a broad elution profile as a result of the presence of excess of free polymers which interfere strongly with the binding of conjugates to the anion-exchange matrix. Poor resolution of pegylated proteins was also described when conjugates were separated by charge-reversal capillary zone electrophoresis without previous removal of free PEG (Snider et al., 1992, J. Chromatogr. 599: 141–155; McGoff, et al., 1988, Chem.Pharm.Bull. 36: 3079). It may be important to remove free polymer from the conjugate preparation in order to obtain good resolution in different separating media.

Figure 18A:
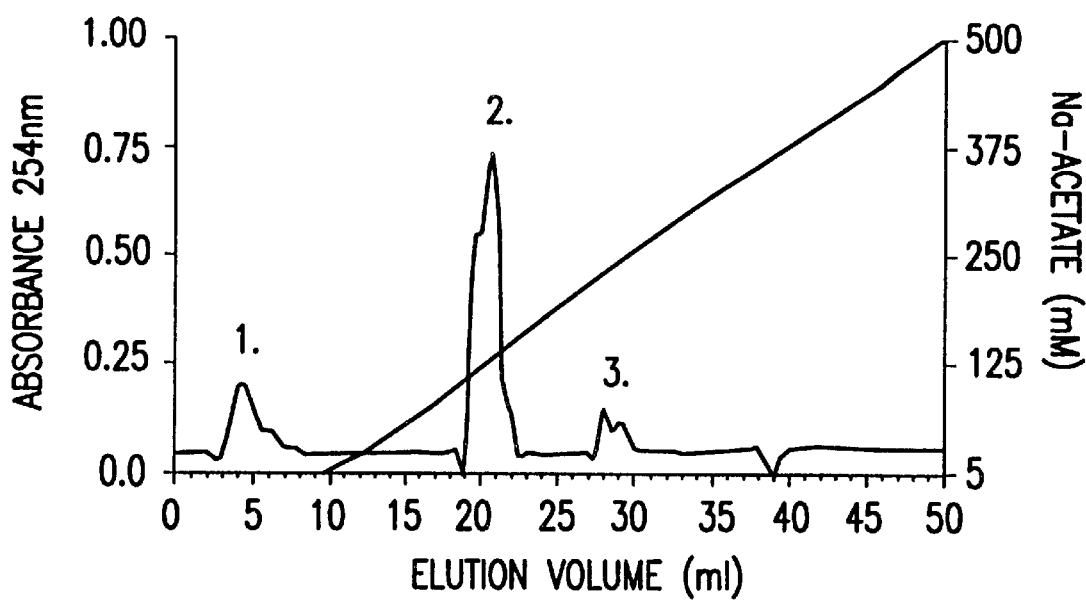
Figure 18B:
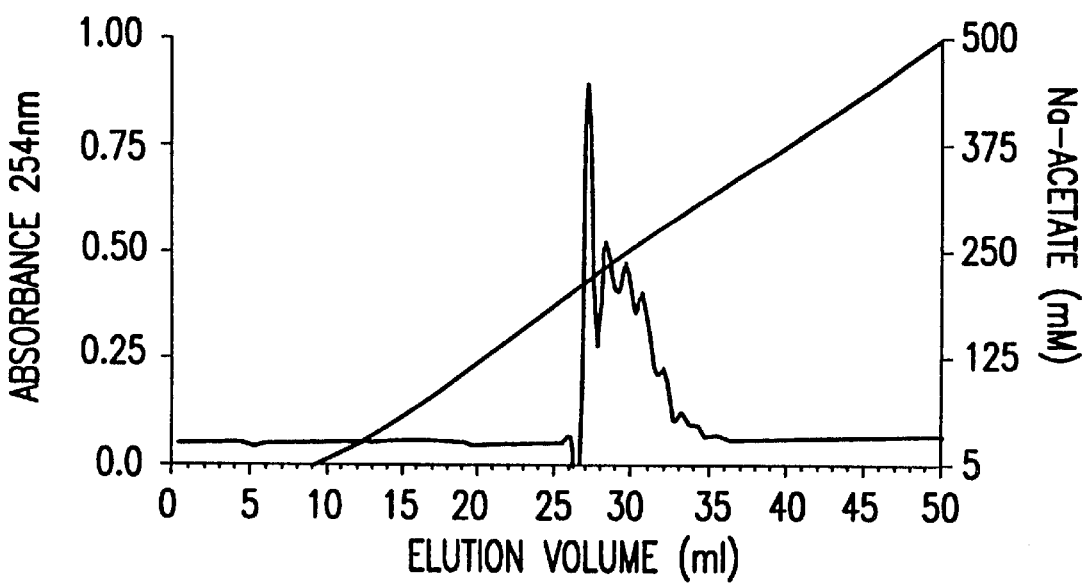

To select homogeneous population of conjugates with 6–8% degree of pegylation, we rechromatographed the conjugates on anion-exchange HPLC column with optimized conditions as described in the experimental section. FIG. 18 shows the elution profiles of Ig-HA-mPEG (FIG. 18A) and free IG-HA (FIG. 18B). In the case of Ig-HA-mPEG, 3 major peaks were eluted from the column and labeled 1, 2, and 3 (FIG. 18A). Peak 3 represents free Ig-HA since it elutes at the same salt concentration as the unconjugated control Ig-HA. The material of peak 1 may represents highly pegylated AIgs that could not bind to the matrix. Peak 2 seems to contain mildly pegylated Ig-HA as revealed by SDS-PAGE analysis (see below).

Figure 19:
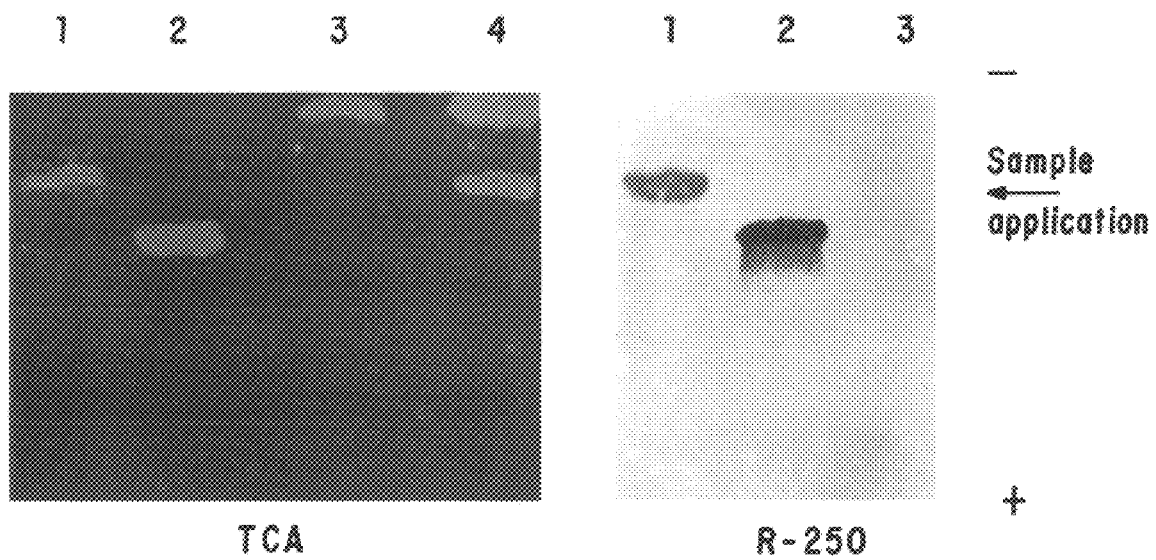

Analysis of the homogeneity of AIg-mPEG conjugates. The purity of AIgs-mPEG preparations was further analyzed for the presence of traces of free mPEG and residual adducts performed on agarose and polyacrylamide gel electrophoresis, respectively. Although purification of AIgs-mPEG conjugates followed one step purification by size exclusion chromatography, small amounts of free mPEG that could not be detected by Nessler's test may be present in the conjugate preparations. To trace small amounts of free PEG that could interfere with the immunogenicity of the AIgs-mPEG we developed an original, sensitive electrophoretic technique able to detect $\mu$M of free mPEG. Based on the observation that mPEG migrate on agarose to the cathode and can be visualized by TCA precipitation but not by protein dyes, we attempted to trace free mPEG in our preparation by electrophoresis on Titan gel HRT kit followed by TCA precipitation. As can be seen in FIG. 19, left panel, Ig-HA-mPEG preparation obtained from the second chromatographic purification (lane 1) like unpegylated Ig-HA preparation (lane 2), did not show detectable amounts of free hydrolyzed mPEG while the preparation collected from the first chromatographic purification contained residual free PEG (lane 4). The amount of free residual mPEG, if any, in the final Ig-HA-mPEG preparation (lane 1) should be lower than $4\times10^{-4}$ M. Calibration experiments indicated that as little as $4\times10^{-4}$ M of mPEG 5,000 can be detected using this technique (lane 3).

When a duplicate gel was stained with Coomassie/Ponceau (FIG. 19, right panel), only Ig-HA and Ig-HA-mPEG conjugates were revealed (lanes 1, 2, respectively) but not free hydrolyzed mPEG (lane 3). Interestingly, pegylated Ig-HA showed better staining with Ponceau S than unpegylated Ig-HA. The differential staining may be attributed to different ability of the two dyes to access their specific sites on the native protein versus the pegylated one. Using this assay, we also were able to trace free mPEG polymers in preparations of chicken egg ovalbumin-mPEG, BSA-mPEG and bovine gamma globulin-mPEG conjugates.

Although small amounts of PEG polymers can be detected by sensitive techniques such as Childs' assay (Childs, 1975, Microchem. J. 20: 190–192) or Veronese's test (Schiavon, et al., 1990, M. Farmaco., 45(6): 791–795), our electrophoretic technique is able to distinguish free PEG from PEG attached to proteins.

Figure 20:
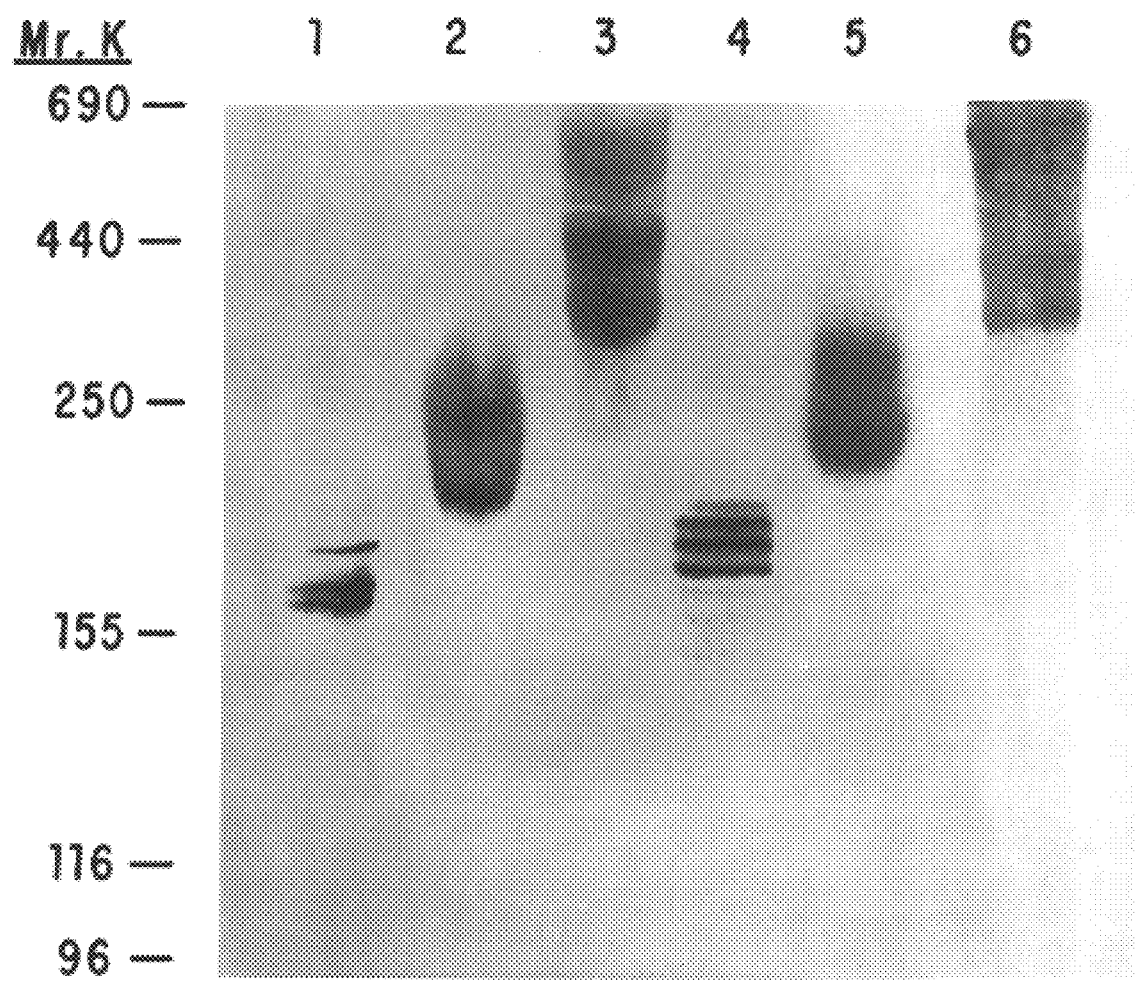
Figure 21A:
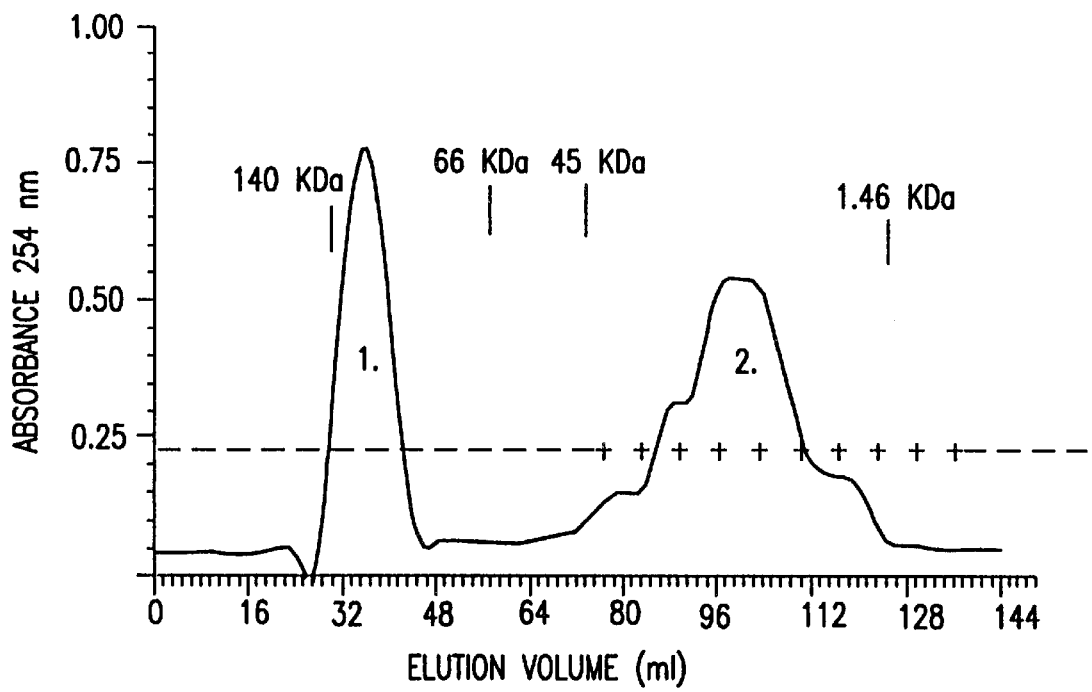
Figure 21B:
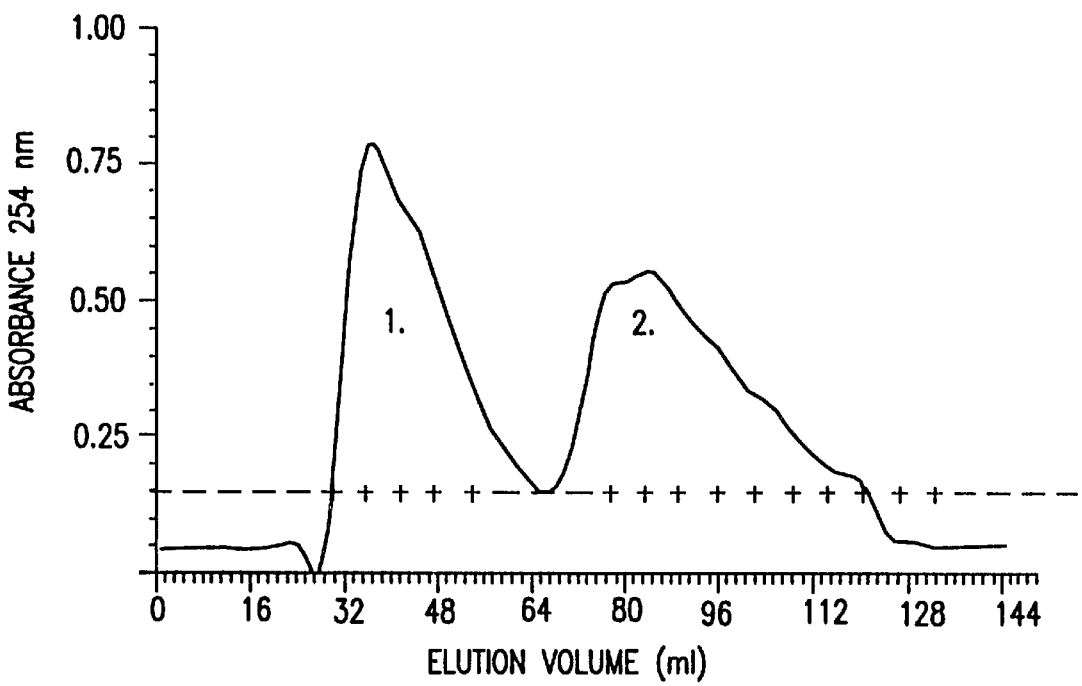

Furthermore we performed SDS-PAGE analysis to investigate the homogeneity of AIgs-mPEG preparations. This was carried out on 4–15% gradient gels (PhastGels, Pharmacia) under non reducing conditions. The results illustrated in FIG. 20 show that the final Ig-HA-mPEG and Ig-V$_3$C-mPEG preparation (peak 2 in FIG. 18) were purified to homogeneity (lanes 2 and 5 respectively). These preparations do not contain detectable amounts of unpegylated AIgs because no comigration with free Ig-HA (lane 1) or Ig-V$_3$C (lane 4) was observed. They do not contain highly pegylated AIgs either because no material comigrated with samples representing heavily pegylated AIgs (from peak 1 in FIG. 18). In summary, we were able to select homogeneous population of AIg-mPEG with 6–8% degree as indicated by these electrophoretic analyses.

The pegylated Ig-HA, showed a long half life and induced strong T cell activation in mice in vivo.

Various publications are cited herein which are hereby incorporated by reference in their entirety.

What is claimed is:

1. A chimeric immunoglobulin molecule, wherein a CDR loop of a parent immunoglobulin molecule is deleted and replaced, in the chimeric immunoglobulin molecule, with a peptide comprising a T cell epitope, wherein a second CDR loop of the parent immunoglobulin, other than the CDR loop replaced by the T cell epitope, is deleted and replaced, in the chimeric immunoglobulin molecule, with a second peptide comprising a B cell epitope.

2. The chimeric immunoglobulin molecule of claim 1, wherein the CDR loop replaced by the T cell epitope and the CDR loop replaced by the B cell epitope are located in the heavy chain of the parent immunoglobulin molecule and are selected from the group consisting of CDR1, CDR2, and CDR3.

3. The chimeric immunoglobulin molecule of claim 1, wherein the CDR loop replaced by the T cell epitope is located in the heavy chain of the parent immunoglobulin molecule and is selected from the group consisting of CDR1, CDR2, and CDR3 and the CDR loop replaced by the B cell epitope is located in the light chain of the parent immunoglobulin molecule and is selected from the group consisting of CDR1, CDR2 and CDR3.

4. The chimeric immunoglobulin molecule of claim 1, wherein the CDR loop replaced by the T cell epitope is located in the light chain of the parent immunoglobulin molecule and is selected from the group consisting of CDR1, CDR2, and CDR3 and the CDR loop replaced by the B cell epitope is located in the heavy chain of the parent immunoglobulin molecule and is selected from the group consisting of CDR1, CDR2 and CDR3.

5. The chimeric immunoglobulin molecule of claim 1, wherein the T cell epitope and the B cell epitope are different peptides comprised in the same virus, the virus being selected from the group consisting of respiratory syncytial virus, measles virus, rotavirus, hepatitis C virus, influenza virus, and human immunodeficiency virus.

6. A composition comprising the chimeric immunoglobulin molecule of claim 1.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (iii) ORIGINAL SOURCE:
    (A) ORGANISM: Human Immunodefficiency Virus Type 1

(iv) FEATURE:
    (A) NAME/KEY:
    (B) LOCATION: 301...319
    (C) OTHER INFORMATION: Envelope Protein gp120

(v) SEQUENCE DESCRIPTION: SEQ ID NO:1:

Arg Lys Ser Ile His Ile Gly Pro Gly Arg Ala Phe Tyr Thr Thr Gly
 1               5                  10                  15

Glu Ile Ile (2) INFORMATION FOR SEQ ID NO:2:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Influenza Virus (iv) FEATURE:
        (A) NAME/KEY:
        (B) LOCATION:
        (C) OTHER INFORMATION: HA1 hemagglutinin protein (xi) SEQUENCE DESCRIPTION: SEQ ID NO:2:

Trp Leu Thr Lys Lys Gly Asp Ser Tyr Pro
 1               5                  10

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Influenza Virus (iv) FEATURE:
        (A) NAME/KEY:
        (B) LOCATION:
        (C) OTHER INFORMATION: H3 protein (xi) SEQUENCE DESCRIPTION: SEQ ID NO:3:

Trp Leu Thr Lys Ser Gly Ser Thr Tyr Pro
 1               5                  10

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) ORIGINAL SOURCE:
        (A) ORGANISM: Influenza Virus (iv) FEATURE:
        (A) NAME/KEY:
        (B) LOCATION:

(C) OTHER INFORMATION: H2 protein (xi) SEQUENCE DESCRIPTION: SEQ ID NO:4:

Trp Leu Thr Lys Glu Gly Ser Asp Tyr Pro
    1               5                   10

(2) INFORMATION FOR SEQ ID NO:5:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Measles Virus (iv) FEATURE:
            (A) NAME/KEY:
            (B) LOCATION: 404...414
            (C) OTHER INFORMATION: F protein (xi) SEQUENCE DESCRIPTION: SEQ ID NO:5:

Ile Asn Gln Asp Pro Asp Lys Ile Leu Thr Tyr
    1               5                   10

(2) INFORMATION FOR SEQ ID NO:6:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Foot and Mouth Disease Virus (iv) FEATURE:
            (A) NAME/KEY:
            (B) LOCATION: 141...160
            (C) OTHER INFORMATION: VP1 protein (xi) SEQUENCE DESCRIPTION: SEQ ID NO:6:

Met Asn Ser Ala Pro Asn Leu Arg Gly Asp Leu Gln Lys Val Ala Arg
    1               5                   10                  15

Thr Leu Pro (2) INFORMATION FOR SEQ ID NO:7:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Influenza PR8A Virus (iv) FEATURE:
            (A) NAME/KEY:
            (B) LOCATION: 110...120
            (C) OTHER INFORMATION: Hemagglutinin Protein (xi) SEQUENCE DESCRIPTION: SEQ ID NO:7:

Ser Phe Glu Arg Phe Glu Ile Phe Pro Lys Glu
    1               5                   10

(2) INFORMATION FOR SEQ ID NO:8:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM:

(iv) FEATURE:
       (A) NAME/KEY:
       (B) LOCATION:
       (C) OTHER INFORMATION: Tetanus Toxoid Protein (xi) SEQUENCE DESCRIPTION: SEQ ID NO:8:

Asn Ser Val Asp Asp Ala Leu Ile Asn Ser Thr Lys Ile Tyr Ser Tyr
1               5                   10                  15

Phe Pro Ser Val
            20

(2) INFORMATION FOR SEQ ID NO:9:

(i) SEQUENCE CHARACTERISTICS:
       (A) LENGTH: 17 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM:

(iv) FEATURE:
       (A) NAME/KEY:
       (B) LOCATION:
       (C) OTHER INFORMATION: Tetanus Toxoid (xi) SEQUENCE DESCRIPTION: SEQ ID NO:9:

Pro Glu Ile Asn Gly Lys Ala Ile His Leu Val Asn Asn Glu Ser Ser
1               5                   10                  15

Glu (2) INFORMATION FOR SEQ ID NO:10:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (iii) ORIGINAL SOURCE:
       (A) ORGANISM:

(iv) FEATURE:
       (A) NAME/KEY:
       (B) LOCATION: 88...103
       (C) OTHER INFORMATION: Cytochrome C Protein (xi) SEQUENCE DESCRIPTION: SEQ ID NO:10:

Ala Asn Glu Arg Ala Asp Leu Ile Ala Tyr Leu Gln Ala Thr Lys
1               5                   10                  15

(2) INFORMATION FOR SEQ ID NO:11:

```
        (i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Mycobacteria (iv) FEATURE:
            (A) NAME/KEY:
            (B) LOCATION:   350...369
            (C) OTHER INFORMATION:  Heat Shock Protein (xi) SEQUENCE DESCRIPTION: SEQ ID NO:11:

Asp Gln Val His Phe Gln Pro Leu Pro Pro Ala Val Val Lys Leu Ser
1               5                  10                  15

Asp Ala Leu Ile
            20

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Hen (iv) FEATURE:
            (A) NAME/KEY:
            (B) LOCATION:   48...61
            (C) OTHER INFORMATION:  Egg White Lysozyme (xi) SEQUENCE DESCRIPTION: SEQ ID NO:12:

Asp Gly Ser Thr Asp Tyr Gly Ile Leu Gln Ile Asn Ser Arg
1               5                  10

(2) INFORMATION FOR SEQ ID NO:13:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) ORIGINAL SOURCE:
            (A) ORGANISM: Streptococcus A (iv) FEATURE:
            (A) NAME/KEY:
            (B) LOCATION:   308...319
            (C) OTHER INFORMATION:  M Protein (xi) SEQUENCE DESCRIPTION: SEQ ID NO:13:

Gln Val Glu Lys Ala Leu Glu Glu Ala Asn Ser Lys
1               5                  10

(2) INFORMATION FOR SEQ ID NO:14:

(i) SEQUENCE CHARACTERISTICS:
            (A) LENGTH: 20 amino acids
            (B) TYPE: amino acid
            (C) STRANDEDNESS: single
```

(D) TOPOLOGY: linear (ii) MOLECULE TYPE: peptide (iii) ORIGINAL SOURCE:
           (A) ORGANISM: Staphylococcus sp.

(iv) FEATURE:
           (A) NAME/KEY:
           (B) LOCATION: 81...100
           (C) OTHER INFORMATION: Nuclease Protein (xi) SEQUENCE DESCRIPTION: SEQ ID NO:14:

Arg Thr Asp Lys Tyr Gly Arg Gly Leu Ala Tyr Ile Tyr Ala Asp Gly
 1               5                  10                  15

Lys Met Val Asn
         20

(2) INFORMATION FOR SEQ ID NO:15:

(i) SEQUENCE CHARACTERISTICS:
           (A) LENGTH: 15 amino acids
           (B) TYPE: amino acid
           (C) STRANDEDNESS: single
           (D) TOPOLOGY: linear (ii) MOLECULE TYPE: peptide (iii) ORIGINAL SOURCE:
           (A) ORGANISM: Influenza PR8A Virus (iv) FEATURE:
           (A) NAME/KEY:
           (B) LOCATION: 147...161
           (C) OTHER INFORMATION: NP Protein (xi) SEQUENCE DESCRIPTION: SEQ ID NO:15:

Thr Tyr Gln Arg Thr Arg Ala Leu Val Arg Thr Gly Met Asp Pro
 1               5                  10                  15

(2) INFORMATION FOR SEQ ID NO:16:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: cDNA (iii) ORIGINAL SOURCE:
           (A) ORGANISM: Influenza PR8A Virus (iv) FEATURE:
           (A) NAME/KEY:
           (B) LOCATION:
           (C) OTHER INFORMATION: site B of HA (xi) SEQUENCE DESCRIPTION: SEQ ID NO:16:

CCCCATCCTA GGCAGGAAAA GCCAATTGGT                                        30

(2) INFORMATION FOR SEQ ID NO:17:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: protein (iii) ORIGINAL SOURCE:
           (A) ORGANISM: Influenza PR8A Virus (iv) FEATURE:
            (A) NAME/KEY:
            (B) LOCATION:
            (C) OTHER INFORMATION: site B of HA (xi) SEQUENCE DESCRIPTION: SEQ ID NO:17:

Trp Leu Thr Glu Asp Glu Gly Ser Tyr Pro
 1               5                  10

(2) INFORMATION FOR SEQ ID NO:18:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (iii) ORIGINAL SOURCE:
(A) ORGANISM:

(iv) FEATURE:
(A) NAME/KEY:
(B) LOCATION:
(C) OTHER INFORMATION: primer (xi) SEQUENCE DESCRIPTION: SEQ ID NO:18:

AGCTGAGGAC AAAGAAGA 18

(2) INFORMATION FOR SEQ ID NO:19:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: cDNA (iii) ORIGINAL SOURCE:
(A) ORGANISM:

(iv) FEATURE:
(A) NAME/KEY:
(B) LOCATION:
(C) OTHER INFORMATION: primer (xi) SEQUENCE DESCRIPTION: SEQ ID NO:19:

CCGAAAAGGA GGGATCCTAT CCCAAGACCA CACTGACTGT ACACAAA 47

(2) INFORMATION FOR SEQ ID NO:20:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) ORIGINAL SOURCE:
(A) ORGANISM:

(iv) FEATURE:
(A) NAME/KEY:
(B) LOCATION:
(C) OTHER INFORMATION: primer (xi) SEQUENCE DESCRIPTION: SEQ ID NO:20:

CAAATCACCC AAGTGTATGG C 21

(2) INFORMATION FOR SEQ ID NO:21:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) ORIGINAL SOURCE:
        (A) ORGANISM:

(iv) FEATURE:
        (A) NAME/KEY:
        (B) LOCATION:
        (C) OTHER INFORMATION: primer (xi) SEQUENCE DESCRIPTION: SEQ ID NO:21:

```
GGGATAGGAT CCCTCCTTTT CGGTTAACCA TCCAATCCAT TCCAGCCCCT           50

GTCCAGGCCT                                                      60
```

(2) INFORMATION FOR SEQ ID NO:22:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) ORIGINAL SOURCE:
        (A) ORGANISM: human immunodeficiency virus (iv) FEATURE:
        (A) NAME/KEY:
        (B) LOCATION: 12-35
        (C) OTHER INFORMATION: HIV-1 HxB2

(xi) SEQUENCE DESCRIPTION: SEQ ID NO:22:

```
Glu Leu Asp Arg Trp Glu Lys Ile Arg Leu Arg Pro Gly Gly Lys Lys
 1               5                  10                  15

Lys Tyr Lys Leu Lys His Ile Val
            20
```

(2) INFORMATION FOR SEQ ID NO:23:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) ORIGINAL SOURCE:
        (A) ORGANISM: human immunodeficiency virus (iv) FEATURE:
        (A) NAME/KEY:
        (B) LOCATION: 325-349
        (C) OTHER INFORMATION: HIV reverse transcriptase (xi) SEQUENCE DESCRIPTION: SEQ ID NO:23:

```
Ala Ile Phe Gln Ser Ser Met Thr Lys Ile Leu Glu Pro Phe Arg Lys
 1               5                  10                  15

Gln Asn Pro Asp Ile Val Ile Tyr Gln
            20                  25
```

(2) INFORMATION FOR SEQ ID NO:24:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) ORIGINAL SOURCE:
        (A) ORGANISM: human immunodeficiency virus (iv) FEATURE:
        (A) NAME/KEY:
        (B) LOCATION: 301-319
        (C) OTHER INFORMATION: HIV gp 120, WMJ2

(xi) SEQUENCE DESCRIPTION: SEQ ID NO:24:

```
Arg Arg Ser Leu Ser Ile Gly Pro Gly Arg Ala Phe Arg Thr Arg Glu
 1               5                  10                  15
Ile Ile Gly
```

(2) INFORMATION FOR SEQ ID NO:25:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) ORIGINAL SOURCE:
        (A) ORGANISM: human immunodeficiency virus (iv) FEATURE:
        (A) NAME/KEY:
        (B) LOCATION: 519-535
        (C) OTHER INFORMATION: HIV-1 IIIB (xi) SEQUENCE DESCRIPTION: SEQ ID NO:25:

```
Ala Val Gly Ile Gly Ala Leu Phe Leu Gly Phe Leu Gly Ala Ala Gly Ser
 1               5                  10                  15
```

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) ORIGINAL SOURCE:
        (A) ORGANISM: Influenza PR8A Virus (iv) FEATURE:
        (A) NAME/KEY:
        (B) LOCATION:
        (C) OTHER INFORMATION: site B of HA (xi) SEQUENCE DESCRIPTION: SEQ ID NO:26:

```
Trp Leu Thr Glu Lys Glu Gly Ser Tyr Pro
 1               5                  10
```

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS: single -continued

```
        (D) TOPOLOGY: linear (ii) MOLECULE TYPE: protein (iii) ORIGINAL SOURCE:
        (A) ORGANISM: Influenza Virus (iv) FEATURE:
        (A) NAME/KEY:
        (B) LOCATION: 365-379
        (C) OTHER INFORMATION:  NP protein (xi) SEQUENCE DESCRIPTION: SEQ ID NO:27:

Ile Ala Ser Asn Glu Asn Met Asp Ala Met Glu Ser Ser Thr Ser
 1               5                  10                  15
```